(12) United States Patent
Konopka et al.

(10) Patent No.: US 10,480,094 B2
(45) Date of Patent: Nov. 19, 2019

(54) ELECTROCHEMICAL METHODS, DEVICES AND COMPOSITIONS

(71) Applicant: Alligant Scientific, LLC, Aurora, CO (US)

(72) Inventors: Daniel A. Konopka, Denver, CO (US); Jason A. Seedig, Castle Rock, CO (US)

(73) Assignee: Iontra LLC, Denver, CO (US)

( * ) Notice: Subject to any disclaimer, the term of this patent is extended or adjusted under 35 U.S.C. 154(b) by 166 days.

(21) Appl. No.: 15/649,569

(22) Filed: Jul. 13, 2017

(65) Prior Publication Data

US 2018/0016697 A1   Jan. 18, 2018

Related U.S. Application Data

(60) Provisional application No. 62/361,650, filed on Jul. 13, 2016.

(51) Int. Cl.
*C25D 3/66* (2006.01)
*C25D 5/18* (2006.01)
(Continued)

(52) U.S. Cl.
CPC ........... *C25D 13/18* (2013.01); *C07D 233/58* (2013.01); *C08G 69/32* (2013.01); *C25D 3/665* (2013.01);
(Continued)

(58) Field of Classification Search
CPC .......... C25D 5/18; C25D 13/18; C25D 21/12; C25D 13/02; C25D 13/22
See application file for complete search history.

(56) References Cited

U.S. PATENT DOCUMENTS 1,582,617 A   4/1926   Mohn
3,482,217 A   12/1969   Finney
(Continued)

FOREIGN PATENT DOCUMENTS

DE   102011106294   1/2013
JP   10-025600   1/1998
(Continued)

OTHER PUBLICATIONS

Choi, Soon-Don et al., The Development of the Zinc Electroplating on the Dented Door Frame of Automobile, Journal of the Institute of Industrial Technology, 28(1):123-130, 2000 (8 pages).
(Continued)

*Primary Examiner* — Brian W Cohen
(74) *Attorney, Agent, or Firm* — Polsinelli PC

(57) ABSTRACT

The disclosure provides a method comprising inducing a first current between a source of a countercharge and a first electrode, the first current being through an electrolyte. In some instances, the first current is not present. A second current, in the form of waveform, is induced across the first electrode, the second current being transverse to the first current, and the second current inducing a relativistic charge across the first electrode. Metal from the electrolyte is deposited on the substrate or corroded from the substrate, among other things. The methods, as well as associated apparatus, improve deposition, bonding, corrosion, and other effects.

30 Claims, 19 Drawing Sheets
(8 of 19 Drawing Sheet(s) Filed in Color)

(51) Int. Cl.
| | |
|---|---|
| *C25D 13/02* | (2006.01) |
| *C25D 13/18* | (2006.01) |
| *C25D 13/22* | (2006.01) |
| *C25D 21/12* | (2006.01) |
| *C25D 15/00* | (2006.01) |
| *C25D 13/12* | (2006.01) |
| *C07D 233/58* | (2006.01) |
| *C08G 69/32* | (2006.01) |
| *H01M 10/0564* | (2010.01) |
| *C25D 17/00* | (2006.01) |
| *C25D 17/02* | (2006.01) |
| *H01M 4/00* | (2006.01) |
| *H01M 10/0525* | (2010.01) |
| *H01M 10/06* | (2006.01) |
| *C25D 3/38* | (2006.01) |

(52) U.S. Cl.
CPC .............. *C25D 5/18* (2013.01); *C25D 13/02* (2013.01); *C25D 13/12* (2013.01); *C25D 13/22* (2013.01); *C25D 15/00* (2013.01); *C25D 17/00* (2013.01); *C25D 17/02* (2013.01); *C25D 21/12* (2013.01); *H01M 4/00* (2013.01); *H01M 10/0564* (2013.01); *C25D 3/38* (2013.01); *H01M 10/0525* (2013.01); *H01M 10/06* (2013.01)

(56) References Cited

U.S. PATENT DOCUMENTS

| | | |
|---|---|---|
| 3,769,181 A | 10/1973 | Biora et al. |
| 4,159,231 A | 6/1979 | Smith et al. |
| 4,608,138 A | 8/1986 | Kobayashi |
| 5,242,556 A | 9/1993 | Masuzawa |
| 5,731,101 A | 3/1998 | Sherif et al. |
| 5,833,835 A | 11/1998 | Gimaev et al. |
| 6,368,965 B1 | 4/2002 | Lopatin |
| 6,797,144 B2 | 9/2004 | Su et al. |
| 6,835,299 B1 | 12/2004 | Webb et al. |
| 6,884,335 B2 | 4/2005 | Webb et al. |
| 7,628,902 B2 | 12/2009 | Knowlton et al. |
| 7,837,841 B2 | 11/2010 | Chen et al. |
| 8,048,280 B2 | 11/2011 | Mayer et al. |
| 8,182,932 B2 | 5/2012 | Hatano |
| 8,333,941 B1 | 12/2012 | Atanassov et al. |
| 8,475,636 B2 | 7/2013 | Mayer et al. |
| 2002/0169516 A1 | 11/2002 | Brussee et al. |
| 2003/0038036 A1 | 2/2003 | Collins |
| 2005/0201176 A1 | 9/2005 | Zangari et al. |
| 2005/0261565 A1 | 11/2005 | Lane et al. |
| 2006/0131175 A1 | 6/2006 | Anton et al. |
| 2006/0163055 A1 | 7/2006 | Vereecken et al. |
| 2007/0034529 A1 | 2/2007 | Bard et al. |
| 2007/0240993 A1 | 10/2007 | Nakato et al. |
| 2008/0035489 A1 | 2/2008 | Allardyce et al. |
| 2008/0202922 A1* | 8/2008 | Zhong .................. C23C 18/1669 204/273 |
| 2008/0253922 A1 | 10/2008 | Trimmer et al. |
| 2009/0301891 A1 | 12/2009 | Locktman et al. |
| 2011/0256807 A1 | 10/2011 | Feng et al. |
| 2012/0061244 A1* | 3/2012 | Hubel .................... C25D 7/123 205/137 |
| 2012/0091495 A1 | 4/2012 | Hatanaka et al. |
| 2012/0126716 A1 | 5/2012 | Hirakawa |
| 2013/0001198 A1 | 1/2013 | Arvin et al. |
| 2013/0036930 A1* | 2/2013 | Sullivan .............. F42C 19/0803 102/202.7 |
| 2013/0112564 A1 | 5/2013 | Kleiman-Shwarsctein et al. |
| 2013/0137242 A1 | 5/2013 | He et al. |
| 2013/0220819 A1 | 8/2013 | Hall et al. |
| 2014/0144781 A1 | 5/2014 | He |
| 2015/0171455 A1 | 6/2015 | Mills |
| 2018/0010258 A1* | 1/2018 | Fujiwara .................. C25D 5/18 |
| 2018/0016697 A1 | 1/2018 | Konopka et al. |
| 2018/0019496 A1 | 1/2018 | Konopka et al. |

FOREIGN PATENT DOCUMENTS

| | | |
|---|---|---|
| JP | 10-229271 | 8/1998 |
| JP | 10-330987 | 12/1998 |
| JP | 2000-265293 | 9/2000 |
| JP | 2000-290798 | 10/2000 |
| JP | 2003-064499 | 3/2003 |
| JP | 2003-129294 | 5/2003 |
| JP | 2003-268597 | 9/2003 |
| JP | 2004-047788 | 2/2004 |
| JP | 2004-162166 | 6/2004 |
| JP | 2004-263218 | 9/2004 |
| JP | 2005-171317 | 6/2005 |
| JP | 2005-200675 | 7/2005 |
| JP | 2006-009154 | 1/2006 |
| JP | 2006-089810 | 4/2006 |
| JP | 2006-117963 | 5/2006 |
| JP | 2006-283151 | 10/2006 |
| JP | 2006-328470 | 12/2006 |
| JP | 2007-046070 | 2/2007 |
| JP | 2007-505996 | 3/2007 |
| JP | 2007-507615 | 3/2007 |
| JP | 2007-204832 | 8/2007 |
| JP | 2007-227929 | 9/2007 |
| JP | 2007-234750 | 9/2007 |
| JP | 2007-308783 | 11/2007 |
| JP | 2008-019501 | 1/2008 |
| JP | 2008-025000 | 2/2008 |
| JP | 2008-504444 | 2/2008 |
| JP | 2009-173952 | 8/2009 |
| JP | 2009-228124 | 10/2009 |
| JP | 2011-009267 | 1/2011 |
| JP | 2010-067580 | 1/2017 |
| KR | 1998-0087024 | 12/1998 |
| KR | 10-0160149 | 5/1999 |
| KR | 2001-0014062 | 2/2001 |
| KR | 2001-0024154 | 3/2001 |
| KR | 2001-0033089 | 4/2001 |
| KR | 10-2003-0013046 | 2/2003 |
| KR | 2003-0011316 | 2/2003 |
| KR | 10-2004-0058475 | 7/2004 |
| KR | 10-0443628 | 8/2004 |
| KR | 10-0460368 | 12/2004 |
| KR | 10-0465545 | 2/2005 |
| KR | 10-2005-0075449 | 7/2005 |
| KR | 10-2005-0094083 | 9/2005 |
| KR | 10-0707121 | 4/2007 |
| KR | 10-2007-0116564 | 12/2007 |
| KR | 10-2008-0061218 | 7/2008 |
| KR | 10-2009-0083489 | 8/2009 |
| KR | 10-2010-0131279 | 12/2010 |
| KR | 10-2011-0021686 | 3/2011 |
| KR | 10-2012-0000744 | 1/2012 |
| KR | 10-2012-0008891 | 2/2012 |
| KR | 10-2012-0101290 | 9/2012 |
| KR | 10-2013-0060164 | 6/2013 |
| KR | 10-2013-0136941 | 12/2013 |
| KR | 10-2014-0063854 | 5/2014 |
| KR | 10-2014-0067948 | 6/2014 |
| WO | WO 2018/013868 | 1/2018 |
| WO | WO 2018/013874 | 1/2018 |

OTHER PUBLICATIONS

Chung, Soon-hyo et al., The Effect of Auxiliary Electrodes on Uniformity of Electrodeposit, Korean Journal of Metals and Materials, 42(6):494-495, 2004 (2 pages).

Hwang, Yang Jin, A Study of Chromium Electroplating Layer of ABS Copolymer by Auxiliary Cathode, Dept. of Mechatronics Engineering, Master's Thesis, Tong-Myong University, 2008 (51 pages).

International Searching Authority, International Search Report and Written Opinion, issued for PCT/US2017/042018, dated Sep. 27, 2017 (9 pages).

(56) References Cited

OTHER PUBLICATIONS

International Searching Authority, International Search Report and Written Opinion, issued for PCT/US2017/042025, dated Nov. 17, 2017 (12 pages).

Ispas, Adriana et al., Electrodeposition in Ionic Liquids, The Electrochemical Society, Inferface, Spring 2014, pp. 47-51 (5 pages).

Kim, Gyeong-Su et al., Development and Characteristic Evaluation of Auxiliary Anode for Uniformed Plating of Aluminum Wheel, Korean Society for Surface Engineering, Fall Meeting, Oct. 14, 2009, pp. 148 (http://scholar.ndsl.kr/schDetail.do?cn=NPAP08385401).

Kim, N. S. et al., Optimization of Current Distributions of Electroplating on Patterned Substrates with the Auxiliary Electrode, Journal of Korean Institute of Surface Engineering, 28(3):164-173, 1995 (10 pages).

Kobayashi, Takeshi et al., Via Filing by Electroplating under Various Waveforms, Journal of the Surface Finishing Society of Japan, 49(12):1332-1335, 1998 (4 pages).

Kondo, Kazuo et al., Shape Evolution of Via Filing Electrodeposit, Journal of the Japan Institute of Electronics Packaging, 4(1):37-40, 2001 (4 pages).

Kondo, Kazuo, Copper Damascene Electrodeposition and Through Plug Formation for Three Dimensional Packaging, Journal of the Surface Finishing Society of Japan, 55(12): 907-910, 2004 (4 page).

Seki, Hiroshi, Electrical Application to concrete Members, Concrete Journal, 36(2):17-26, 1998 (10 pages).

Seki, Hiroshi, Electrical Application to concrete Members, Concrete Journal, 36(4):3-9, 1998 (7 pages).

Andy Abbott, Deep Eutectic Solvents, Chemistry Department, University of Leicester, www.le.ac.uk (70 pages).

\* cited by examiner

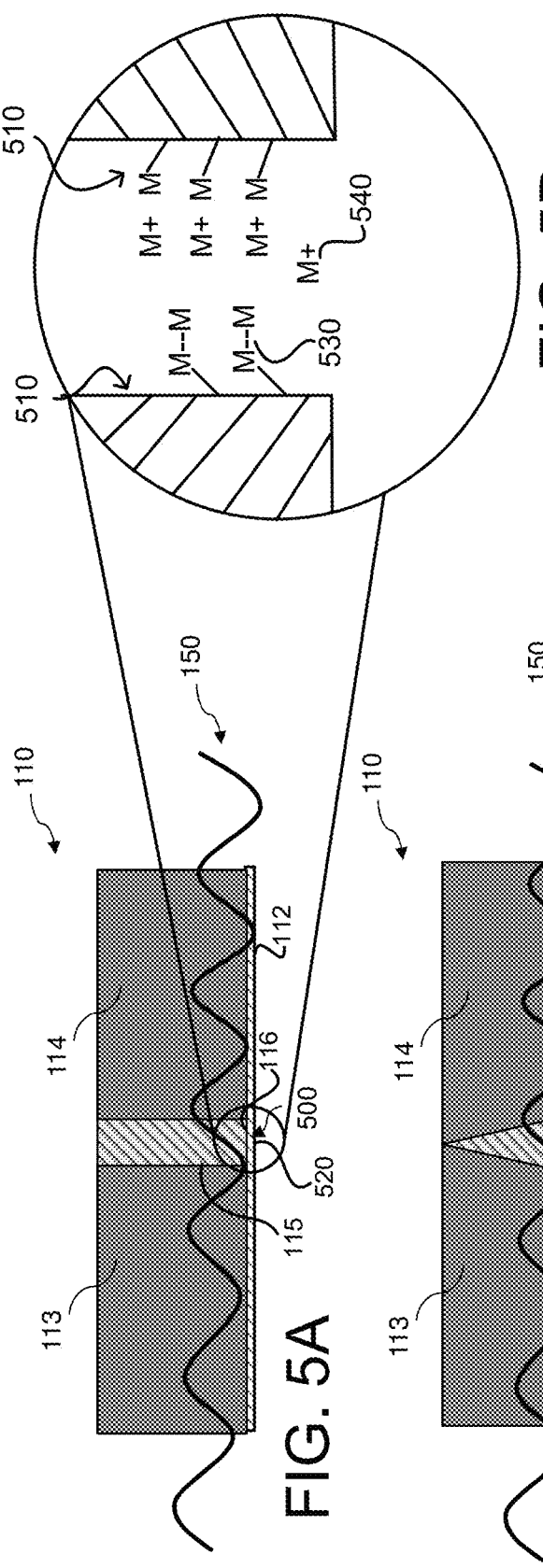

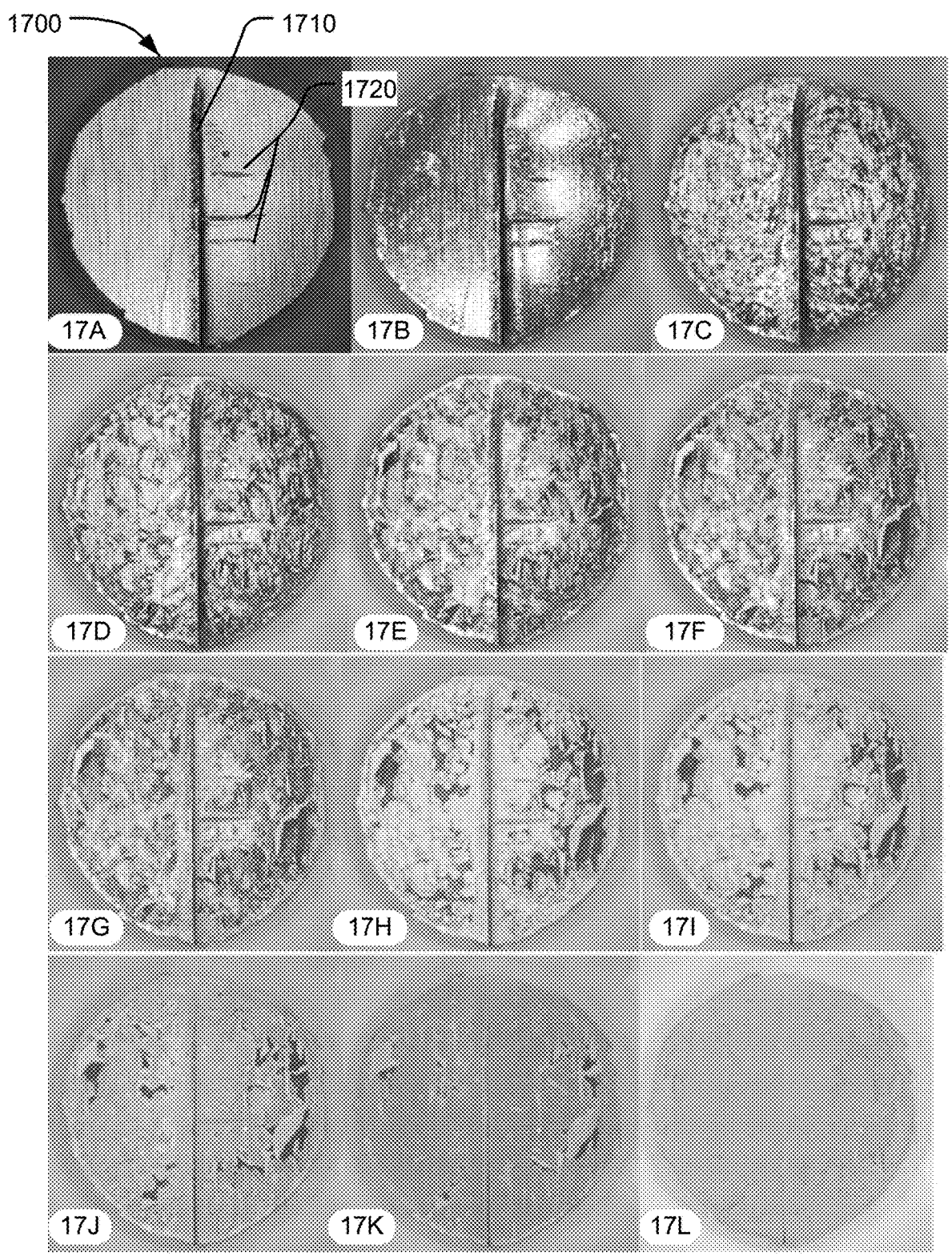
FIGS. 17A-L

ELECTROCHEMICAL METHODS, DEVICES AND COMPOSITIONS

CROSS-REFERENCE TO RELATED APPLICATION

The present application claims priority under 35 U.S.C. § 119(e) to Provisional Application No. 62/361,650 titled "Electrochemical Methods, Devices and Compositions," filed on Jul. 13, 2016, which is hereby incorporated by reference herein.

TECHNICAL FIELD

Aspects of the present disclosure involve electrochemistry, and particularly materials bonding, surface repair, electroplating, corrosion and electrocatalysis.

BACKGROUND

Traditional material fusion techniques, such as welding, have serious limitations. For example, often fusion techniques cannot be applied to materials with heat or electricity constraints. In one specific example, support beams are vulnerable to warping and possible failure when heated to temperatures needed for traditional welding. In another example, objects near sensitive electronics and volatile chemicals cannot be fused, re-fused or restored by conventional means (smelting, brazing, and welding) until separated from such sensitive equipment or materials. These methods also cannot be used on metallic materials which require contiguous, uniform properties.

Welding is a common method for fusing metal pieces by heating the surfaces to the point of melting using a blowtorch, electric arc, or other means, and uniting the metal pieces by pressing, hammering, or the like. Metals tend to be either machinable or weldable, which poses a widespread challenge in the manufacturing industry. For example, many advanced alloys are machinable, but conventional welding would alter their precise grain structures and destroy the properties of the alloy. Welded and heat-treated joints experience changes to their material properties with consequences to stress and strain distribution, heat conduction, static dissipation, etc. As such, the conventional welding is not compatible with all industrially relevant metals.

Alternatively, electrodeposition is a process for coating a thin layer of one metal on top of a substrate, often to modify its surface properties. Although electrodeposition does not require the high temperatures of welding for melting metal surface, the thin layers of metal obtained from electrodeposition are cannot join and unite metal pieces in a mechanically strong or durable way.

It is with these issues in mind, among others, that aspects of the present disclosure were conceived.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Provided herein is a method comprising inducing a first current between a source of a countercharge and a first electrode, the first current being through an electrolyte. A second current is induced across the first electrode. The second current is transverse to the first current, and the second current inducing a relativistic charge across the first electrode. The method may further comprise applying a signal cancellation to reduce a far-field radiation from the first electrode.

The present disclosure also provides a method comprising inducing an electric field between a source of a countercharge and a first electrode, the electric field having field lines through an electrolyte. A potential is induced across a surface of the first electrode. The induced potential bends the field lines proximate the surface such that metal from the electrolyte follows a path of the bent field lines to deposit the metal onto the surface.

The present disclosure further provides a method comprising inducing a potential across a surface of an electrode in the presence of a chemical potential between an electrolyte and the surface of the electrode. The induced potential relativistically charges the surface of the electrode.

The present disclosure provides a corroding electrode comprising one or more metal species selected from the group consisting of metal particles, metal ions, and combinations thereof. The corroding electrode dissolves when a first current is applied between the corroding electrode and a first electrode through an electrolyte, thereby suspending the one or more metal species into the electrolyte.

Provided herein is a device comprising a source of a countercharge, and a first electrode in electrical communication through an electrolyte with the source of a countercharge; wherein a first current is induced through the electrolyte between the source of a countercharge and the first electrode; and wherein a second current is induced across the first electrode, the second current being transverse to the first current, and the second current inducing a relativistic charge across the first electrode.

The present disclosure may also provide a device comprising a source of a countercharge, and a first electrode in electrical communication through an electrolyte with the source of a countercharge. An electric field is induced between the source of a countercharge and the first electrode. The electric field has field lines through the electrolyte. A potential is induced across a surface of the first electrode. The induced potential bends the field lines proximate the surface such that metal from the electrolyte follows a path of the bent field lines to deposit the metal onto the surface.

The present disclosure provides an electrode, wherein a potential is induced across a surface of the electrode in the presence of a chemical potential between an electrolyte and the surface of the electrode. The induced potential relativistically charges the surface of the electrode. This electrode may be a first electrode in any method or device described herein.

The present disclosure further provides a device comprising a main control unit comprising a power supply and a power modulator; an electrode applicator unit, comprising at least one source of a countercharge and a plurality of channels for flowing an electrolyte through the electrode applicator unit, the electrode applicator unit being connected to the main control unit; a current collector cable connected to the main control unit; and a power control unit connected to the main control unit. The power control unit applies a first current between a first electrode and the at least one source of a countercharge through the electrolyte, the power control unit inducing a second current across the first electrode, the second current being transverse to the first current, and the second current inducing a relativistic charge across the first electrode.

Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification and the drawings, which forms a part of this disclosure.

BRIEF DESCRIPTION OF THE DRAWINGS

The application file contains at least one drawing executed in color. Copies of this patent application publication with color drawing(s) will be provided by the Office upon request and payment of the necessary fee. Example embodiments are illustrated in referenced figures of the drawings. It is intended that the embodiments and figures disclosed herein are to be considered illustrative rather than limiting.

FIGS. 5A-5D depict several first electrodes with features filled by operation of the methods described herein. In FIG. 5A, a second current 150 transverse a first electrode 110 having a void 500 between a first portion 113 and a second portion 114. The second current 150 produces a relativistic charge 112 on the first electrode 110, whereby metal is bonded to a first edge 115 and a second edge 116 to fill a gap 520 in the void 500. FIG. 5B depicts a process similar to FIG. 5A, where the void 500 is a high-aspect ratio feature in the first electrode 110. In FIG. 5C, a rough surface 111 of the first electrode 110 is filled. FIG. 5D is an inset of FIG. 5A showing the formation of a new metal-metal bond 530 between a metal 540 in the electrolyte 140, and a metal edge 510 of the first edge 115 in the void 500.

FIG. 6A shows the process without a second current 150; that is, a conventional electrodeposition. FIG. 6B shows application of a second current 150, without a DC offset on non-uniform surfaces. FIG. 6C shows the angles 151, 152, 153 of the second current 150 relative to the void 500. Arrows 611, 612, 613 indicate directions of induced growth.

FIG. 14B was conducted under a second current having a waveform of 5 MHz, 10 Vpp sinusoidal.

FIGS. 17A-17L depict an electrochemical corrosion followed by crack-filling and planar surface deposition. FIG. 17A shows the electrode 1700 with a surface having a cut 1710 and horizontal indentations 1720. FIGS. 17B and 17C show electrochemical corrosion and roughening. FIGS. 17D-17L show the result of an electrochemical process using a second current, providing in smooth, planar surface.

FIG. 18A shows the sample at ×200 magnification and FIG. 18B shows the same sample at ×2000 magnification.

FIG. 19B is a microscopic view of the surface at ×800 magnification. Lighter areas at 10 μm Cu powder, darker areas are CuSO$_4$. Pellet pressed at 80 kpsi for 30 min.

DETAILED DESCRIPTION

Figure 1:
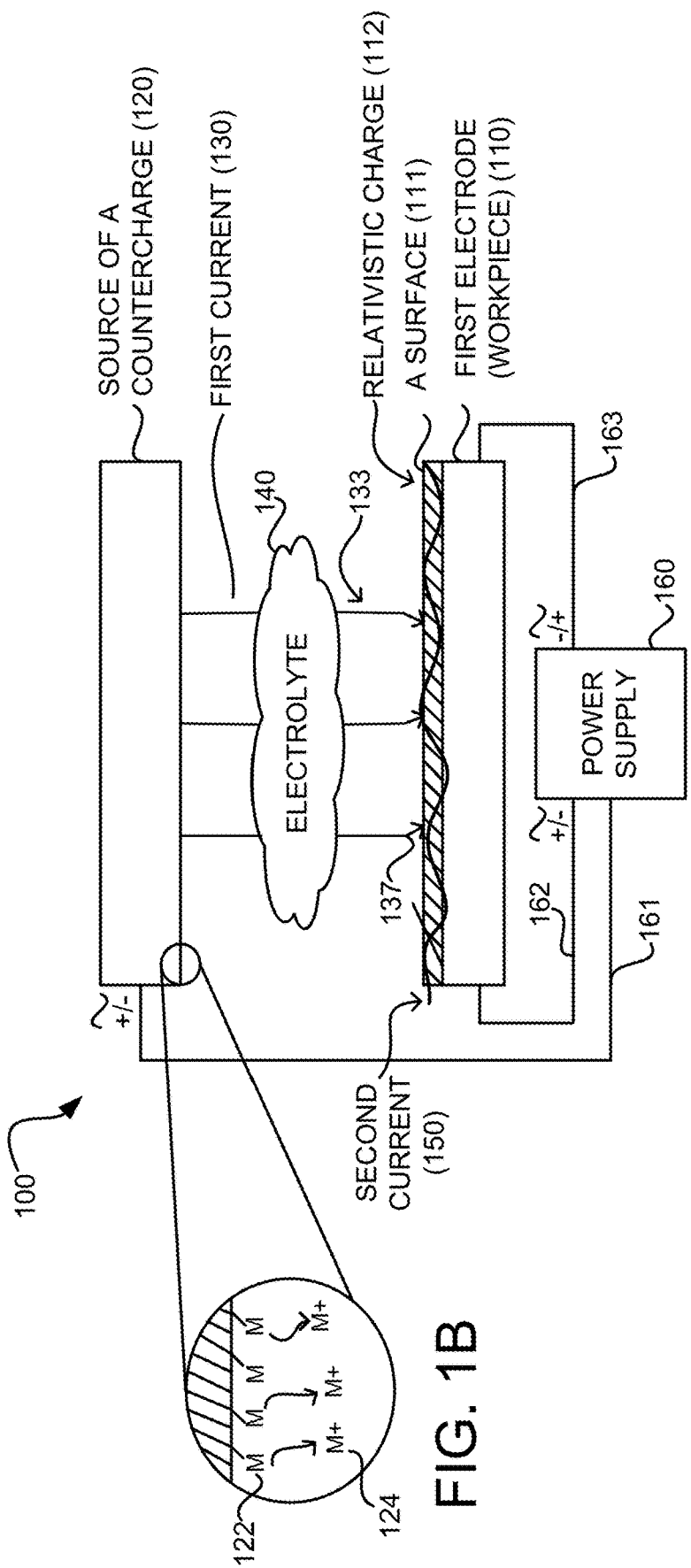
FIG. 1A depicts a device 100 comprising a source of a countercharge 120, and a first electrode 110 in electrical communication with the source of a countercharge 120 through an electrolyte 140. A first current 130 is induced through the electrolyte 140 between the source of a countercharge 120 and the first electrode 110. A second current 150 is induced across the first electrode 110, the second current 150 being transverse to the first current 130, and the second current 150 inducing a relativistic charge 112 across a surface 111 of the first electrode 110. The device also comprises a power supply 160 in electrical communication 161 with the source for a countercharge 120 and in electrical communication 162, 163 with the first electrode 110.
FIG. 1B is an inset of FIG. 1A, showing an embodiment where the source of countercharge 120 is a corroding electrode. When the first current 130 is induced between the corroding electrode 120 and the first electrode 110 through the electrolyte 140, metal 122 from the corroding electrode 120 is released as metal species (M+) 124 into the electrolyte 140.

Provided herein are methods, devices and compositions which electrochemically bond or rearrange metals on surfaces. Generally, the methods and devices operate by inducing a first current between a source of a countercharge and a first electrode through an electrolyte. The electrolyte is adjacent to the surface of the first electrode, forming an electrode-electrolyte interface, where metal from the electrolyte contacts the surface of the first electrode to form new metal-metal bonds during the electrochemical process.

The first electrode may be the workpiece where new metal-metal bonds are formed between metal on the surface and metal from the electrolyte, and is typically charged as a cathode. When a second, transverse current is induced across the first electrode, electrons at the surface of the experience a forward compression and rearward expansion of their electric field. This compression and expansion generates a relativistic charge propagating outward from the electron's center at the speed of light. The relativistic charge then bends the field lines of the first current, directing metal from the electrolyte to form new metal-metal bonds in cracks and crevices, pits and voids, and high-aspect surface features on the workpiece.

Alternatively, the methods and devices described herein may operate by inducing an electric field between a source of a countercharge and a first electrode where the electric field is through an electrolyte. The first electrode may be workpiece on which or to which some operation, such as depositing material or bonding is being performed, according to the techniques discussed herein.

An electric potential is induced across a surface of the first electrode. The induced potential bends the field lines proximate the surface such that metal from the electrolyte follows a path of the bent field lines to deposit the metal onto the surface. In one specific example, the induced potential affects the field lines. These bent field lines ultimately intersect the surface, including irregularities in the surface, at 90 degrees to the portion of the surface being intersected. Viewed another way, the bent field lines of the first current alter the trajectory of the metal from the electrolyte as it deposits onto and bonded to the surface, so the metal has a lower probability of reaching the overall surface at 90° on its approach, but rather conforms to the contours, irregularities, and flaws of the surface so that metal interacts at about 90° related to the discrete portion of the surface it reaches.

The induced potential of the transverse current can be controlled by tuning the waveform, including its voltage, amperage and frequency. Multiple waveforms can even be combined to tune into different features or substances comprising the surface of the workpiece. The extent of metal bonding can be monitored in real-time, such that the transverse current and first current can be modulated to continue metal bonding, electropolishing, or other electrochemical processes on the workpiece. This electrochemical process can also be run in reverse, where corrosion of the workpiece sends metal species into the electrolyte. From either embodiment, the present methods and devices represent a radical departure from conventional metal fusing techniques or previously known electrodeposition methods.

Specifically, conventional metal fusing techniques use an adhesive with material properties different from those of the substrate. Sometimes sheet metal is joined using advanced glues in combination with crimping or rivets for strength, but these methods are limited to thin substrates. Alternatively, fusion techniques such as welding use large amounts of power for heat and/or pressure to melt metal at junctions.

The welding techniques are cumbersome and dangerous. Many resistance welding processes require an inert shielding gas to remove oxygen from the weld area. Gas compression is very inefficient and energy intensive, accounting for up to 10% of industrial electricity consumption. To avoid overheating, welding is limited to a single spot at any time, or multiple spots only if sufficiently spaced. Resistance welding also involves intense UV radiation, deadly voltages and currents, toxic fumes, noise, and flammability concerns.

Welding has severe limitations to which metals to which it can be applied. Welding dissimilar metals, even different grades of alloy having the same base metal, results in cracking and poor adhesion at the joint. Many grades of common metals are non-weldable because of small concentrations of other elements which respond differently to intense heat, such as aircraft grade aluminum (7075-T6), which contains ~10% of other elements including Zn and Cu.

Figures 6A, 6B:
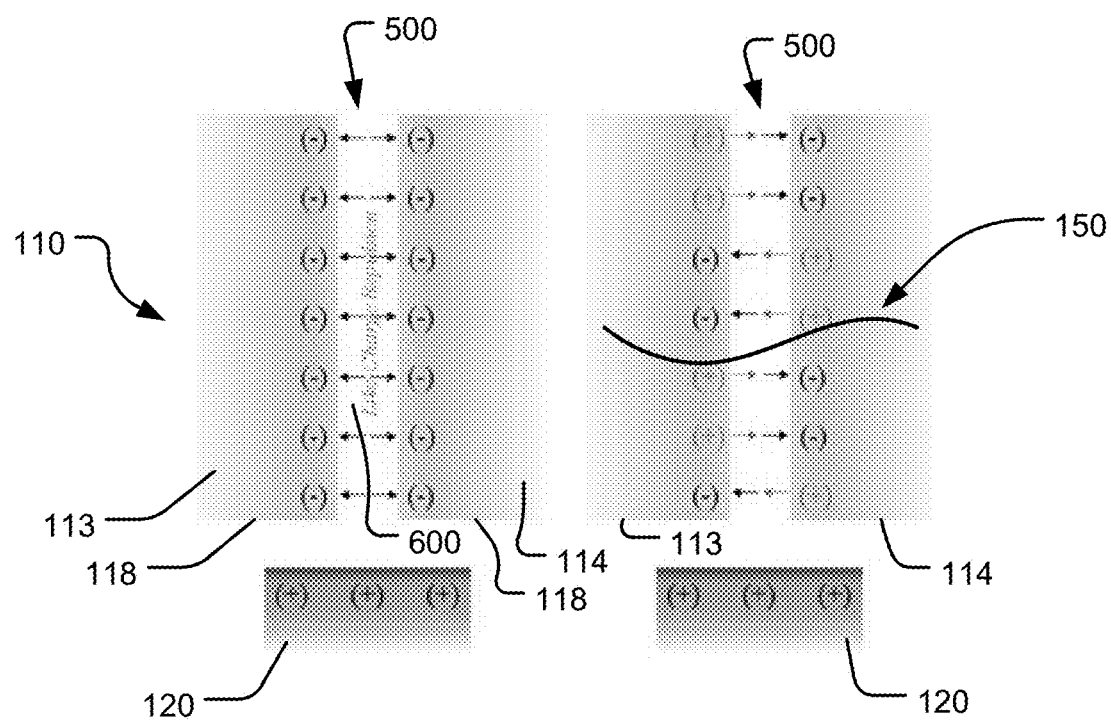
FIGS. 6A-6C depict an electric field 600 inside a void 500 between two portions 113, 114 of the first electrode 110.

Conventional electrodeposition may be used where welding fails, but not without its own set of limitations. Conventional electrodeposition does not form mechanically strong bonds between adjacent workpieces, due to metal surface tension and like-charge repulsion (e.g. as shown at FIG. 6A). Conventional electrodeposition also employs large, typically aqueous, baths of plating solution and direct current applied between an anode and a workpiece—an immersed, conductive cathode to be metal-plated. Plating baths must be of very large volume (hundreds of gallons) for even small workpieces to maintain homogenous reactant concentrations, adequate spacing between the anode and workpiece, and complete peripheral anodic boundaries around the plated object to ensure a uniform electric field, and thus uniform plating on all sides of the object.

During conventional electroplating, disproportionately more material deposits onto areas of curvature than on planar surfaces. A smooth, even finish is usually desired, so chemical and engineering controls must be built into electroplating processes to reduce this effect. Controls usually involve running the plating process at reduced current densities, using multiple, distributed anodes to shift the electric field density, and using organic additives.

For conventional electrodeposition and plating, surfaces must be preprocessed to achieve favorable outcomes. Acid strikes and polishing clean workpiece surfaces and remove native oxides that would otherwise prevent newly deposited material from bonding. Low current densities are used to avoid rough deposits. These steps represent a significant portion of the chemical resources and time in conventional electroplating and deposition.

The present disclosure may be understood by reference to the following detailed description, taken in conjunction with the drawings as described above. It is noted that, for purposes of illustrative clarity, certain elements in various drawings may not be drawn to scale, may be represented schematically or conceptually, or otherwise may not correspond exactly to certain physical configurations of embodiments.

I. Method

Figure 3:
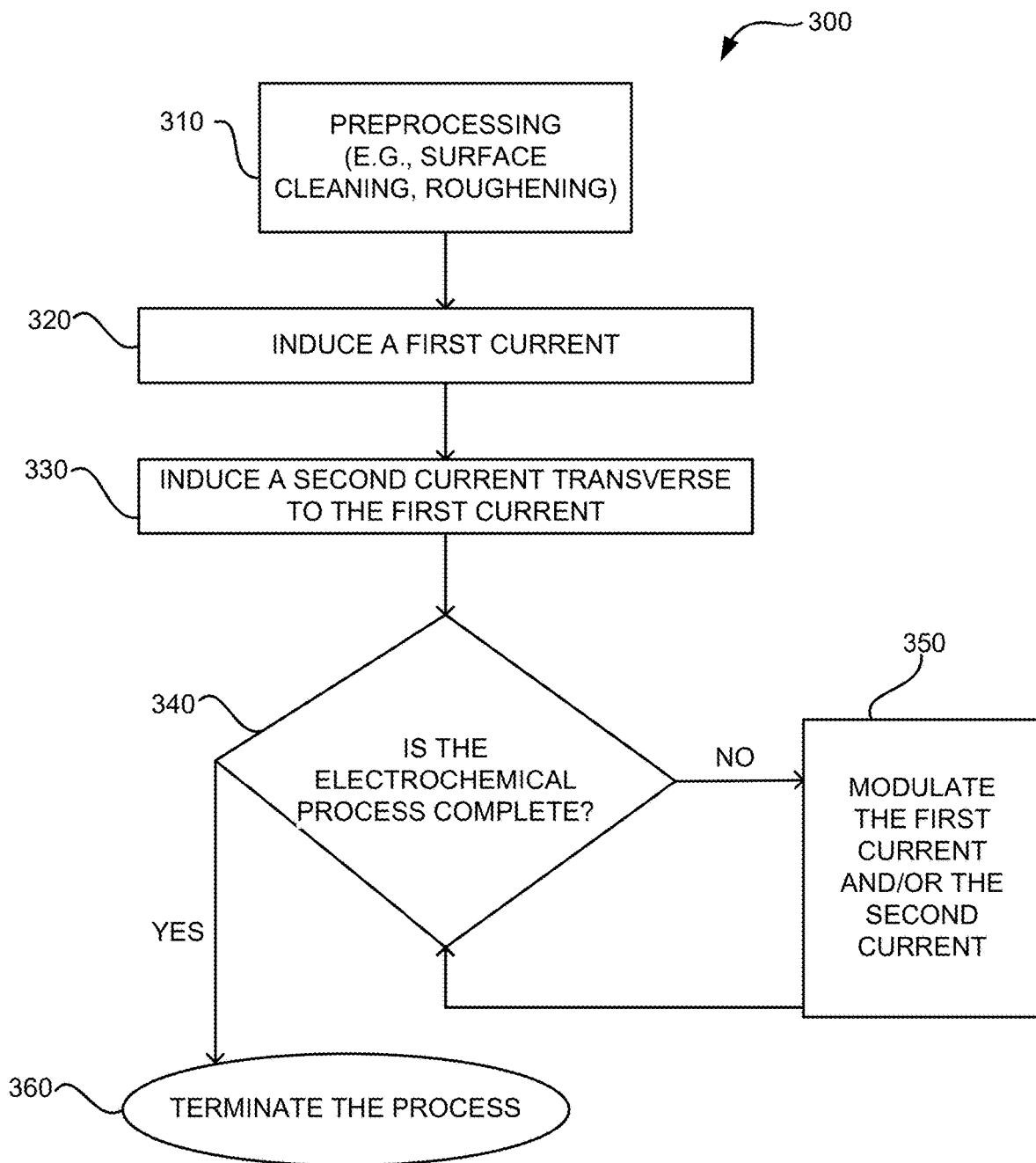
FIG. 3 is a flowchart of the methods described herein. The workpiece may be preprocessed (e.g., surface cleaning, roughening, etc.) (310), before inducing a first current (320) and inducing a second current (330). If the electrochemical process is incomplete (340), the first current and/or the second current may be modulated (350). If the electrochemical process is complete (340), the process terminates (350).

In view of the introduction, as well as issues and limitations relative to conventional processes, provided herein are electrochemical apparatus and methods for depositing and rearranging metals on surfaces. FIG. 1 illustrates an example device for practicing the method discussed herein. FIG. 3 illustrates an example method according to the present disclosure. Referring to FIGS. 1 and 3, a workpiece 110 may be preprocessed (e.g., surface cleaning, roughening, etc.) (310), before inducing a first current (320) and inducing a second current (330), which may be an alternating or non-DC current, across the workpiece. The second current generates a relativistic charge on the workpiece. If the electrochemical process is incomplete (340), the first current and/or the second current may be modulated (350). If the electrochemical process is complete (340), the process terminates (360).

The methods according to this disclosure can be understood with relation to exemplary devices. Referring in more detail to FIG. 1, the device 100 involves a source of a counterchange 120, and a first electrode 110 (which may be the workpiece) in electrical communication with the source of a counterchange 120 through an electrolyte 140. A first current 130 is induced through the electrolyte 140 between the source of a counterchange 120 and the first electrode 110. A second current 150 is induced across the first electrode 110, the second current 150 being transverse to the first current 130, and the second current 150 inducing a relativistic charge 112 across a surface 111 of the first electrode 110. In some embodiments, the device includes a power supply 161 in electrical communication 161 with the source for a counterchange 120 and in electrical communication 162, 163 with the first electrode 110.

Figure 2:
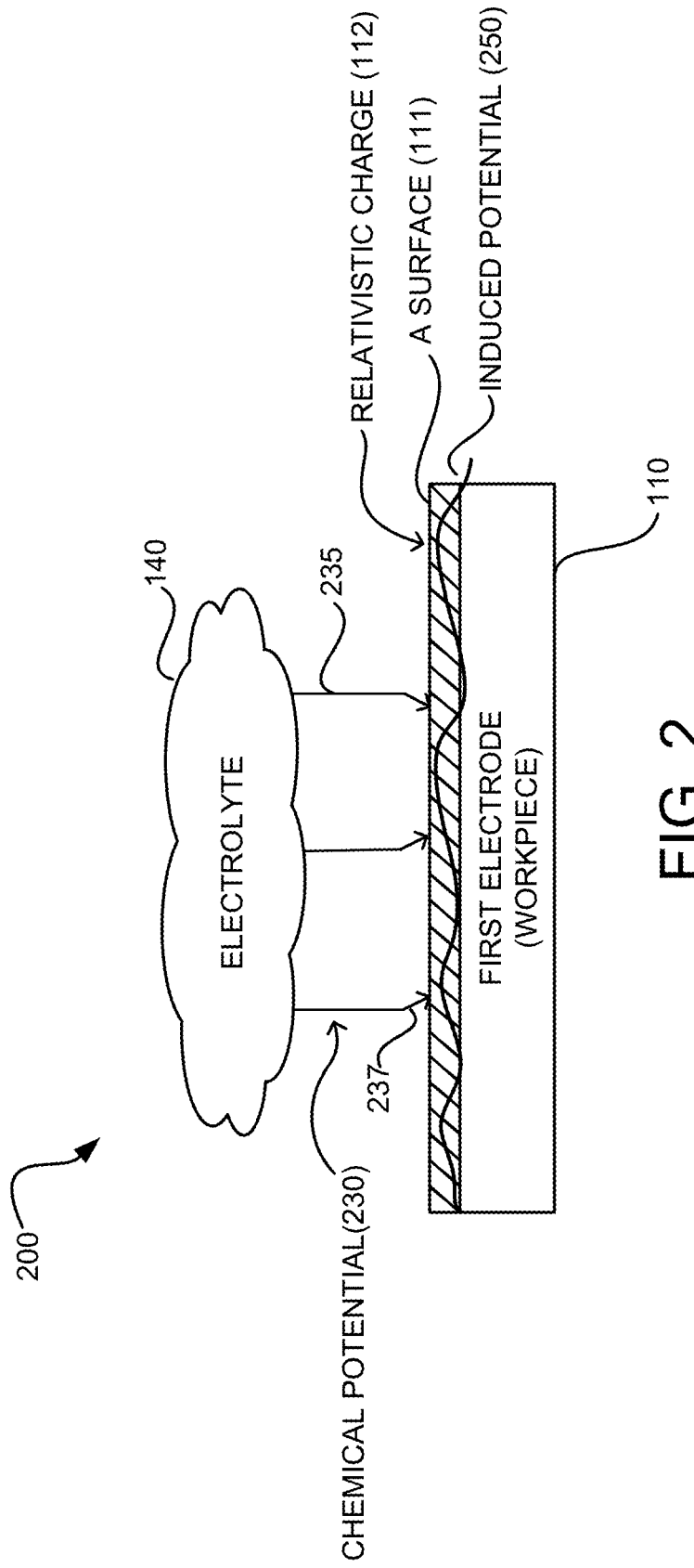
FIG. 2 depicts a first electrode 110, wherein a potential 250 is induced across a surface 111 of the first electrode 110 in the presence of a chemical potential 230 between an electrolyte 140 and the surface 111 of the first electrode 110. The induced potential 250 relativistically charges 112 the surface 111 of the first electrode 110.

Alternatively, the methods according to this disclosure may be contemplated in the context of a device according to FIG. 2. In this embodiment, a first electrode 110 has a potential 250 induced across its surface 111 in the presence of a chemical potential 230 between an electrolyte 140 and the surface 111. The induced potential 250 relativistically charges 112 the surface 111 of the first electrode 110. The induced potential bends the field lines proximate the surface such that metal from the electrolyte follows a path of the bent field lines to deposit and bond the metal onto the material surface.

A. First Electrode (e.g., Workpiece)

The first electrode, in many possible examples discussed herein, may also be considered the workpiece, or workpieces, or the cathode in an electrochemical process. The first electrode may include more than one discrete piece, for example, when one is joining or bonding separate metal pieces.

At the first electrode, negative charge is isolated at a surface nearest the electrolyte, while positive charge is pushed to the first electrode's farthest surfaces. The first electrode is polarized with negative and positive charges when a current (for example, a first current or a transverse current) is applied, or when an electric or chemical potential is induced across the first electrode. The methods according to this disclosure manipulate electron density on the workpiece to guide metal deposition, and the like.

Figure 4A:
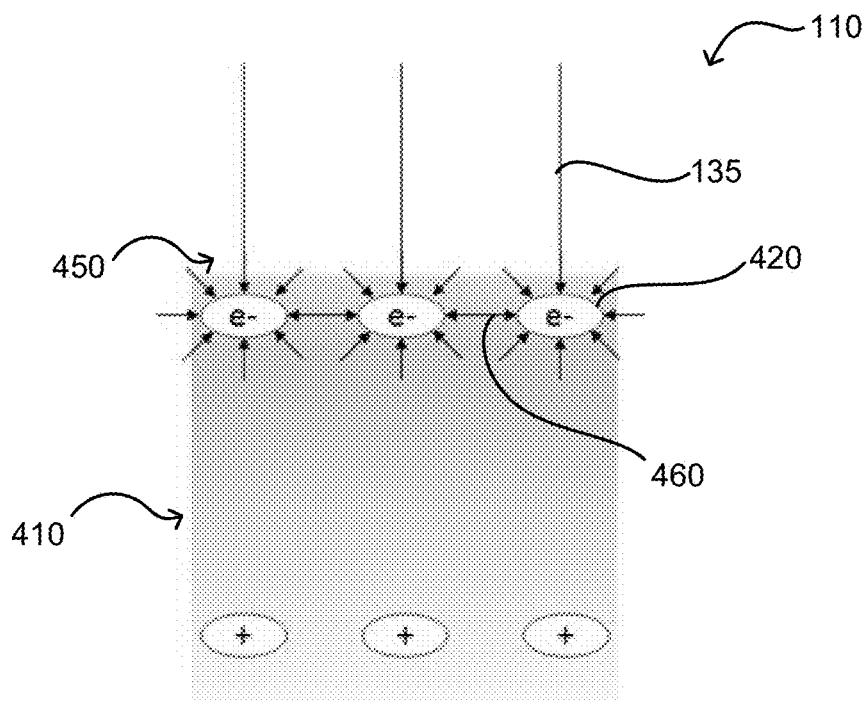
FIG. 4A depicts capacitive charge separation 410 in a first electrode 110. Electric field lines 135 are represented by black arrows pointing toward negative charges (electrons, 420).
Figure 4B:
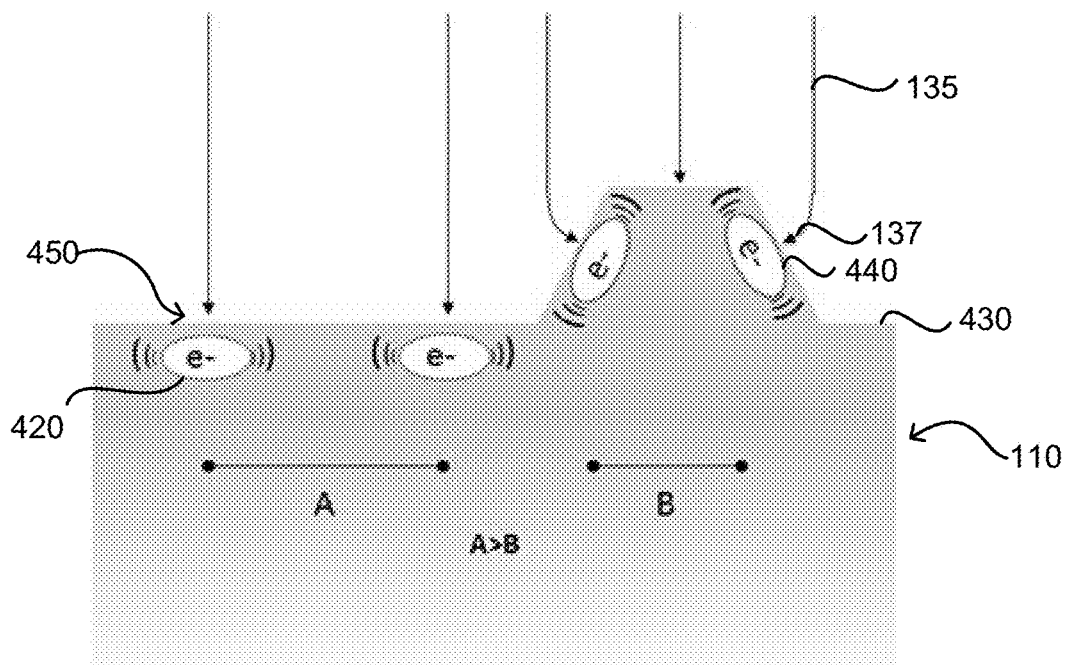
FIG. 4B depicts electron distribution 450 among the electrons 420 on smooth areas 430 and rough areas 440 of the surface 111 of the first electrode 110.

The charge density of a polarized workpiece absent the influence of a second current can be understood with reference to FIGS. 4A and 4B, which illustrate the effects of smoothness and roughness on the substrate. Negatively charged sides 440 have a higher density of electrons 420, which distribute themselves evenly across the surface 111, due to the equal repulsion 460 of their individual electric fields. This repulsion effect 460 occurs parallel to the tangential point of an electron's position at a surface 111. Consequently, extremely smooth surfaces 430 experience the most uniform charge distribution (FIG. 4A), whereas any curvature, such as rough topography, increases charge density (FIG. 4B). As curvature 440 increases, the repulsive forces of local electrons are less in-plane, allowing closer proximity (FIG. 4B).

Continuing to reference FIGS. 4A and 4B, the electric field lines 135 may originate at the source for a counterchange 120 and terminate at the negatively charged surface 111 of the first electrode 110. As described above, the surface 111 becomes negatively charged under operation of a current or an induced potential. Electrons 420 have an electric field in all directions (FIG. 4A), while electron-electron repulsion 460 occurs parallel to the surface 111 (FIG. 4B). Due to electron distribution 450, electric field lines 135 terminate perpendicular to a tangent of the surface 111 and deviate from their original vector (137) to maintain this behavior at curves 440. The increased charge density at non-planar areas of the first electrode results in greater electrochemical activity relative to smooth areas. In other words, the distance A between electrons 420 in smooth regions 430 is greater than the distance B between electrons 420 in rugged regions 440.

The workpiece may have voids and gaps, which affect the electron distribution at the surface. Referring now to FIGS. 5A, 5B, and 5D, the first electrode 110 may have a void 500 with a metal edge 510. The relativistic charge 112 may cause a metal-metal bond 530 to form between metal 540 from the electrolyte 140 and the metal edge 510 to thereby fill the void 500. In various aspects, the void 500 may be a crack, crevice, or fracture in the first electrode. The void 500 of FIG. 5A is in the form of a gap 520 between a first portion 113 of the first electrode 110, the first portion 113 having a first edge 115 of the metal edge 510, and a second portion 114 of the first electrode 110, the second portion 114 with a second edge 116 of the metal edge 510 proximate the first edge 114. The relativistic charge 112 may cause the metal-metal bond 530 to form between metal from the first edge 114 and metal 540 from the electrolyte 140 and between metal from the second edge 116 and metal 540 from the electrolyte 140. The bonded metals bridge the gap 520 to form a unified electrode of the first portion 114 and the second portion.

FIG. 5B depicts a process similar to FIG. 5A, where the void 500 here also is a high-aspect ratio feature in the first electrode 110. The void 500 forms a gap 520 between a first portion 113 of the first electrode 110, the first portion 113 having a first edge 115 of the metal edge 510, and a second portion 114 of the first electrode 110, the second portion 114 with a second edge 116 of the metal edge 510 proximate the first edge 114. The relativistic charge 112 causes the metal-metal bond 530 (as shown in FIG. 5D) to form between metal from the first edge 115 and metal 540 from the electrolyte 140 and between metal from the second edge 116 and metal 540 from the electrolyte 140. The bonded metals bridge the gap 520, with methods at the closing gap bonding, to form a unified electrode of the first portion 113 and the second portion 114, and metals bonded within and across the gap.

In FIG. 5C, a rough surface 111 of the first electrode 110 may be filled with metal bonded from the electrolyte. The relativistic charge 112 causes the metal-metal bond 530 to form between metal from the surface 111 and metal 540 from the electrolyte 140. A chemical potential exists between the electrolyte and the surface of the workpiece. In this context, a transverse current without applying a first current could drive some deposition, although the combination of first current with the transverse current is more effective at depositing more metal than is lost to dissolution or corrosion.

The electrostatic environment of the voids described above can be understood with reference to FIG. 6A, illustrating a conventional electrodeposition process applied to the structure of FIG. 5A in contrast to FIG. 6B, illustrating a process as described herein applied to the structure of FIG. 5A. Referring first to FIG. 6A, absent a second current 150, as in a conventional electrodeposition, void 500 within the first electrode 110 has like charges and experiences repulsion 600. This like-charge repulsion make strong bonding energetically unfavorable, such that metal from the electrolyte does not readily find its way into the void 500 (FIG. 6A). While metal deposition may occur still inside the void 500, it is slow compared to growth atop the surfaces 118, 119 closest the source of a countercharge 120.

Figure 6C:
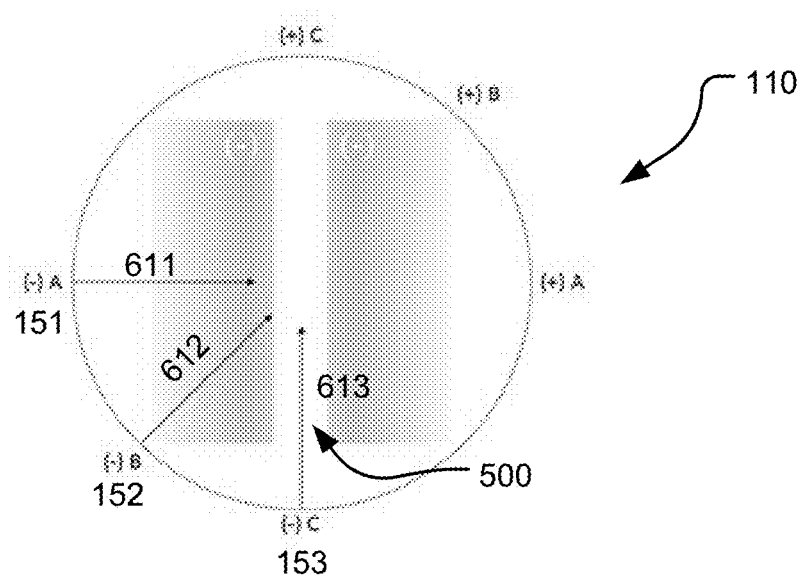

In contrast, now referring to FIG. 6A, using a method according to the present disclosure, a second current 150 flowing from a first portion 113 to a second portion 114 across the first electrode 110 induces a planar electric field in the void 500. The induced potential can be targeted across the area being treated or bonded; the potential need not be induced across the entire workpiece. This electric field of the second current 150 is transverses the first current. Depositing metal species are redirected by the second current 150 and fill the junction 500 instead of immediately depositing on the surfaces 118, 119 of the first electrode 110 nearest to the source of a countercharge 120. FIG. 6C illustrates the angles 151, 152, 153 of the second current 150 relative to the void 500. Arrows 611, 612, 613 indicate directions of induced growth.

B. Electrolyte

The methods and devices described herein use an electrolyte. Generally, the electrolyte comprises a metal, which is a source for new material deposited and bonded at the first electrode. In particular, the electrolyte may comprise a metal and one or more species selected from the group consisting of water, ammonium salts, metal chlorides, metal sulfates, ionic liquids, ionogels, and any combination thereof. When the electrolyte comprises an ammonium salt, the ammonium salt may be a tertiary ammonium salt, a quaternary ammonium salt, or combinations thereof.

1. Solvent

Generally, the electrolyte comprises one or more solvents. The solvent may comprise water, an organic solvent, or ionic liquids. In particular, non-aqueous solutions may include deep eutectic solvents, ionic liquids, room temperature ionic liquids (RTIL), ionogels, and other organic solvents, which support ionic conductivity and metal dissolution.

When present, the organic solvent may be a polar protic solvent, a polar aprotic solvent, a non-polar solvent, or combinations thereof. Suitable examples of polar protic solvents include, but are not limited to alcohols such as methanol, ethanol, isopropanol, n-propanol, isobutanol, n-butanol, s-butanol, t-butanol, and the like; diols such as propylene glycol; organic acids such as formic acid, acetic acid, and so forth; amines such as trimethylamine, or triethylamine, and the like; amides such as formamide, acetamide, and so forth; and combinations of any of the above.

Non-limiting examples of suitable polar aprotic solvents include acetonitrile, dichloromethane (DCM), diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (THF), 2-methyltetrahydrofuran, trichloromethane, and combinations thereof.

Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof.

A electrolyte comprising organic solutions frequently exhibit greater viscosity, which can cause slower molecular diffusion but benefits from increased particle suspension capacity. Electrolyte having organic solvent may also display much larger electrochemical windows (2 V to 6 V), compared to water (about 1.23 V). Organic solvents may also have greater operating temperature ranges above the 100° C. limit for aqueous systems. Generally, organic solutions do not codeposit with the metal during deposition. Organic solvents also allow deposition of more reactive metals, including pure Fe and Al. For at least these reasons, some electrolytes may comprise an organic solvent.

In other embodiments, the electrolyte may comprise an ionic liquid, such as a room-temperature ionic liquid (RTIL), which are relatively non-volatile, highly tunable molten salts whose melting points are below ambient temperature. RTILs are solvents with low viscosities (10-100 cP), low melting points, a range of densities, and relatively small molar volumes. Generally, RTILs consist of a cation and an anion.

The cation in the RTIL may include, but is not limited to, imidazolium, phosphonium, ammonium, and pyridinium. In particular embodiments, the RTIL comprises an imidazolium cation; that is, the RTIL is an imidazolium-based ionic liquid. Each cation may be substituted with one or more R groups, such as an imidazolium having the formula [Rmim] or [R$_2$mim], wherein "mim" references the imidazolium. The R group may comprise one or more n-alkyl, branched alkyl, alkenyl, such as vinyl or allyl, alkynyl, fluoroalkyl, benzyl, styryl, hydroxyl, ether, amine, nitrile, silyl, siloxy, oligo(ethylene glycol), isothiocyanates, and sulfonic acids. In particular, the R group may be an alkyl selected from methyl or ethyl.

The RTIL may be functionalized with one, two, three, or more oligo(alkylene glycol) substituents, such as an oligo (ethylene glycol). Alternatively, the oligo(alkylene glycol) may be a methylene glycol or a propylene glycol. A vicinal diol substituent on the RTILs may provide greater aqueous solubility and possible water miscibility. Polymerizable RTILs may be provided choosing one or more R groups on the cation from a styrene, vinyl, allyl, or other polymerizable group.

Examples of suitable cations in the RTIL include, but are not limited to, 1-ethyl-3-methyl imidazolium ([EMIM]), 1-hexyl-3-methyl imidazolium ([HMIM]), 1-vinyl-3-ethyl-imidazolium ([VEIM]), 1-allyl-3-methyl-imidazolium ([AMIM]), 1-hexyl-3-butyl-imidazolium ([HBIM]), 1-vinyl-3-methylimidazolium ([VMIM]), 1-hydroxyundecanyl-3-methylimidazolium ([($C_{11}$OH)MIM]), tetrabutylphosphonium ([P4444]), 1-(2,3-dihydroxypropyl)-alkyl imidazolium ([(dhp)MIM]), and combinations thereof. For example, the cation may be 1-ethyl-3-methyl imidazolium ([EMIM]). The cation may be 1-hexyl-3-methyl imidazolium ([HMIM]). The cation may be 1-vinyl-3-ethyl-imidazolium ([VEIM]). The cation may be 1-allyl-3-methyl-imidazolium ([AMIM]). The cation may be 1-hexyl-3-butyl-imidazolium ([HBIM]), 1-vinyl-3-methylimidazolium ([VMIM]). The cation may be 1-hydroxyundecanyl-3-methylimidazolium ([($C_{11}$OH)MIM]). The cation may be tetrabutylphosphonium ([P4444]). The cation may also be 1-(2,3-dihydroxypropyl)-alkyl imidazolium ([(dhp)MIM]).

Suitable anions (X) in the RTIL include, but are not limited to, chloride (Cl), bromide (Br), iodide (I), triflate (OTf), dicyanamide (DCA), tricyanomethanide (TCM), tetrafluoroborate ($BF_4$), hexafluorophosphate ($PF_6$), taurinate (Tau), and bis(trifluoromethane)sulfonimide (TSFI). For example, the anion may be triflate (OTf). The anion may be dicyanamide (DCA). The anion may be tricyanomethanide (TCM). The anion may be tetrafluoroborate (BF4). The anion may be hexafluorophosphate (PF6). The anion may be taurinate (Tau). The anion may be bis(trifluoromethane)sulfonimide (TFSI).

Any combination of cations and anions described herein may be used to form a suitable RTIL. Examples of suitable RTILs include, but are not limited to, 1-ethyl-3-methyl imidazolium bis(trifluoromethane)sulfonamide ([EMIM][TFSI]), 1-hexyl-3-methyl imidazolium bis(trifluoromethane)sulfonamide ([HMIM][TFSI]), 1-vinyl-3-ethyl-imidazolium bis(trifluoromethane)sulfonamide ([VEIM][TFSI]), 1-allyl-3-methyl-imidazolium bis(trifluoromethane)sulfonamide ([AMIM][TFSI]), 1-hexyl-3-butyl-imidazolium bis(trifluoromethane)sulfonamide ([HBIM][TFSI]), 1-vinyl-3-methylimidazolium bis(trifluoromethane)sulfonamide ([VMIM][TFSI]), 1-hydroxyundecanyl-3-methylimidazolium bis(trifluoromethane)sulfonamide ([($C_{11}$OH)MIM][TFSI]), 1-ethyl-3-methylimidazolium tricyanomethanide ([EMIM][TCM]), tetrabutylphosphonium taurinate, ([P4444][Tau]), 1-ethyl-3-methylimidazolium dicyanamide ([EMIM][DCA]), 1-(2,3-dihydroxypropyl)-alkyl imidazolium dicyanamide ([(dhp)MIM][DCA]), 1-(2,3-dihydroxypropyl)-3-alkyl imidazolium tetrafluoroborate ([(dhp)MIM][BF4]), 1-(2,3-dihydroxypropyl)-3-alkyl imidazolium bis(trifluoromethane)sulfonimide ([(dhp)MIM][TFSI]), 1-(2,3-dihydroxypropyl)-3-alkyl imidazolium hexafluorophosphate ([(dhp)MIM][PF6]), or combinations thereof. In particular, the room-temperature ionic liquid may be 1-ethyl-3-methylimidazolium chloride (EMIC). Exemplary RTILs are further illustrated below at Table 1.

TABLE 1

Exemplary RTILs.

| Abbreviation | Chemical Name | Structure |
|---|---|---|
| EMIC, [EMIM][Cl] | 1-ethyl-3-methylimidazolium chloride | 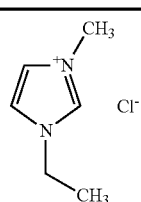 |
| [EMIM][TSFI] | 1-ethyl-3-methylimidazolium bis(trifluoromethane)sulfonimide | 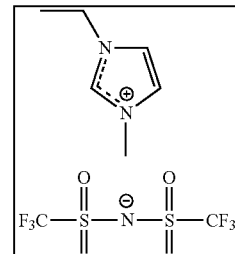 |
| [VEIM][TSFI] | 1-vinyl-3-ethyl-imidazolium bis(trifluoromethane)sulfonimide | 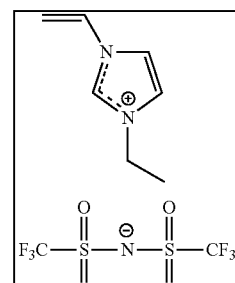 |

TABLE 1-continued

Exemplary RTILs.

| Abbreviation | Chemical Name | Structure |
| --- | --- | --- |
| [HMIM][TSFI] | 1-hexyl-3-methyl-imidazolium bis(trifluoromethane)sulfonimide | 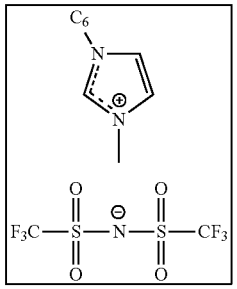 |
| [AMIM][TSFI] | 1-allyl-3-methyl-imidazolium bis(trifluoromethane)sulfonimide | 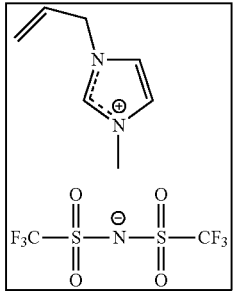 |
| [HBIM][TSFI] | 1-hexyl-3-butyl-imidazolium bis(trifluoromethane)sulfonimide | 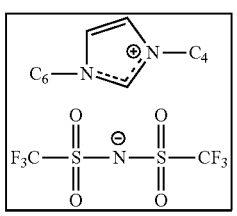 |
| [VMIM][TSFI] | 1-vinyl-3-methylimidazolium bis(trifluoromethane)sulfonimide | 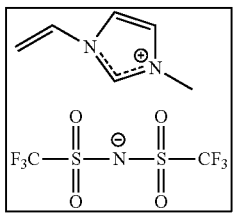 |
| [($C_{11}$OH)MIM][TSFI] | 1-hydroxyundecanyl-3-methylimidazolium bis(trifluoromethane)sulfonimide | 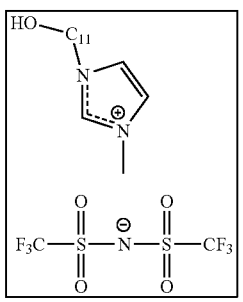 |

TABLE 1-continued

Exemplary RTILs.

| Abbreviation | Chemical Name | Structure |
|---|---|---|
| [EMIM][TCM] | 1-ethyl-3-methylimidazolium tricyanomethanide | 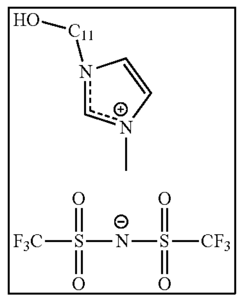 |
| [P4444][Tau] | tetrabutylphosphonium taurinate | 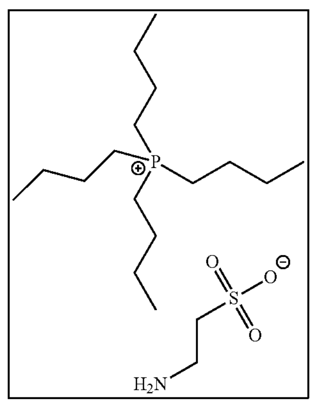 [SMILES: CCCC[P+](CCCC)(CCCC)CCCC ; NCCS(=O)(=O)[O-]] |
| [EMIM][DCA] | 1-ethyl-3-methylimidazolium dicyanamide | 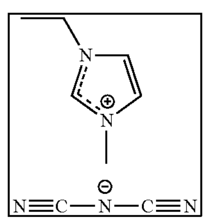 |
| [DMIM][Tf2N] or [DEIM][Tf2N] | 1-(2,3-dihydroxypropyl)-3-methylimidazolium bis(trifluoromethanesulfonimide) or 1-(2,3-dihydroxypropyl)-3-ethylimidazolium bis(trifluoromethanesulfonimide) | 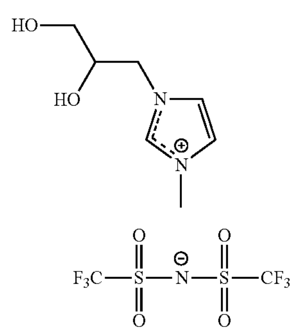 |
| [DMIM][BF4] or [DEIM][BF4] | 1-(2,3-dihydroxypropyl)-3-methylimidazolium tetrafluoroborate or 1-(2,3-dihydroxypropyl)-3-ethylimidazolium tetrafluoroborate | 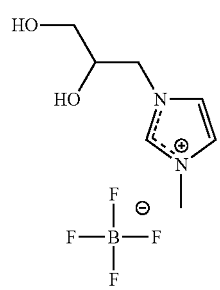 |

TABLE 1-continued

Exemplary RTILs.

| Abbreviation | Chemical Name | Structure |
| --- | --- | --- |
| [DMIM][DCA] or [DEIM][DCA] | 1-(2,3-dihydroxypropyl)-3-methylimidazolium dicyanamide or 1-(2,3-dihydroxypropyl)-3-ethylimidazolium dicyanamide | 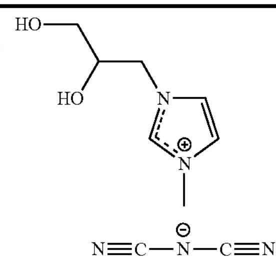 |
| [DMIM][PF6] or [DEIM][PF6] | 1-(2,3-dihydroxypropyl)-3-methylimidazolium hexafluorophosphate or 1-(2,3-dihydroxypropyl)-3-ethylimidazolium hexafluorophosphate | 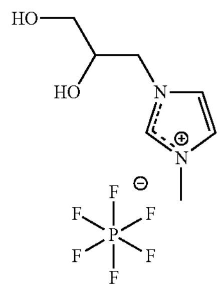 |

The electrolyte may comprise a mixture of water and an RTIL. For such mixtures, the volume ratio may be between about 99:1 and about 1:99 water/RTIL, such as between about 99:1 and about 95:5 water/RTIL, between about 95:5 and about 90:10 water/RTIL, between about 90:10 and about 85:15 water/RTIL, between about 85:15 and about 80:20 water/RTIL, between about 80:20 and about 75:25 water/RTIL, between about 75:25 and about 70:30 water/RTIL, between about 70:30 and about 65:35 water/RTIL, between about 65:35 and about 60:40 water/RTIL, between about 60:40 and about 55:45 water/RTIL, between about 55:45 and about 50:50 water/RTIL, between about 50:50 and about 55:45 water/RTIL, between about 55:45 and about 45:65 water/RTIL, between about 45:65 and about 40:60 water/RTIL, between about 40:60 and about 35:65 water/RTIL, between about 35:65 and about 30:70 water/RTIL, between about 30:70 and about 25:75 water/RTIL, between about 25:75 and about 20:80 water/RTIL, between about 20:80 and about 15:85 water/RTIL, between about 15:85 and about 10:90 water/RTIL, between about 10:90 and about 5:95 water/RTIL, or between about 5:95 and about 1:99 water/RTIL. In particular, the molar ratio may between about 70:30 and about 20:80 water/RTIL, between about 60:40 and about 30:70 water/RTIL, or at about 40:60 water/RTIL.

The electrolyte may have at a temperature above 0° C. and below about 250° C., such between about +0° C. and about 10° C., between about 10° C. and about 20° C., between about 20° C. and about 30° C., between about 30° C. and about 40° C., between about 40° C. and about 50° C., between about 50° C. and about 60° C., between about 60° C. and about 70° C., between about 70° C. and about 80° C., between about 80° C. and about 90° C., between about 90° C. and about 100° C., between about 100° C. and about 110° C., between about 110° C. and about 120° C., between about 120° C. and about 130° C., between about 130° C. and about 140° C., between about 140° C. and about 150° C., between about 150° C. and about 160° C., between about 160° C. and about 170° C., between about 170° C. and about 180° C., between about 180° C. and about 190° C., between about 190° C. and about 200° C., between about 200° C. and about 210° C., between about 210° C. and about 220° C., between about 220° C. and about 230° C., between about 230° C. and about 240° C., between about 240° C. and about 250° C., between about 250° C. and about 260° C., between about 260° C. and about 270° C., between about 270° C. and about 280° C., between about 280° C. and about 290° C., or between about 290° C. and about 300° C.

The pH of the electrolyte may vary depending upon the embodiment. Different metals and composites typically have pH requirements to maintain a stable mixture in solution. The wetting characteristics of surfactant maintain its presence at the first electrode/electrolyte interface. Therefore, the surfactant may also buffer against the dramatic pH gradients that occur between the interface and the electrolyte bulk due to proton consumption and metal hydroxide precipitation on the substrate.

2. Metal

Generally, the electrolyte comprises metal. The metal may be metal particles, such as dissolved or suspended metallic micro- or nanoparticles, or molecular metal ions, such as dissolved metal salts. Examples of suitable metals include, but are not limited to, zinc, cadmium, copper, nickel, chromium, tin, gold, silver, platinum, lead, ruthenium, rhodium, palladium, osmium, iridium, iron, cobalt, indium, arsenic, antimony, bismuth, manganese, rhenium, aluminum, zirconium, titanium, hafnium, vanadium, niobium, tantalum, tungsten, and molybdenum. Examples of suitable alloys having two metals include, but are not limited to, gold-copper-cadmium, zinc-cobalt, zinc-iron, zinc-nickel, brass (an alloy of copper and zinc), bronze (copper-tin), tin-zinc, tin-nickel, and tin-cobalt.

In some embodiments, the electrolyte comprises metal particles. Deposition of metal particles of a desired composition, crystallinity and crystal structure may provide same or substantially similar properties to the deposited material on the first electrode with less dependence upon specific deposition parameters. Each metal particle brings millions of preformed metal bonds, resulting in proportionality less energy needed from the first current to complete the bonding deposit compared to conventional electrodeposition. The particle volume also dramatically accelerates the bonding deposition rate. At least for these reasons, particle codeposition improves the time and energy efficiency of the methods disclosed herein.

In contrast, conventional electrodeposition is very slow because individual metal atoms must migrate through liquid to the metal surface to deposit, one by one. Without wishing to be bound by theory, when metal particles electrically contact the first electrode, dissolved metal species also deposit on and around the metal particle in brick-and-mortar fashion until the metal particle is completely occluded. Before occlusion, however, the metal particle itself does not chemically bond to the first electrode unless its surface atoms are in a reducible state. As such, depositing molecular species push away the metal particles from the surface instead of becoming occluded. Metal particles that occlude may have trapped electrolyte between them and the surface. This porosity is detrimental to the mechanical integrity of the deposit. As such, conventional electrodeposition rarely occludes more than 10 vol % metal particles.

The composition of the metal particles may match that of the first electrode. Metal particles of two or more elements, such as Al and Fe, may be mixed in a desired stoichiometry to yield an alloy. Mixed metal particles may codeposit an element which is poorly soluble in the electrolyte or for which reduction to a metallic state is outside the electrochemical potential window of the electrolyte. For example, aluminum is molecularly reducible in EMIC, while iron is not. Ceramic or polymer particles may be codeposited with metal particles to obtain deposit properties which are outside the range or alterability of a base metal alone.

Particles of dielectric polymers may be codeposited to modify the dielectric properties of the deposit, or to increase deposition rate without increasing the potential for surface roughness (molecular species deposit around dielectric particles, and atop conductive particles leading to roughness in the case of the latter).

The electrolyte may comprise a metal salt. Any metal salt known within the electrochemical arts is suitable for use in this method.

3. Additives

The electrolyte may further comprises one or more additives, including but not limited to, acids, bases, salts, surfactants, thickeners, buffers, ionizable organic compounds, and fibers. In particular, the electrolyte may comprise thickener to modulate the viscosity and increase the mass of particulates stably suspended in the liquid electrolyte.

In some embodiments, the electrolyte may comprise fibers. Fibers may increase the mass electrodeposited on the first electrode per time per charge applied between the first electrode and source of a counterdcharge. Fibers suspended within the electrolyte may be codeposited with metals at the first electrode to modulate the mechanical properties of the deposited material. Fibers based upon carbon, silicon or other materials may modify the tensile strength, ductility, or other properties.

In other embodiments, the electrolyte may comprise a surfactant. The surfactant, when present, may be sodium dodecyl sulfate (SDS), ammonium lauryl sulfate, or a block copolymer, such as polyethylene glycol. In particular sodium dodecyl sulfate may be mixed with alkali to reduce the adsorption strength between the surfactant and the surface. Alternatively, the ionic sulfate headgroup of SDS may be replaced with sulfamate to achieve this effect without increasing alkali content.

In a polar solutions, concentrations of surfactant above the critical micelle concentration (CMC) result in micelles, which may encapsulate particulates to increase their effective solubility and mass loading, and to insulate suspended particles from the oxidizing effects of water-induced passivation and corrosion. Surfactants may also mitigate dendritic nucleation and growth, resulting in a more even deposition across the first electrode. Surfactants may decrease the first electrode's surface energy and facilitate removal of hydrogen bubbles to avoid pits and pores than can otherwise form in the deposited material. Surfactants may also brighten by inhibiting the buildup of more oxidized species such as $Fe^{+3}$, removing the need for post-treatments normally required to provide a polished surface.

While protecting suspended or dissolved particles against oxidation, a surfactant shell can itself be an energy barrier to electrodeposition. Additional overpotential may be needed to decompose the surfactant so that charge transfer may reach the particle surface. Long and short chain surfactants with electrically conductive backbones may lower overpotentials associated with surfactant.

The range of concentration of additives in the electrolyte can and will vary. Generally the concentration of additives in the electrolyte may rage between about $10^{-2}$ mol/L and about $10^{-5}$ mol/L, such as between about $10^{-2}$ mol/L and about $10^{-3}$ mol/L, between about $10^{-}$ mol/L and about $10^{-4}$ mol/L, or between about $10^{-4}$ mol/L and about $10^{-5}$ mol/L.

When present, the concentration of surfactant within the electrolyte may be much greater than that of other additives. If the additive is a surfactant that can be incorporated into the deposit on the first electrode, the surfactant concentration should be minimized in the electrolyte by balancing the smallest concentration of surfactant with the average chain length of surfactant. Long-chain neutral surfactants are typically more effective at increasing the viscosity of a solution, but may decrease the diffuse mobility of encapsulated particles. Alternatively, short-chain ionic surfactants may increase the diffuse mobility of encapsulated particles, while enhancing the ionic conductivity of the supporting solution.

C. Source of a Countercharge

The methods and devices of the present disclosure may also comprise a source of a countercharge. When present, referring to FIG. 1A, the source of a countercharge may be an electrode counter to the first electrode 110, where the first current 130 is induced between the first electrode 110 and the source of a countercharge 120. As such, the source of a countercharge generally provides an anode for an electrochemical process described herein.

In some embodiments, the source of a countercharge may a non-corroding electrode, which is generally stable during induction of a first current. That is, the non-corroding electrode does not dissolve or release metal into the electrolyte because of a chemical potential between it and the electrolyte, or because of an electric potential between the source for a countercharge and the first electrode.

Suitable examples of non-corroding electrodes include, but are not limited to, Pt, Au, boron-doped diamond, or platinized or gold-coated conductive substrate. Suitable soluble electrodes include, but are not limited to, Fe, Al, Cu, or any other electrically conductive metal, including alloys and composites. Electrodes may be interchangeable to facilitate routine replacement and maintenance and reconfiguration. Although presented here in the context of the source of a countercharge, non-corroding electrodes may also be used as electrodes in other capacities, including cathodes and reference electrodes.

In other embodiments, the source of a countercharge may be a corroding electrode, which dissolves when a first current is applied between the corroding electrode and a first electrode through an electrolyte, thereby suspending the one or more metal species into the electrolyte. Referring to FIG. 1B, a corroding electrode is depicted as a possible source of a countercharge. When the first current 130 is induced between the corroding electrode 120 and the first electrode 110 through the electrolyte 140, metal 122 from the corroding electrode 120 is released as metal species (M$^+$) 124 into the electrolyte 140. Additional metal can be in the electrolyte when the electrode is corroding, for example from metal salts dissolved in the electrolyte. In other instances, the only metal source is from metal species released from the corroding electrode.

In various embodiments, a corroding electrode may comprise one or more metal species selected from the group consisting of metal particles, metal ions, and combinations thereof. Dissolving the corroding electrode releases new metal into the electrolyte, maintaining its concentration through the duration of the method. The metal-carrying capacity of the electrolyte becomes less important because fresh metal can be supplied from dissolution of the corroding electrode. Metal precursors are supplied from the controlled corrosion of a formulated source of a countercharge into the electrolyte near the first electrode.

The corroding electrode may further comprise one or more ceramic particles or dielectric polymers. The corroding electrode may be formed by pressing together metal particles into a solid body. The corroding electrode may be made by any number of thermal, pressure, or chemical synthesis methods. In one instance, the corroding electrode may be made by pressing metal powders into an electrode geometry, such as a rod for gun-feed style applicators, or as a disk-pellet for patch style applicators.

The corroding electrode may comprise one or more sizes and geometries of particles. During deposition, corrosion of the source of a countercharge may occur primarily along the grain boundaries of the pressed particles when higher current densities are used, causing their release into solution with their approximately original dimensions. Particles dissolved in this way are surface activated and exhibit a higher solubility in the electrolyte than particles which are simply mixed into solution. Particles with a surrounding layer of metal-species which is electroactive for deposition, such as $Al_4Cl_7$ in 1-ethyl-3-methylimidazolium chloride (EMIC), are more readily codeposited.

The metal particles may have grain sizes selected to grain sizes of the first electrode. Metal particle size may be small enough to remain suspended in the electrolyte and avoid the effects of gravity or control the impact of grain size on the properties of the deposit. Larger grains result in a harder metal from slower processes. Smaller grains yield softer metal with more ductility from a faster deposition. Grain sizes may be selected to match those of the substrate, helping to increase continuous uniformity between the substrates. The large discrepancy at the grain boundary define points of failure In some embodiments, the metal particles may have rough or non-symmetric dimensions. In other embodiments, the metal particles may have spherical dimensions and a uniform surface energy. In still other embodiments, the metal particles may have an elongated dimension, which aligns with a second current induced across the first electrode, the second current being transverse to the first current, and the second current inducing a relativistic charge across the first electrode.

Without wishing to be bound by theory, rough or non-symmetric particles may be more easily suspended in solution and can be codeposited in higher yield than symmetric particles. Spherical particles with uniform surface energy may codeposit such that the overall finish of the deposit is more predictable and easy to control. Elongated particles may align themselves with the electric or magnetic fields of second current and encourage directional growth, bridging a gap between two first electrodes more rapidly.

D. First Current (Electric Field)

Using the methods described herein, referring to FIG. 1A, the first current (electric field) 130 is an induced current between the source of the countercharge 120 and the first electrode 110 through the electrolyte 140. The first current polarizes the workpiece so that it possesses a net negative charge. This negative charge attaches metals from the electrolyte to effect new metal-metal bonds with metals on the surface of the workpiece.

The first current may be modulated in its power, voltage, amperage, frequency, duration, and other parameters. The first current may be induced using a pulse plating or a reverse-pulse plating scheme, where a pulsed power is applied to sequences of galvanostatic, galvanodynamic, potentiostatic, and potentiodynamic power to the first electrode through the first current. Such pulses may be applied in a repeating sequence.

Shorter pulses of polarization of the workpiece may maintain a relatively stable concentration balance of the metal species at the workpiece/electrolyte interface. Dissolved metal salts and suspended metal particles in an electrolyte have different diffusion rates and require different energies to electrophoresis. As the metal species approach the surface of the workpiece, concentration of metal salts and metal particulate become imbalanced compared to the bulk electrolyte. Because the metal salts diffuse more quickly than metal particles, they reach the surface at a faster rate and are more likely to be deposited. Shorter pulses of polarization allows these metal species to equilibrate during the electrochemical process.

Pulse plating or reverse-pulse plating schemes through the first circuit smoothen the surface and retard deposition. Pulse plating typically uses an on-off pulse rather than a sine wave. The off cycle allows fresh electrolyte to diffuse into features on the workpiece. The on cycle drives deposition onto the workpiece. The primary benefit of pulse plating is that the off-cycles of the pulse allow more time for convection of the electrolyte near the surface. This can restore a more uniform concentration of fresh reactants across the surface despite faster depletion at rough areas during the on cycle. During the ON period, rough areas still experience higher charge density than smooth areas and so the benefit of pulse plating has limitations Sequences of pulses of opposite polarity may increase the adhesion and mechanical strength of deposited metal, by promoting a greater number of metal-metal bonds.

Pulses may include dynamic current or potential ramp rates, for example a pulse applied at about 5 mA/µs from between about 0 mA and about 2 mA, followed by −0.2 mA/µs from between about 2 mA and about 0 mA. Pulses may involve uniform or disproportional changes in polarity, for example a pulse with lower and upper bounds of between about −1.5 V and about 1.5 V, or between about −1.5 V and about 0.7 V. These pulses may be generated from an electroplating power supply, which may be power supply 160, or a reverse pulse rectifier used to generate a DC current for electrochemical processes.

When used, pulse plating occurs over a defined period, such as 1 to 1000 microseconds for aqueous electrolytes. The period may be static, where the same time interval spaces each pulse, or it may be dynamic, where the periods change between each pulse. The length of the period may be longer for electrolytes that are more viscous.

For example, referring to FIG. 3, preprocessing the first electrode may involve positively polarizing the first electrode to corrode the surface of the first electrode into the electrolyte (310). Preprocessing step 310 may then be followed by a negative polarization which electrodeposits more material onto the first electrode than was corroded off in the previous step (320). The negative polarization may then be followed by induction of a second current transverse to the first current of the negative polarization (330). The completeness of the electrochemical process may be assessed (340). If the electrochemical process is not complete, the first current and/or the second current are modulated so the desired material was deposited while assuring superior surface penetration (350). If the electrochemical process is complete, the process is terminated (360). A similar sequence might also continuously corrode and redeposit material from the surface of particles already deposited onto the first electrode. This approach could homogenize the surface and increase bonding across the entire surface boundary of deposited particles. In this way, an initial sequence of pulses may clean the surface of the first electrode.

A final sequence of pulses may be affected to passivate (or pickle) the surface of the first electrode. Electropolishing, when used, may leave the deposited material with the corrosion resistance finish. Pulsed power may decrease the lattice strain and surface roughness of deposited metal. For deposits with thickness around 1 millimeter or more, mitigation of lattice strain is less important because fractures after several micrometers of deposit are eventually filled-in with more material.

E. Second Current (Induced Potential)

Following the methods described herein, referring to FIGS. 1A, 2, and 6B, a second current 150 (which current may be from an induced potential 250) can be applied through and/or across the surface 111 of the first electrode 110 to affect surface electrons 420 and induce favorable properties in the deposit without altering the parameters of the first current 130 the electrolyte 140 or the source of a countercharge 120. The electrons 450 at the surface 111 experience a forward compression and rearward expansion of their electric field. This compression and expansion generates a relativistic charge 112 propagating outward from the electron's center at the speed of light. The relativistic charge then bends the field lines of the first current 130, directing metal from the electrolyte to form new metal-metal bonds on the first electrode.

Viewed in another way, the induced potential bends the field lines proximate the surface such that metal from the electrolyte follows a path of the bent field lines to deposit the metal onto the surface. The bent field lines ultimately intersect the surface, including irregularities in the surface, at 90 degrees within very close proximity to the portion of the surface, being intersected. The field line may intersect at a different angle, but it does intersect the surface somewhere. The difference between a point of deposition under the induced potential and a point of deposition without the induced potential is a shift of the field lines toward crevices and rough areas of the surface not normally filled.

The second current can augment many aspects of electroplating and electrodeposition processes, including, but not limited to, two-dimensional growth (smoothness and uniformity); grain properties, such as crystallinity and morphology; induced nucleation on energetically difficult surfaces; reduced porosity in the metal; adhesion onto the substrate; and controlled linear crystalline growth. Therefore, the properties of the deposited metal can be changed without heat, pressure, or modifying the system's components or normal deposition parameters.

The second current, or transverse current, however, is more than a mere improvement on electroplating or electrodeposition. This is an entirely different current than the first current used to drive metal species to the surface of the workpiece. The results achieved herein using the present electrochemical methods are not possible with conventional electroplating or electrodeposition techniques.

Figure 7:
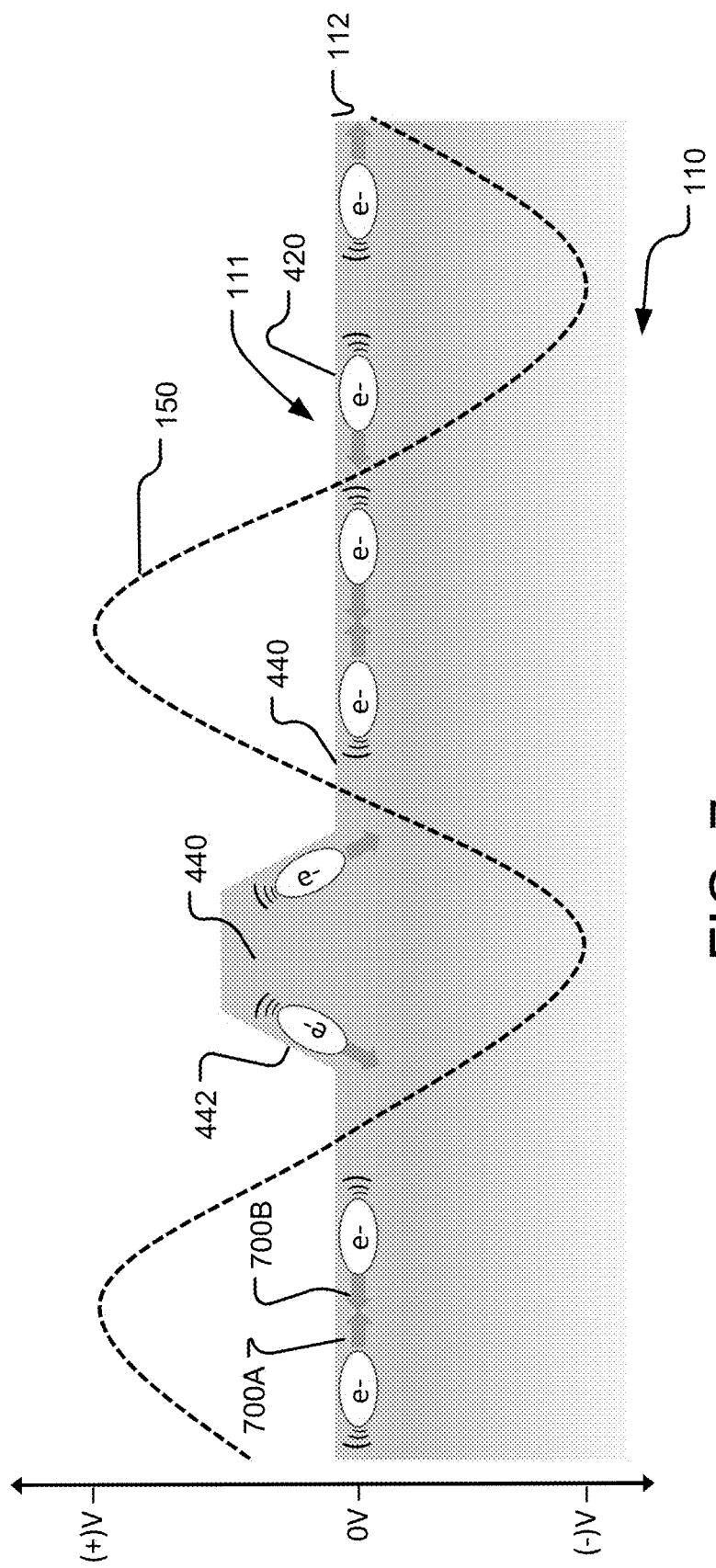
FIG. 7 depicts an electron distribution due to sinusoidal second current 150.

Some benefits of the transverse current are illustrated at FIG. 7. In this example, the second current 150 is in the form of a bipolar, sinusoidal waveform across a surface 111 of the first electrode 110. Absent the second current 150, as in a conventional electrodeposition, the electrons 420 can be considered stationary in all directions running parallel to the surface 111. Without a transverse current, the electrons 420 are considered stationary for purposes of this discussion because, while the electrons are in fact moving, their net movement is relatively slow as per Equation 2, as well as non-uniform as a result of electrode resistivity and electrolyte convective field effects. Thus, no relativistic effect is present. The second current 150 effects a relativistic change 112, causing electrons 420 to move across the surface 111 in directions 700 of the imposed electric field. When the second current ($V_{TC}$) is positive, electrons 420 accelerate toward the right, and toward the left when $V_{TC}$ is negative. This shuffling of the positions of electrons 420 at the surface 111 changes the electron distribution, and therefore, the localized charge density. When the waveform of $V_{TC}$ approaches 0, electrons may be bunched together or pushed apart farther than normal. In the former, a smooth point 430 on the surface 111 may experience the charge density normally seen at points with greater curvature 440. Similarly, the charge density at curved points 440 may be reduced from their normal values.

The second current may be chosen from an alternating current (AC), or a combination of an AC current and a direct current (DC) offset upon which the AC current is imposed. When the second current combines the AC current and the DC second current, the DC second current may offset the AC second current by an amount less than an electrochemical breakdown of the electrolyte.

Figure 8:
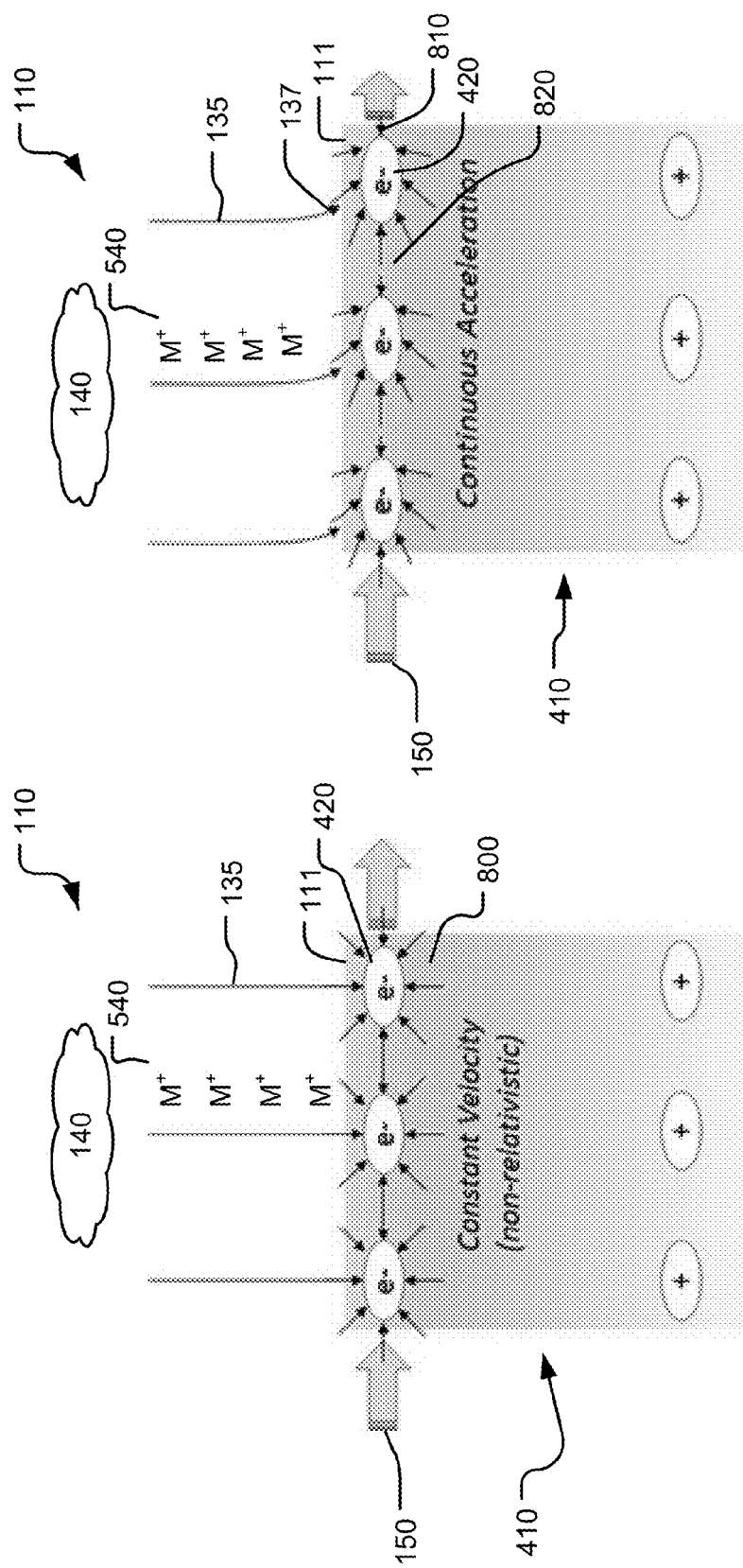
FIGS. 8A-8B depict the effect of a second current 150 on the electric field 135 of a first electrode 110 when surface electrons 420 are moving at constant, non-relativistic velocity (FIG. 8A) and at continuous acceleration (FIG. 8B), thereby imparting a relativistic charge 112.

When DC is used alone, it moves electrons on the surface of the first electrode at a constant velocity, but it does not accelerate them to generate a relativistic charge at the surface. As shown in FIG. 8A, electrons 420 moving at constant velocity maintain uniform spacing and constant electric field vectors. A DC offset second current 150 applied to the first electrode 110 causes a net flow of electrons at a constant velocity in the bulk and surface of the first electrode 110, thus inducing a magnetic field at all depths. The bulk fields cancel, while surface fields propagate outside the conductor. Consequently, a DC offset second current only weakly impacts the electric field lines 150 from cathodic polarization of the first electrode 110 under the first circuit 130.

With constant velocity electrons, their electric fields are contracted tangential to the surface, and a field intensity increase in the perpendicular directions, following the Liénard generalization:

$$\gamma \equiv \frac{1}{\sqrt{1-\frac{v^2}{c^2}}} \qquad \text{(Equation 1)}$$

where γ is the contraction constant, v is the velocity of the electron, and c is the speed of light ($3 \times 10^8$ m/s). Here, the electron velocity is non-relativistic, so the degree of this effect is small.

When the AC second current is used, however, regular or constant charge acceleration is induced (FIG. 8B). Under acceleration, electrons experience a forward compression 810 and rearward expansion 820 of their electric field, which propagates outward from the electron's center at the speed of light. The term "relativistic charge" refers to this constant acceleration at or near the speed of light at the surface of the first electrode. Before now, electron acceleration and its effects had not been explored in electrochemical processes.

Referring again to FIG. 8A, electric field lines 135 due to cathodic polarization of the first electrode 110 are normal to the tangential point of the surface 111 due to the symmetry of the electron's electromagnetic field. When the electron's electromagnetic field is no longer symmetric due to movement of the charge, the polarization field lines are proportionately shifted (137, FIG. 8B). Metals in the electrolyte (M$^+$) flowing to or from the first electrode 110 follow the paths 135 of these polarization field lines. The field-shifting effect using second current 150 may be maintained for periods similar to the diffusion rates of ionic reactants and the reaction kinetics.

When the workpiece has a void, the second current may have a DC offset to introduce a potential drop within the void. When two workpieces are not in electrical contact, the DC offset is applied with consideration to the electrolyte stability. Most electrolytes have a window of stability around +/−6 V. If the workpieces are in electrical contact, the DC offset can be much greater without damaging the electrolyte, because the current can complete a circuit without depending entirely upon charge pass through the electrolyte. The electrical contact need not be within the area targeted for deposition, and the DC offsets can be much more than +/−6 V, including up to +/−200 V. Gap geometry may also affect the limits of the DC offset.

The strength of this electric field, V/m, may be stronger than the electric field of the first current to reroute metal ions from the first current into the void. The DC offset may correlate to the voltage at root-mean-square ($V_{RMS}$) or the current at root-mean-square ($I_{RMS}$), while the voltage peak-to-peak (Vpp) or the current peak-to-peak (Ipp) may be bipolar. This DC offset leads to transverse growth inside the void, and also to the formation of metal-metal bonds within the gap. When the overpotential of deposition is greater, adhesion is often improved. In general, $E_{TC}$ can be much greater than $E_{ED}$, if the workpieces being joined already have some point of electrical contact. On the other hand, greater overpotential can also increase grain size of the deposition metal, which can harm adhesion, depending on the system.

The first and second currents may be modulated together so that the positively biased first electrode continues to experience a positive current efficiency and positive net mass gain; i.e. so that the direction of the first current does not invert, and the first electrode does not become the source of a countercharge. Also, the second current can be separately modulated so that a bottom-up growth occurs inside the void, a phenomenon unknown in conventional electrodeposition without organic additives (e.g., levelers).

The conductive and dielectric behavior of metal particles in the electrolyte may affect whether the second current affects electrophoretic ($F_{EP}$) or dielectrophoretic ($F_{DP}$) forces. For example, for a 10-μm dielectric particle the electrokinetic field force imparted can be up to 5 orders of magnitude stronger than that that felt by a conductive particle of the same size. For 10-nm particles, the situation is reversed. Both are frequency-dependent and particle velocity may be based on how much energy can be stored in an ionic cloud surrounding the particle (that is, the "permittivity"). As frequency increases into the kHz range, that energy usually decreases substantially.

By reducing the stored energy between the metal particle and the first electrode, particle riding and occluded porosity are reduced. Without wishing to be bound by theory, as the metal particle approaches the surface of the first electrode, the energy stored in the electrochemical double layer tangentially distributes. $E_{TC}$ starts to compete with $E_{ED}$. Thus, the double layer barrier between the metal particle and the surface of the first electrode is reduced. The electric field also imparts an electrokinetic velocity tangential to the surface, which causes parallel wobbling as the particle approaches the surface perpendicularly. Both mechanisms reduce the porosity of deposits created with particle occlusion following the methods described herein.

F. Waveform

The second current (or induced potential) is a periodic or non-periodic waveform, such as a sinewave, a triangle wave, a sawtooth, as well as any number of other possible waveforms, and combinations thereof. Each type of waveform imparts a perturbation to surface charges. Several waveforms may also be combined to define the second current, or induced potential.

Figure 9:
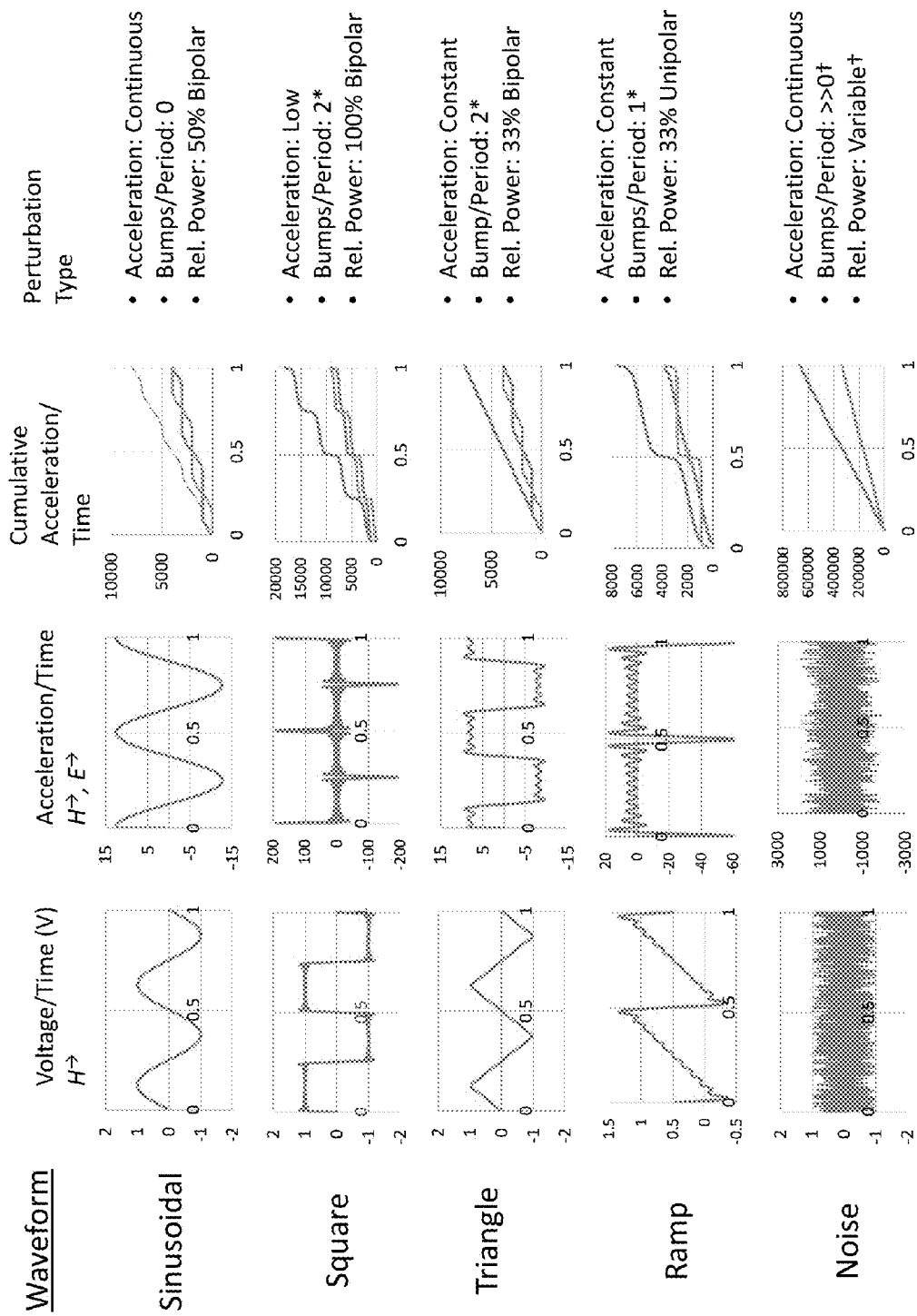
FIG. 9 depicts the properties of idealized waveform variations at 2 Volts peak-to-peak (Vpp) and 2 Hz over two periods. These variations do not account for impedance. (*) The minor bumps depends upon the harmonics and waveform integrity produced by the signal generating equipment. (†) Noise has no true period/frequency, and the actual properties depend heavily upon the signal generating equipment and type of noise.

FIG. 9 illustrates examples of the most common fundamental waveforms and their properties used in the present method. The waveform and its variable parameters (current, voltage, frequency, and duration) may be controlled to affect the second current. Waveforms induce a potential across the surface of the first electrode to move charges across the first electrode. Without wishing to be bound by theory, constant voltage over time causes charge to move in a set vector. Charge movement then induces an electric field between gaps or rough features on a first electrode, and induces a magnetic field, H$^\rightarrow$, at the surface of the first electrode. Changing voltage over time causes a proportionately continuous acceleration of charges, which induce both magnetic and electric fields (H$^\rightarrow$,E$^\rightarrow$) at the surface. A "bump" is an abrupt change in the vector of a charge, such as the apex of a triangle wave (directional bump) or a polarity change (polarity bump). Both appear in FIG. 9 as slews or asymptotic points. "Relative power" describes how different waveforms of identical peak voltage deliver power across the electrode surface. In electrochemical processes, voltage may be treated as a constraint instead of a power, because potential is thermodynamically significant to the reaction, while power relates to time and surface area.

The applied waveform may be formed from a combination of numerous waveforms based on harmonics of one or more frequencies at which the electrolyte or the first electrode exhibits absorption of the one or more frequencies. The second current (or induced potential) may have a period similar to a diffusion rate of a component in the electrolyte.

A power source may apply a waveform as a time-dependent voltage built from the superposition of multiple sinusoidal signals (analogue harmonics). Some waveform generators may increase the number of harmonics to reduce the magnitude of perturbations in the waveform. Even when $V_{peak}$ is tens of volts, a superimposed perturbation of a microvolt can affect the second current. A noise signal is composed primarily of bumps and no repeating periods of constant charge velocity or acceleration. Noise with the same $V_{peak}$ as a sinusoidal waveform will deliver more electromagnetic radiation (EMR) than a sinusoidal waveform at 2 Hz. Sinusoidal frequency of sinusoidal signal in one example, may be 20 Hz at 2 Vpp, or 10 Vpp at 2 Hz, to provide roughly the same EMR, as the 20 Hz signal, without accounting for effects from the radiating body, such as gain and resistance.

When a second current is applied across the first electrode, electrons move across the surface of the first electrode with a net velocity toward the electric field. This material-dependent speed, called "drift velocity," $v_D$, is between about mm/s and about μm/s:

$$v_D = \frac{I}{n*A*Q} \quad \text{(Equation 2)}$$

where I is current (amperes), n is the volumetric charge carrier density in the medium (e⁻/m³), A is the area of flux (m²), and Q is the charge of the carrier ($1.6 \times 10^{-19}$ C/e⁻). An electron at a constant velocity has its electric field contracted tangential to the surface of the first electrode, and has its field expanded perpendicular to the surface, per the Liénard generalization. The distortion is negligible if v<<c, as for $v_D$. Therefore, constant electron velocity from second current is limited on the surface of the first electrode compared to the effects of acceleration.

At frequencies below kHz, impedance can be ignored. Ohm's law determines current flow based upon the voltage/time curves of a waveform. For a real-world first electrode, $v_D$ through the first electrode depends heavily upon geometry and, therefore, will be non-uniform across the surface.

Charge produced by electron acceleration propagates across the first electrode relativistically, at close to the speed of light, much faster than $v_D$. Under the AC second current, the average $v_D$ is 0, while the velocity of propagation is approximately:

$$v_P = \frac{c}{\sqrt{k}} \quad \text{(Equation 3)}$$

where k is the dielectric constant of the material in the electrolyte. Since charges move on the surface of the first electrode and not within its bulk, the signal propagation produced by second current moves along the first electrode-electrolyte interface. So the dielectric constant of the electrolyte also affects the velocity of propagation. For example, water has a dielectric constant of 80.4; $V_P$ is still $3.35 \times 10^7$ m/s, dramatically faster than mass transport through the electrolyte.

The power of the EMR of a moving particle can be approximated using Larmor's equation:

$$P_{e^-} = \frac{\mu_o * Q^2 * a^2}{6 * \pi * c} \quad \text{(Equation 4)}$$

where $\mu_o$ is the permeability of free space ($4\pi \times 10^{-7}$ N/A²) and α is the charge acceleration, a reasonable approximation when drift speed is much slower than the speed of light.

Absent the second current, a charged particle radiates an electromagnetic field, which dissipates with distance, r, from its center as $\geq 1/r^2$. In contrast, the electromagnetic field of the same particle in motion dissipates as about 1/r. Thus, the electromagnetic field of electrons under second current is much stronger, per Coulomb's Law:

$$E_r = \frac{q}{4*\pi*\varepsilon_0*r^2} \quad \text{(Equation 5A)}$$

and $$E_\theta = q*\alpha*\frac{\sin(\theta)}{4*\pi*\varepsilon_o*r*c^2} \quad \text{(Equation 5B)}$$

where $E_r$ is the electric field which is radial in all directions to the point charge, $E_\theta$ is the electric field which is perpendicular to $E_r$, and $\varepsilon_o$ is the permittivity of free space ($8.85 \times 10^{-12}$ C²/Nm²). $E_\theta$ is unique to charges under acceleration and is responsible for the effects of second current on the electrodeposition. $E_\theta$ is negligible for charged particles at non-relativistic velocity and no acceleration.

EMR depends on the acceleration and not the velocity of the electron, and acceleration depends on frequency of the applied waveform. Equally dependent is the power available at the first electrode/electrolyte interface. The power supplied for sinusoidal second current can be described by:

$$P_{TC} = \tfrac{1}{2} * R_{peak} * |I_{peak}|^2 = P_{rad} + P_{ohm} \quad \text{(Equation 6)}$$

where $R_{peak}$ and $I_{peak}$ are the peak resistance and current of the waveform, respectively. $P_{TC}$ can be divided into radiated power ($P_{rad}$) and power dissipated due to ohmic losses ($P_{ohm}$).

AC second current increases bulk resistance and channels more power to the surface of the first electrode where the resistance is less. This phenomenon is called the "skin effect":

$$S_D = \sqrt{\frac{1}{\pi*f*\mu*\sigma}} \quad \text{(Equation 7)}$$

where f is the frequency, μ is the permeability of the electrode, and σ is its conductivity. $S_D$ describes the approximate depth from the surface of the first electrode, at which $P_D = P_{TC}/e$. The AC second current, especially at higher frequencies above 1 GHz, more efficiently uses the second current power.

The roughness may exceed the calculated skin depth at ≥1 MHz frequencies. The result of such roughness is a change in the vector of $v_D$ on the first electrode and an attenuation of the EMR traveling according to $v_P$:

$$Y_{RMS} = Y*\left(1 + \left(\frac{2}{\pi}\right)*\tan^{-1}\left(1.4*\left(\frac{R_{RMS}}{S_D}\right)^2\right)\right) \quad \text{(Equation 8)}$$

where $Y_{RMS}$ is the modified attenuation constant of the electrode due to roughness, Y is the original attenuation constant of the material, and $R_{RMS}$ is the RMS roughness. This relationship under Hammerstad model demonstrates increased attenuation from roughness by unity for the smoothest surfaces and by double for the roughest surfaces. Power dissipation results from micro-field formation between roughness features, and can be absorbed by interfacial electrochemical processes. With the appropriate waveform, fields from the second current affect the first, secondary, and tertiary electric fields at curvature. Thus, the frequency of the second current may be determined based upon the skin depth of the applied power. Generally, the transverse current causes a more uniform micro-current and macro-current distribution.

EMR occurs at the first electrode/electrolyte interface per $P_{e-}$ and radiates away from the surface per $v_P$. The energy from 0 to some distance, $R_{NF}$, from the interface is both radiative and reactive:

$$R_{NF} \le 0.62 * \sqrt{\frac{D^3}{\lambda_{TC}}} \qquad \text{(Equation 9)}$$

where D is the maximum dimension of the electrochemically active first electrode or the distance between the electrodes applying second current, and $\lambda_{TC}$ is the wavelength of the second current. This region is the reactive near field and within it, $E_\theta$ and $E_r$ are in-phase with the magnetic field of the EMR. As energy interchanges between $\vec{E}$ and $\vec{H}$ every quarter period, the electric fields exhibit capacitive behavior, while the magnetic field exhibits inductive behavior. Within the near field region, electrochemical polarization field lines and any ionic species in the electrolyte reacting with them are subject to these frequency-dependent capacitive and inductive fields.

Another consideration is that the waveform period determines the slew rate and, therefore, the potency of 10 μVpp compared to 10 Vpp (FIG. 9). Without wishing to be bound by theory, the effect of the electric field induced by second current over an area may depend upon the gradient of the field over the area, or the "slew rate," $\Delta V/\Delta x$. (x may be the space or time domain.) Although their peak magnitudes perpendicular to the surface are never the same, a high potential, low frequency waveform may have the same slew rate as a low potential, high frequency waveform at certain points or times, particularly at a bipolar bump. At very high frequencies even sinusoidal features may appear asymptotic.

Phase-offset is another controlled variable, which could tune the effect of second current across the first electrode. For example, two equal, sinusoidal waves phase-offset by 170°-180° mostly cancel each other throughout the signal-generating circuit. The second current power is stronger at rough and/or asymmetrical areas due to less cancellation, having a localized effect on simultaneously occurring electrodeposition. Once deposited material has filled in the abrasion and restored symmetry to the first electrode, the second current power self-cancels in that area. If cancellation increases substantially before surface imperfections have been removed, a larger phase offset may be applied. A benefit of using superimposed signal cancellation reduces the far-field radiating power from the first electrode, compared to a single second current with large power and a complex waveform.

Each component of the devices described herein facilitates charge transfer at different rates. If the AC frequency is too fast, slower processes may be unaffected. Likewise, slower AC frequency does not affect processes which occur over drastically faster periods. Second current frequencies of about Hz and about kHz can impact ionic displacement reactions, such as ionic reactants in the electrolyte. Faster frequencies may alter the cathodic polarization field lines at about the $v_P$, but the reactants move too slowly to respond to those changes simultaneously and will instead respond with some degree of probability. Frequencies between about kHz and about MHz are timed to the rotational moment of polar molecules. Above about 100 MHz, many aqueous electrolytes cease to conduct and instead behave capacitively. Arbitrary waveforms, such as superimposing a high frequency waveform over a lower one, balance these effects. Such waveforms can be defined by variables modified during an electrochemical process in response to changes in the system (feedback loop). For example, an adequately enabled oscilloscope may monitor the second current to observe phenomena or gradual changes during an electrochemical process to troubleshoot, refine signals, or give sensory feedback (phase shift, attenuation, etc.).

G. Applications of the Method

The methods described herein may be applied to a variety of electrochemical, metal deposition, and metal bonding applications, including corrosion, electropolishing, and the electrochemical processes within batteries.

1. Corrosion Processes

Most corrosion processes are an unintentional consequence of a material's reactivity with its immediate environment. Boats, oil rigs, and other vessels regularly exposed to saltwater constantly corrode due to localized potential differences. Metals contacting other electrolytes, such as metal tanks storing strong acids, or metal pipes containing mineral-rich water. The metal slowly corrodes into the electrolyte, leading to electrolyte contamination, and structural deterioration of the metal component. Steel frame buildings, ships, oil rigs, tanks, pipes, and other structures with large dimensional aspect ratios can experience an induced potential drop across the surface from electrolyte flow. Potential differences between the metal and electrolyte and potential differences between adjacent metals (Cu, Zn, and Fe) are present regardless of electrolyte movement.

To avoid unwanted corrosion, a negative potential is sometimes applied to the entire structure to maintain the structure at a DC electrical potential below the corrosion potential. This method is referred to as "impressed current cathodic protection", or "ICCP." While ICCP reduces corrosion, its effectiveness is limited by the placement of nearby anodes. The overall effectiveness of ICCP could be enhanced by a method that better distributed charge across a vulnerable surface. Alternatively, in situation when anodes cannot be placed appropriately, a transverse current can be more effective By using a method described herein, a second current may reduce corrosion at a junction between two or more galvanically reactive metals (such as Cu wire on Zn-coated Fe in saltwater). No first (deposition) current is used in this example. Under these conditions, the second current can distribute the charge away from grain boundaries on the surface of the first electrode, avoiding corrosive pitting at that surface.

2. Electropolishing

Conventional electropolishing is a type of corrosion process in which a positive potential is applied to a surface to corrode away rough features and render a smoother surface. Advantageously, rough areas corrode faster than smooth. Because conventional electroplating produces unwanted roughness, electropolishing is often used after conventional electroplating to remove accumulated roughness and provide a smooth finish. Electropolishing current densities are usually low and/or pulsed. This maintains a smooth finish at the expense of overall process time. When higher current density is applied, corrosion occurs more rapidly along grain boundaries of the metal, causing chunks of metal to detach from the bulk of the surface and increasing surface roughness.

By using a method described herein, the second current better distributes current. Higher current densities may be run while avoiding the surface corrosion in chunks and along grain boundaries. That is, electropolishing yields a nearly smooth surface by corroding away the edges and rough features without the spalling seen in prior art methods. A DC field may be applied in the opposite direction of the electric field needed to promote electrodeposition. With the methods disclosed herein, electropolishing may be accelerated.

3. Batteries

Also provided herein are methods for charging and healing an electrochemical cell, such as a battery. These methods suppress and reverse dendritic growth, a common source of failure for most batteries.

Batteries generally comprise repeating units of sources of a countercharge and first electrode layers separated by an ionically conductive barrier, often a liquid or polymer membrane saturated with an electrolyte. These layers are made to be thin so multiple units can occupy the volume of a battery, increasing the available power of the battery with each stacked unit. As these components become thinner, they also become more fragile. Further, as the electrodes become thinner, a larger ohmic drop occurs across the surface leading to less uniform charge density during charge/discharge cycles.

For example, lithium batteries typically have a metal oxide electrode (M is typically iron, cobalt, manganese), and a carbon electrode coated on metal current collectors. The metal oxide is added to stabilize the lithium metal. The metal oxide electrode starts as MA and the carbon starts as atomic Li-infused graphite. During discharging (that is, normal use of the battery to provide power to a device), the $Li^+$ ions travel from the carbon through the membrane and intercalate into the $M_xO_y$ to become $LiM_xO_y$. During charging, the $Li^+$ ions follow the opposite path and instead intercalate into the carbon. Under ideal conditions, every $Li^+$ ion finds a vacant $Fe_xO_y$ site or carbon site, and not sites where another $Li^+$ ion has already been absorbed. Problems arise if the $Li^+$ ions try to deposit atop more $Li^+$ and 3D deposits of $Li^0$ start to form. $Li^0$ aggregation creates an explosion hazard and causes roughness. Specifically, if the $Li^0$ reaches the opposite electrode, the battery may short and the dendrites formed during the $Li^0$ deposition may damage the membrane dividing the two half-cells of the battery.

With subsequent charge/discharge cycles the lithium tends to deposit with increased roughness. Commonly dendrites form which puncture or irreversibly damage the electrolyte membrane. If dendritic growth reaches the opposing electrode, then the battery is permanently shorted and cannot be recovered.

As batteries become smaller with increased power capacity these issues have been amplified and pose significant design constraints. The lifetime and performance of batteries with lithium or any other chemistry can be greatly prolonged by increasing the smoothness and uniformity of metal charge carrier species during dissolution and deposition. Additionally, the rate of recharge could be increased without compromising the lifetime of the battery as is the case with conventional batteries.

The methods as described herein provide a means of increasing charge homogeneity on electrodes with significant ohmic drop. This reduces thermal gradients and hot spots, which would otherwise cause exothermic battery failure. Further, this would reduce the performance deviations among individual batteries in a stack that occurs as batteries individually age and degrade at different rates. This configuration is different for every battery system type.

II. Device

Figure 10:
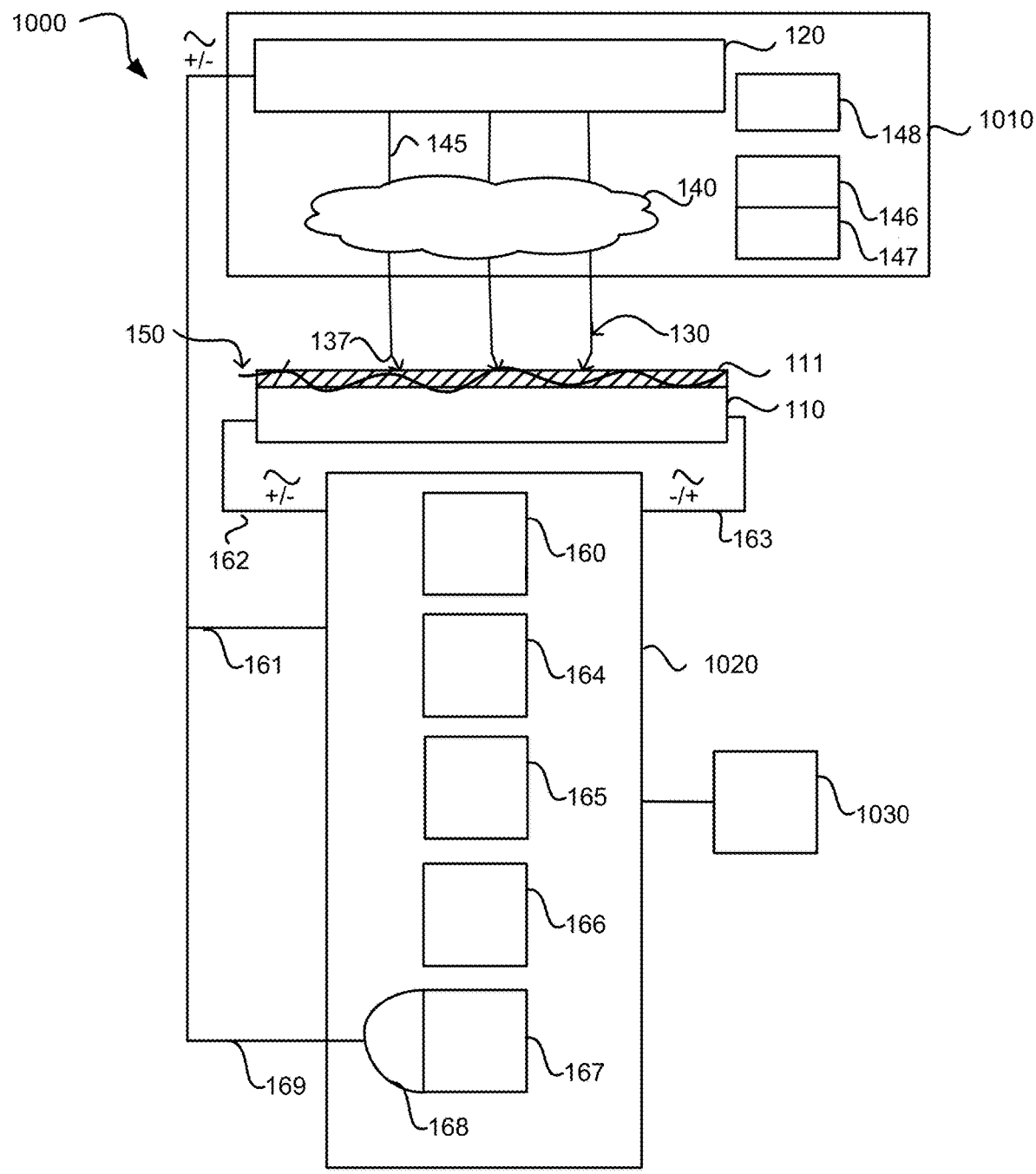
FIG. 10 depicts device 1000 having a main control unit (MCU) 1020 and an electrode applicator unit 1010.

The present disclosure also provides a device for performing the methods described herein. As shown in FIG. 1A and others, the device 100 comprises a source of a countercharge 120 and a first electrode (e.g., workpiece) 110—although the workpiece is a temporary part of the device. The source of countercharge 120 and the first electrode are 100 in electrical communication through an electrolyte 140. The device 1000 includes a current generation source, such as power supply 160, to induce a first current 130 between the source of a countercharge 120 and the first electrode 110 through the electrolyte 140. As such, the current source includes a connection to the source of a countercharge 120 and the first electrode 110. The current source, or another source, also is connected to the electrode to induce a second current 150, sometimes referred to herein as a "transverse" current, across the first electrode. The second current 150 is transverse or otherwise across the first current 130 at the first electrode 110. The second current 150 is controlled to induce a relativistic charge across the first electrode. Referring now to FIG. 10, the present disclosure further provides a device 1000 having a main control unit (MCU) 1020 and an electrode applicator unit 1010. The MCU 1020 contains a power supply 160 and a power modulator 165, which induce a first current 130 between the source of a countercharge 120 and the first electrode 110 through the electrolyte 140. The MCU 1020 also supplies power to induce a second current 150 through a surface 111 of the workpiece 110. The electrode applicator unit 1010 contains at least one source of a countercharge 120 and a plurality of channels 145 for flowing an electrolyte 140 through the electrode applicator unit 1010. The electrode applicator unit 1010 is connected to the main control unit 1020 through a current collector cable 161 connected to the main control unit 1020 and a power control unit 1030 connected to the main control unit 1020. The power control unit 1030 applies a first current 130 between a first electrode 110 and the at least one source of a countercharge 120 through the electrolyte 140. The power control unit 1030 may also induce a second current 150 across the first electrode 110. As described elsewhere herein, the second current 150 is transverse to the first current 130, and may be controlled to induce a relativistic charge across the first electrode 110.

Figure 12A:
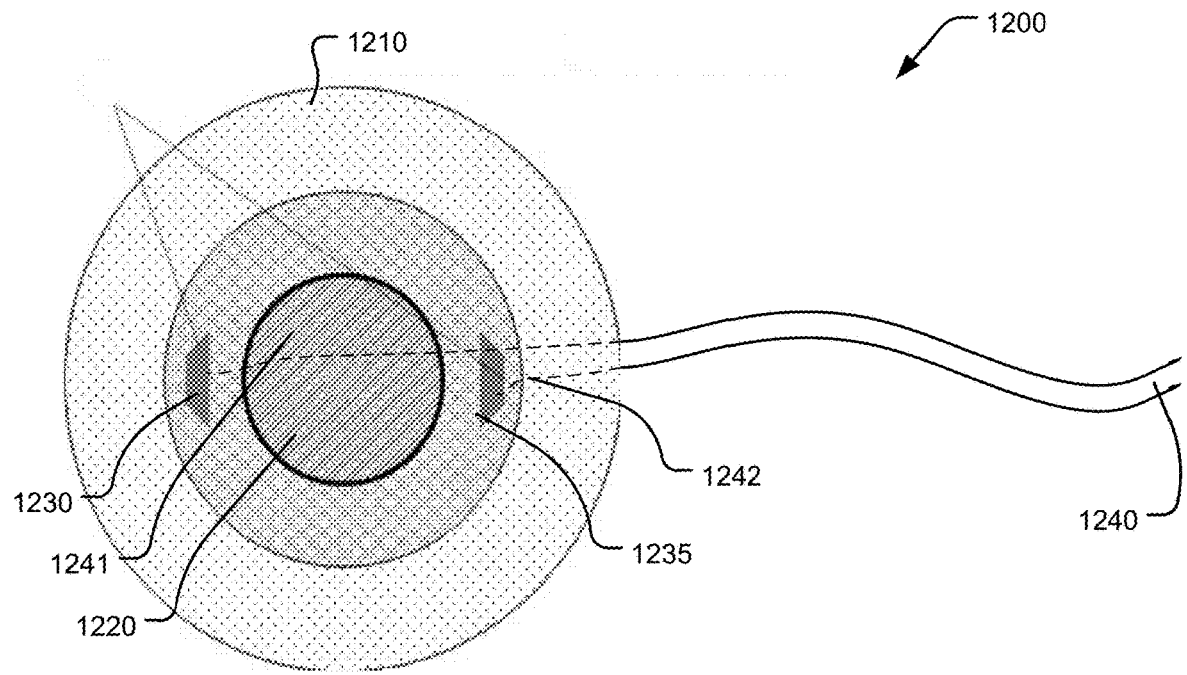
FIGS. 12A and 12B depict a patch-type applicator 1200 from a top view (FIG. 12A) and from a side view (FIG. 12B), as an embodiment of an electrode applicator unit 1010.
Figure 12B:
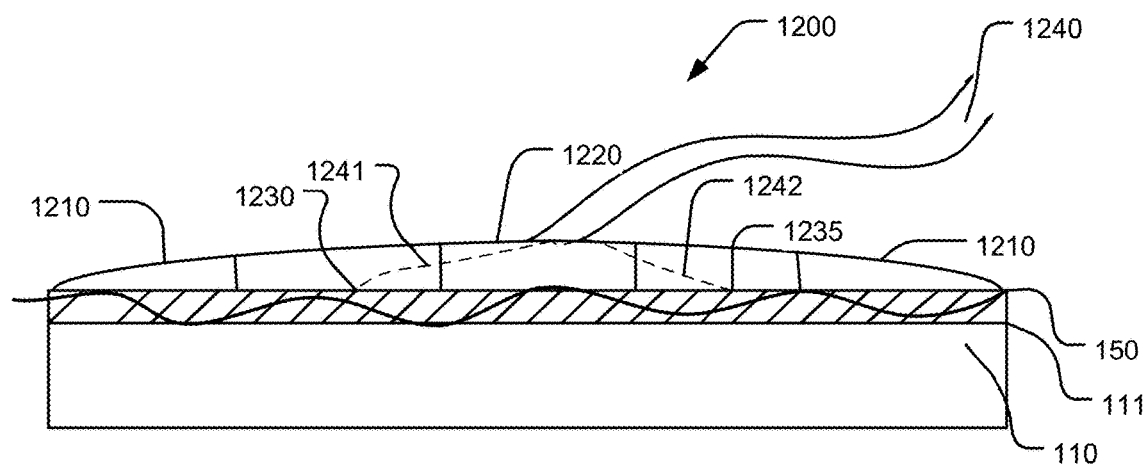
Figure 13:
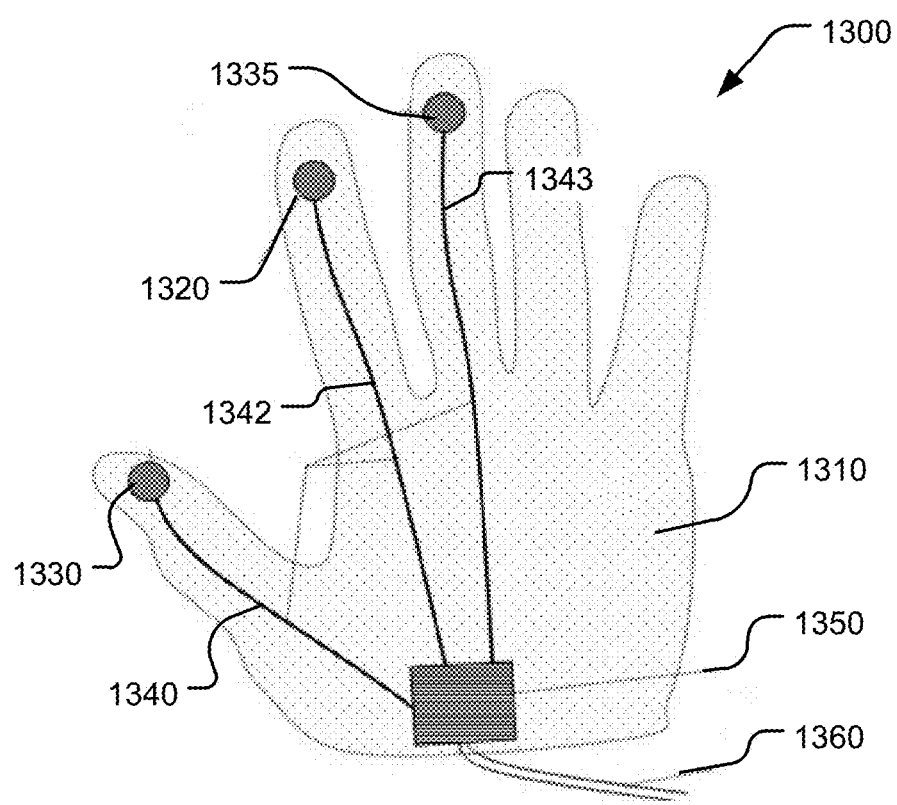
FIG. 13 depicts a glove-type applicator 1300, as an embodiment of an electrode applicator unit 1010.

For a bonding system, one or more applicators 1010 supply new material and supply current to the first electrode, as shown generally at FIG. 10 and in various alternative embodiments at FIGS. 11-13. The applicator 1010 may comprise several contacts for the first current 130 and the second current 150, channels 145 for fluid flow of the electrolyte 140 through the body of the applicator 1010, and auxiliary electrical components. The applicator 1010 may have an integrated heating 146 and/or cooling unit 147, or more generally a temperature control unit, which control the temperature of the electrolyte 140 within. The applicator 1010 and the MCU 1020 may be connected by wiring 161 for power and sensors, and tubing 169 that allows fluid to flow from one to the other.

The device 1000 may further comprise a current collector cable 161 connected to the MCU 1020 via wiring, with leads for attaching to the first electrode. Under operating conditions, the substrate 110 becomes the working electrode.

The device 1000 may further comprise a power control unit 1100, which supplies power for the first current 130 and the second current 150.

The devices may use any electrolyte described herein. The electrolyte 140 may be stored in a tank 167 near, on or within the MCU 1020. When present, the tank 167 supplies the electrolyte 140 to the applicator 1010. A pump 168 drives electrolyte 140 from the tank 167 through tubing 169 to circulate electrolyte 140 within the applicator 1010. In such a configuration, the electrolyte 140 may be dispensed through the applicator 1010. Alternatively, the applicator 1010 may contain a reservoir or tank 167 for storing the electrolyte 140.

A. Main Control Unit

Referring to FIG. 10, the main control unit (MCU) 1020 may house a power supply 160, computer and software 164, computer-controlled power modulator 165, and auxiliary electronics 166. In the main control unit 1020, the computer 164 may execute instructions stored on a computer readable medium. The power modulator 165 and the power supply 160 may be controlled by the computer 164. In some embodiments, the main control unit 1020 may further comprise an electrolyte storage tank 167, a pump 168, and tubing 169 connecting these components together. Here the electrolyte 140 flows from the electrolyte storage tank 167 through the tubing 169 into the plurality of channels 145 of the electrode applicator unit 1010.

The MCU 1020 may comprise one or more additional electrical components, such as a first control system, power generation subsystem for deposition/corrosion, power generation subsystem for the second current, and sensor-based feedback subsystems. When present, the first control system accepts user input for the chemistry and operating conditions and to control the subsystems to provide power for first and second currents. The first control system may be digital for complex systems, or analogue for simple systems with fewer chemistry requirements. Computer control may be used for the broadest range of materials, sensory feedback, data recording, and complex deposition conditions.

The deposition power subsystem must have stable mA and mV control with low internal reflection. The subsystem may provide DC and AC power between about 1 Hz and about 1 kHz. The subsystem may be programmable to apply voltages relative to sensor input from a sensor subsystem. The current may range between about 0 mA/cm$^2$ and about 300 mA/cm$^2$ per channel relative to the area of the first electrode for a given application. Multiple channels and/or fast switching may be used when needed, such as when joining two portions of a first electrode, or when the MCU 1020 controls bonding at multiple areas.

The deposition power subsystem may apply power with modulated first current. Current-controlled power may achieve a current density (A/cm$^2$), and consequently, a desired mass flux from metal of the electrolyte onto the surface of the first electrode. Potential-controlled power may be applied to achieve a redox state of substrate atoms at the first electrode/electrolyte interface. For example, a slightly negative potential could be applied to the first electrode to ensure a metallic state of the surface atoms and to prepare the surface for adhesion. Potential control of positive polarity at the first electrode may corrode the surface of the first electrode. For example, the MCU 1020 could effect a potential equal to or greater than 0.8 V but below 1.6 V vs. a standard hydrogen electrode (SHE) to corrode a steel surface without corrosively pitting. This would be useful for increasing the penetration depth of subsequently deposited layers on the surface of the first electrode without causing significant roughening. Potential control may also control the stoichiometry of deposited alloys or composites via potentials of the first current of based on the metal from the electrolyte.

For example, in an ionic liquid electrolyte containing both Fe and Mn species, the MCU could effect a potential of −0.3V vs. Fe/Fe' for 2 s followed by −0.9 V vs. Fe/$^{Fe+}$ for 2 s. The first potential surpasses the activation energy for Fe to deposit, but is insufficient to drive Mn deposition. The second potential exceeds the activation energy of Mn$^0$ formation and so both species electrodeposit simultaneously. The overpotential (that is, the potential applied in excess of the activation energy) impacts the relative deposition rate of each species.

The MCU 1020 can apply DC or AC and obtain feedback measurements which allow the computer to modulate outputs. For example, the power control unit (PCU) 1030 might operate in a DC mode to measure the open circuit potential (OCP) between the first electrode 110 and source of a countercharge 120 so that potentials may be applied relative to the OCP. The MCU 1020 can also use DC current to measure dynamic capacitance of the electrochemical double layer at the surface of the first electrode. Because the double layer capacitance may proportionately indicate changes in the surface area 111 of the first electrode 110 during operation, such a reading may allow the MCU 1020 to alter the second current 150 or to maintain the current density (A/cm$^2$) specified as new material is added to the first electrode 110. AC can be applied by the MCU 1020 to obtain resistance/impedance measurements. For example, the MCU 1020 can rapidly apply an AC of 1-100 mV and a frequency less than or about 100 kHz to measure the linear impedance response and obtain feedback about the bulk conductivity of the first circuit. If a reference electrode 148 is present in the applicator 1020, additional lower frequencies can monitor the first electrode/electrolyte interface.

The MCU 1020 may periodically interject these modifications into a deposition sequence to obtain feedback. The computer 164 may compare this feedback to models and user-specified operating parameters to modulate the applied power driving deposition and second current.

For example, after 1,000 corrosion/deposition pulse iterations (or every several seconds), the MCU 1020 may superimpose a 10-mV, 500-kHz sinusoidal AC wave onto the DC potential of the preceding pulse of the first current 130 to measure system impedance. The measurement time would depend on the frequency and the number of wave periods recorded and the processing time for the computer to analyze the recorded signal against the applied waveform (~10-50 μs total). If impedance has increased relative to the last data point collected, the computer 164 may determine whether this increase correlates with an expected gradual loss in ionic conductivity of the electrolyte with use and time. If so, the current/potential magnitude of subsequent pulses may be increased to overcome the additional ionic resistance of the electrolyte 140. The entire sequence may be repeated using updated parameters. If not, then the MCU 1020 measures impedance/capacitance at one or two lower frequencies to probe the condition of the surface. Additionally, immediately after the user turns on the power, and again immediately after power is turned off, the MCU 1020 may measure the OCP of the system to estimate the redox state of the first electrode surface 111.

When present the second current power subsystem may have multiple channels with variable output impedance, wideband frequency range (0-GHz), DC offset capability, and waveform generation. Internal amplification and attenuation enables an MCU for larger work areas and may apply µV or smaller perturbations. Separate channels may modulate their output signal relative to one another.

Sensor power subsystems, when present, may allow for processing of feedback/feedforward from electrodes for parameters such as reference, pH, conductivity, signal impedance and attenuation, and whether or not an electrode is contacting the surface of the first electrode. They must also process feedback from temperature sensors and provide power for tip chamber heating when needed. These systems provide feedback to the first control system so that it can modulate deposition and second current circuits.

The MCU 1020 may have an onboard interface, or connect to external computers for programming through separate software. Any device described herein may also further comprise a signal canceler to reduce a far-field radiation from the first electrode.

B. Applicator

Referring now to FIGS. 10-13, many designs can be used for the electrode applicator unit 1010 (FIG. 10), including a gun-type applicator (FIG. 11), a patch-type applicator 1200 (FIG. 12), or a glove-type applicator 1300 (FIG. 13). Generally, the applicator 1010 may comprise at least one ionic contact with the first electrode 110 via a complete circuit 130 between the source of a counterchage 120 and electrolyte 140. Many variations are envisioned within this general design, including, but not limited to, one or more points of electrical (non-ionic) contact with the first electrode 110 in spatial proximity to the point of electrical contact, a reservoir 167 of sufficient volume to contain and dispense electrolyte, a corroding electrode, a source of a counterchage 120, a reference electrode (RE) 148, and a longitudinal receiving antenna that would allow for z-axis amplitude electromagnetic inputs and feedback modifications for the second current 150 applied for smoothing or resolution of other structural abnormalities resulting from the process. Other process may use one point of contact, especially at high frequencies.

Figures 11A, 11B:
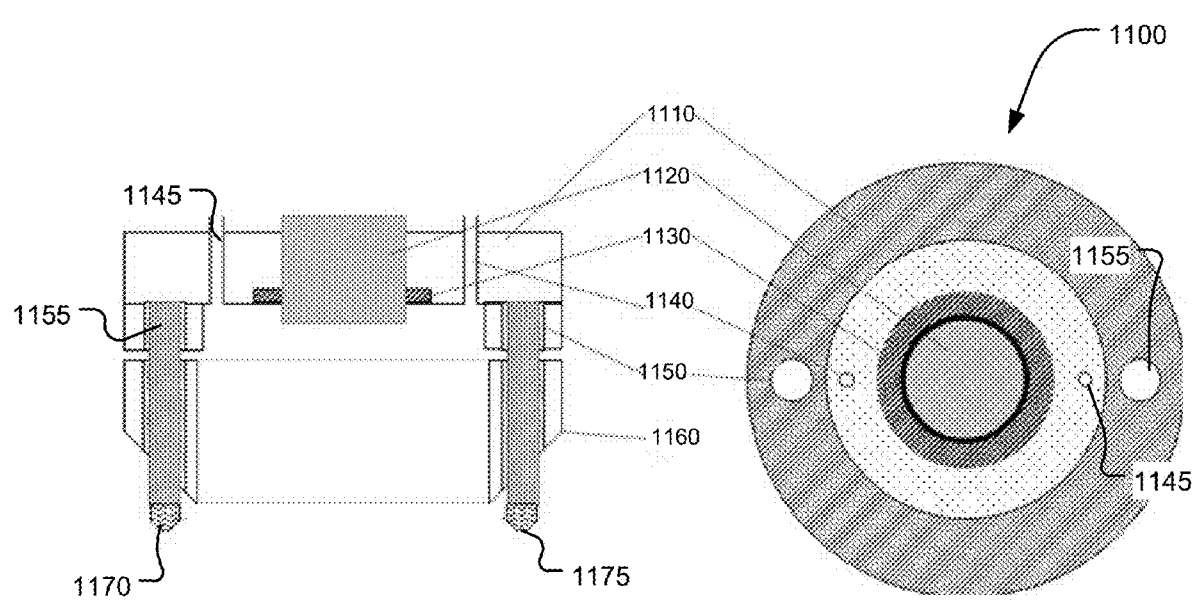
FIGS. 11A and 11B depict a gun or wand type applicator 1100 from a representative section view (FIG. 11A) and from a top view (FIG. 11B), as an embodiment of an electrode applicator unit 1010.

Gun or wand applicators may have an application system similar to that shown in a representative section view at FIG. 11A and a top view at FIG. 11B. The base 1110 of the applicator 1100 may have a feedthrough for a corroding electrode, or a seat for an interchangeable non-corroding source of a counterchage 1120. Any corroding electrode described here may be used. The seal electrically polarizes the first electrode. The seal defines one point of contact so far as the circuit is concerned, even though the geometry of the contact encloses a large area. The base 1100 may also have an electrode 1130 separate from 1120. Electrode 1130 may be a parallel source of a counterchage to modify or stabilize the total first current without changing the potential through the source of a counterchage 1120. In this way co-deposition may be controlled independently of the overall deposition process.

If a reverse pulse deposition process or corrosion of the first electrode is chosen, then electrode 1130 may be a cathode so reduction on the source for a counterchage 1120 is not mandatory. Electrode 1130 may instead be a reference electrode (e.g. 148 in FIG. 10), or a separate reference electrode may be placed in a similar location on the applicator 1100. Electrode 1130 may be a single surface, or multiple surfaces with directional control. Electrolyte may be circulated through the system via one or multiple, opposing channels 1140, 1145. The applicator 1100 may contain one or more channels 1150, 1155 for fresh and depleted electrolyte.

The applicator 1100 may contain two sources of counterchage 1120, which contact the first electrode via the tip 1160, inducing a second current across the first electrode. The sources of counterchage 1120 electrically contact the first electrode through caps 1170, 1175. The caps 1170, 1175 may comprise carbon or soft metal pads, or harder metal pins when it is desirable to increase localized current density of the second current.

Flow and electrode geometry inside the applicator 1100 may be two-dimensionally symmetric. Alternatively, the flow pattern may include a electrolyte influx down the center of the applicator, to the tip 1160, followed by outflux along the outer perimeter of the applicator 1100.

The interchangeable tip 1160 provides space for the electrolyte. The tip 1160 may have a sealing material around its opening to isolate the electrolyte from the channels 1150, 1155 when in contact with a surface. The channels 1150, 1155 may be used with or without separate leads identically polarized and connected to the first electrode. The caps 1170, 1175 may isolate the electrolyte from oxygen and moisture.

The tip 1160 of a gun or wand applicator 1100 may be fixed or removable. Primarily, the area and geometry of the opening of the tip 1160 would determine the surface area of the first electrode contacted, and therefore the area onto which new material is electrodeposited. Secondarily, the area and geometry of the tip 1160 may exploit surface tension of the electrolyte to influence fluid from draining from the aperture when the tip volume is full. The tip 1660 or applicator 1100 body may contain an agitator for the electrolyte, including higher frequency ultrasonic transducers, very low frequency vibrators, or any related mechanism. The tip may be designed for directional use. A scoop-like tip may use sheering force of the first electrode surface to push electrolyte back into the applicator as the tip is guided across the surface of the first electrode.

The base or tip may house a chemically resistant thermocouple or thermal resistor (thermistor) to monitor heat flux near the surface of the first electrode. The tip may be constructed of a semi-flexible material to facilitate consistent contact against non-planar surfaces and to provide a seal against excess electrolyte leaving the boundary of the tip opening. Fluid behavior at this junction may also be controlled by selecting the viscosity of the electrolyte and the diameter of the tip aperture to constrain the electrolyte.

The tip may contain a dielectric mesh, which contacts the surface of the first electrode to distribute the second current by minimizing energy absorption by the electrolyte at hot spots. When present, the mesh may be have a porosity between about 1 mm and about 1 µm to avoid any slowing of mass transport between the electrolyte and the surface of the first electrode. The mesh may also have openings, such as a slits can be oriented over a junction or gap in the first electrodes. The material of the source for a counterchage may closely match the material composition of the first electrode.

Referring to FIGS. 10 and 11, the tip 1160 may contain a reference electrode (RE) 148 of the $1^{st}$ or $2^{nd}$ kind. Short, single data point feedback measurements using the RE may use an RE of the $1^{st}$ kind (RE1) may comprise noble metals, Pt, Pd, Au, Ag, or others. With these reference electrodes, fast potential measurements may be recorded while the surface state of the RE is relatively stable. Polarization of the RE over longer time domains would allow the measured feedback potential to drift as the RE1 surface conditions become more transient. To obtain feedback over longer periods, an RE2 should maintain a steady-state potential while continuously polarized in solution. An example RE2 would be Ag/AgCl.

With a patch-type applicator 1200, referring to FIGS. 10, 12A and 12B, new metal deposition can be achieved by adhering the patch 1200 over the area of the first electrode 110 to which new metal will be deposited. The patch may have an adhesive or magnetic area 1210 by which to attach to a first electrode 110. At the center of the patch may be an inset, electrochemically active area 1220, composed of a conductive back layer, such as a metal foil. In various embodiments, this back layer may be a corroding or non-corroding electrode, which provides a source of a countercharge 120. The remaining volume of the inset may be filled with electrolyte 140. The electrolyte 140 may be of high viscosity, such as a gel, or be of low viscosity contained within a sponge or porous membrane. Any electrolyte described herein may be used. The perimeter of active area 1220 may have a contiguous seal made of silicone, latex, or similar material. This seal, when present, may isolate the electrolyte 140 from auxiliary contact pads 1230, 1235, which provide electrical contact with the first electrode 110.

Two contacts pads 1230, 1235 are shown at FIGS. 12A and 12B, more may be used in any orientation around the active area 1220. The pads 1230, 1235 provide first current 130 to the electrochemically active area 1220 of the first electrode 110 and second current 150 across the area of treatment. The patch 1200 may be as long as desired or of any geometry so that the electrochemical process can occur over a larger area at one time. Power may be provided to the patch through a cable 1240, which may lead to a power supply/control unit 1030, or the patch 1200 may be powered by an onboard battery and simple control circuit. Leads 1241, 1242 connect the cable 1240 to pads 1230, 1235. A single electrical contact point touching the surface may also be used.

Referring now to FIG. 13, the applicator 1300 may be integrated into a wearable glove 1310, permitting tactile sensory feedback with manual articulation. Corroding or non-corroding source of a countercharges may be seated into the first electrode holder 1320, or the entire tip of the digit may provide a source of a countercharge. Similar sources of countercharge 1330, 1335 may be on the tips of the nearest digits. The first circuit is completed between the first electrode holder 1320, the first electrode, and the sources of countercharge 1330, 1335, while the second circuit is completed through the sources of countercharge 1330, 1335 and the first electrode. Each circuit may be powered by wires 1340, 1342, 1343 leading to a junction or gap 1350, which is connected to a wire 1360 leading to a power supply/control unit, or an onboard battery/control system. The user can articulate the first electrode holder 1320 to control the area of deposition while changing the relative positions of the sources of countercharge 1330, 1335 to control the vector of second current. Other digits or multiple gloves may be used.

In the configurations, the applicator 1010 may further comprise a heating unit 146 or a cooling unit 147. These units 146,147 modulate the temperatures of the electrolyte 130 within the channels 145 of the electrode applicator unit 1010.

III. Software

The present disclosure further encompasses software for operating devices described herein and for performing methods described herein.

For example, the MCU may be programmed to use common materials such as steel, Cu, Ni and Zn, along with the appropriate electrolyte for each material. The MCU may be modified with enhanced programming to modulate the efficient electrodeposition of more complex alloys and composites.

The MCU may have wired or wireless networking or computer-linking connectivity. These connections may be load sensor data logs to a computer readable medium. The connections may facilitate computer control during operation of the method, live remote monitoring, and communication between multiple MCUs. The connections may receive software updates, including operating parameters and models for different substrate materials and electrolytes. For example, party A may create a electrolyte with special operating parameters and create a computer model that can be loaded onto the MCUs for other users.

The software may allow the MCU to control the deposition and second current functions during operation within minimal input from the user. Parameters may be initially entered into the MCU, or changing periodically to refine the process, so that user feedback during operating is largely limited to starting and stopping the process.

EXAMPLES

The following symbols and abbreviations are used throughout the present disclosure:

$\partial$ Average diffusion layer thickness of reactive species in electrolyte
A Area of flux ($m^2$)
AC Alternating current
c Speed of light ($3\times10^8$ m/s)
CA Corroding Source of a countercharge
D Longest EMR-active dimension of an electrode (m)
DC Direct current
$\vec{E}$ Electric field vector
$E_{ED}$ Electric field induced by an electrodeposition between a source of a countercharge and a first electrode (V/m)
EMIC 1-Ethyl-3-methylimidazolium chloride
EMR Electromagnetic radiation
$E_r$ Electric field radial to a point charge
$E_{TC}$ Electric field induced by second current (V/m)
$E_\theta$ Electric field perpendicular to $E_r$
$\in_o$ Permittivity of free space ($8.85\times10^{-12}$ $C^2/Nm^2$)
f Frequency
$F_{DP}$ Dielectrophoretic force
$F_{EP}$ Electrophoretic force
$\vec{H}$ Magnetic field vector
$H_{sine}$ Amplitude of a sinusoidal profile use to approximate surface roughness
I Current (amperes)
i(x) Current at point x on the electrode surface
$i_{ave}$ Average current density along a rough surface
$i_H$ Current density at the highest features of roughness
$i_L$ Current density at the lowest features of roughness
$I_{peak}$ Peak current
$I_{pp}$ Peak to peak current of a waveform
$I_{RMS}$ RMS Current
k Dielectric constant of a material
k $2\pi/\lambda$
MCU Main Control Unit
n Volumetric charge carrier density (e–/$m^3$)
OCP Open circuit potential
PCU Power Control Unit
$P_D$ Power at a depth, D, from the electrode surface
Pe– Radiative power of a non-relativistic, accelerating electron
$P_{ohm}$ Power dissipated by ohmic losses $P_{rad}$ Radiated power
$P_{TC}$ Applied power of second current
Q Charge of an electron (1.6 $10^{-19}$ C/e−)
$R_{CT}$ Charge transfer resistance of an electrochemical reaction
RE Reference Electrode
$R_{NF}$ Distance of the reactive near field from an electrode surface
$R_{peak}$ Peak resistance
$R_{RMS}$ RMS roughness of an electrode surface
$R_S$ Solution (electrolyte) resistance
RTIL Room Temperature ionic liquid
$S_D$ Skin depth
SHE Standard Hydrogen Electrode
TC Second current
v Velocity of charged particle
V Voltage
$V_D$ Drift velocity of a charged particle
$v_P$ Velocity of propagation
$V_{peak}$ Maximum voltage of a waveform
$V_{pp}$ Peak to peak voltage of a waveform
$V_{RMS}$ RMS Voltage
$V_{TC}$ Voltage of second current
Y Material attenuation constant of second current
$Y_{RMS}$ Attenuation constant of second current due to surface roughness
α Charge acceleration
γ Liénard electric field contraction constant
λ Wavelength
$\lambda_{TC}$ Wavelength of second current
μ Permeability of electrode
$\mu_o$ Permeability of free space (4π×$10^{-7}$ N/$A^2$)

Example 1—Smoothness and Uniformity Through Controlled Charge Distribution

This example demonstrated how charge density increases at points of surface curvature or irregularity. To measure this effect, matching substrates were processed using convention electrodeposition or using the disclose method. The substrates were then compared to each other.

Figure 14A:
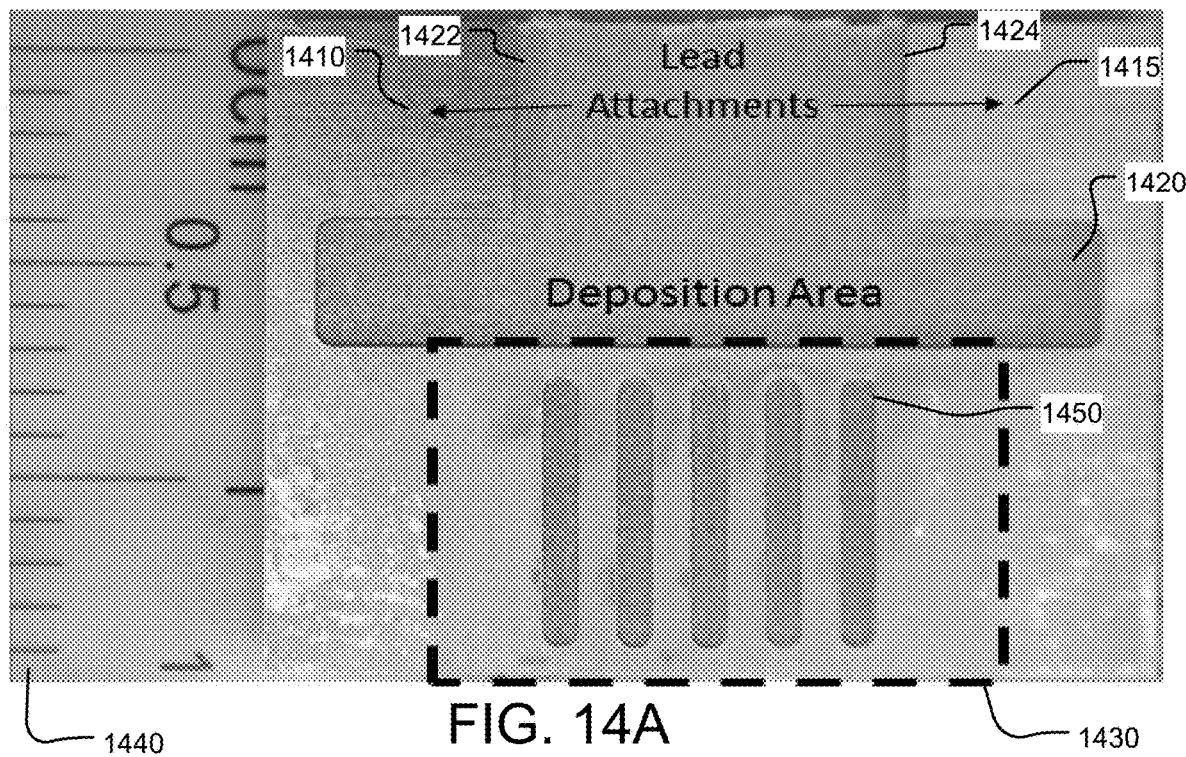
FIGS. 14A and 14B depicts a deposition from a saturated $CuSO_4$(aq) at 25° C., 30 mA/cm$^2$. Specifically, FIG. 14A was conducted without a second current; that is, a conventional electrodeposition).
Figure 14B:
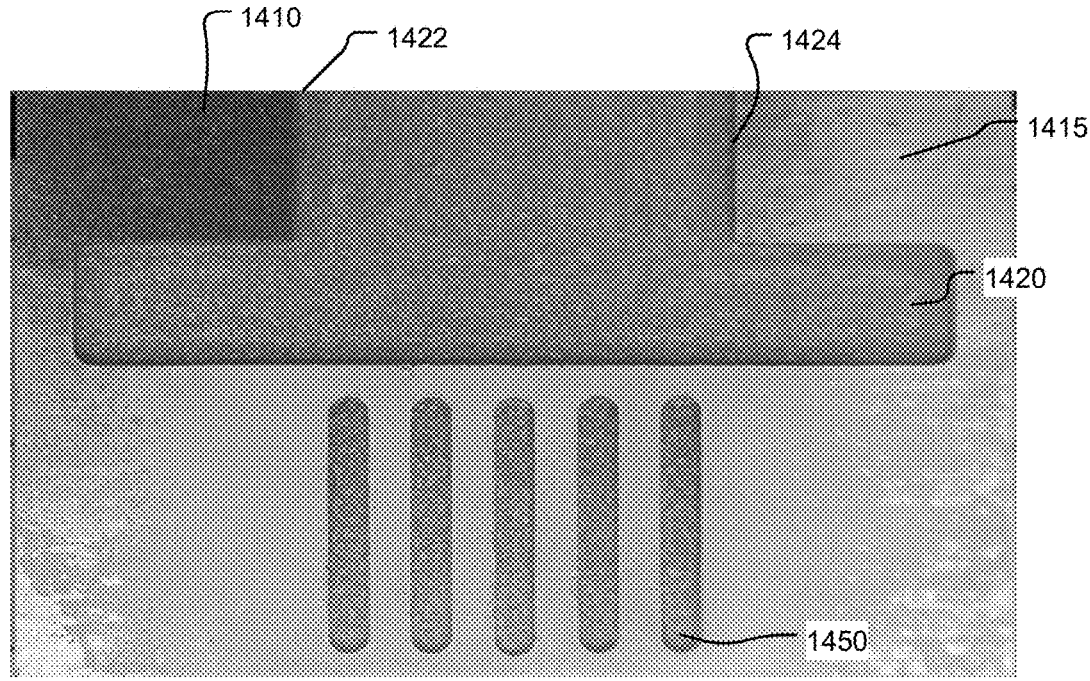

Referring first to FIGS. 14A and 14B, two 15 mm×18 mm copper electrodes were machined from an FR1 circuit board (a thin layer of copper over a non-conductive phenolic resin) with two lead attachments 1410, 1420, a deposition area 1450, and five 0.8-mm wide slots 1450. Lead attachment 1410 was on a first side 1422 of the slots 1450. A second lead attachment 1415 was on a second side 1421 of the slots 1450. Slots 1450 functioned as voids in the workpiece, so that current flow was blocked with a potential drop on either side of the slot 1450.

FIG. 14A shows the results of electrodeposition of copper at 30 mA/$cm^2$ without a second current; that is, under conventional electrodeposition. FIG. 14A shows the development of darker areas toward the top of the deposition area where charge built up. These darker areas comprised a rougher deposit and an increase in copper oxide.

FIG. 14B shows another workpiece resulting from electrodeposition of copper at 30 mA/$cm^2$ with a second current of 5-MHz at 10 Vpp applied between the lead attachments 1410, 1415. The same electrodeposition conditions were used in FIG. 14B as in FIG. 14A, but this time with the second current applied across the workpiece, with the attributes of the current as introduced immediately above. FIG. 14B shows the same electrodeposition conditions, but this time with second current applied. By inducing high frequency movement of the electrons on the surface of the first electrode, the charge was more evenly distributed across the surface, resulting in uniform deposit across the entire surface of the first electrode.

Figure 15A:
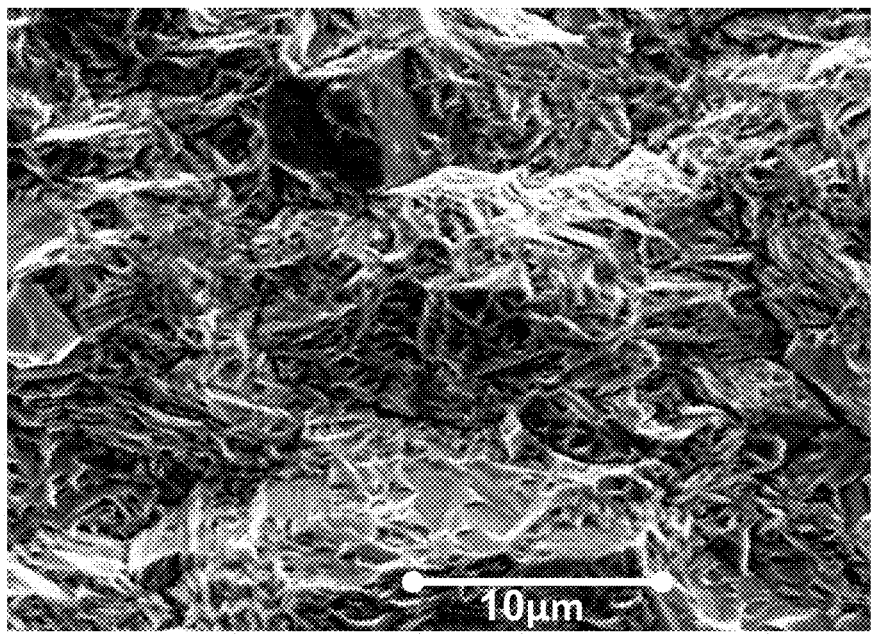
FIGS. 15A and 15B depict a deposition of copper from 1.25 M $CuSO_4$(aq) electrolyte at 25° C. and 15 mA/cm$^2$ for 1 hour. Specifically, in FIG. 15A no second current was applied; that is, it was a conventional electrodeposition. At FIG. 15B a second current of 1 MHz at 27 dbm (50Ω) was applied.
Figure 15B:
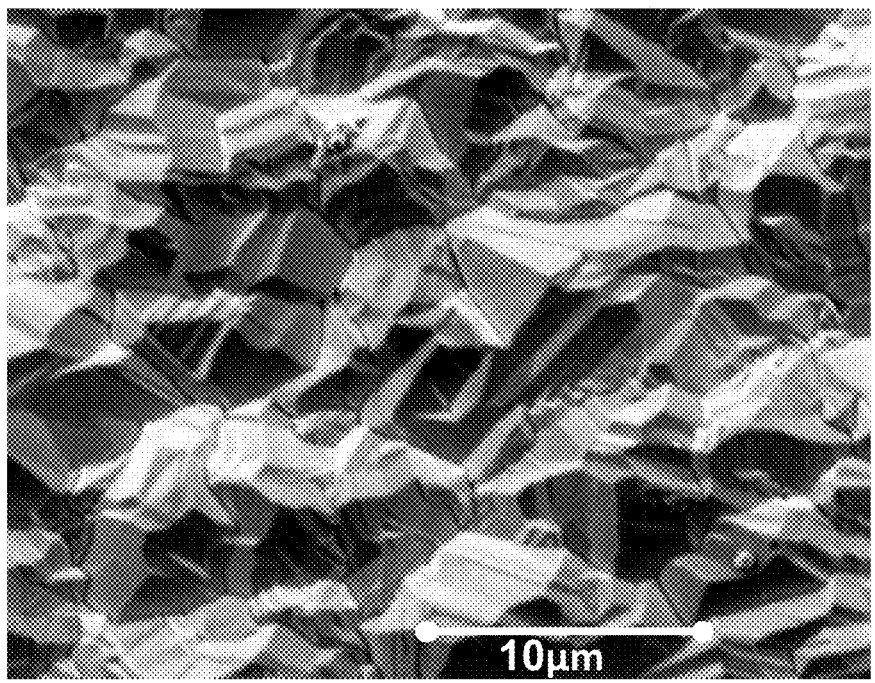

A comparison at the microscopic level of copper growth without and with the second current is shown in FIGS. 15A and 15B, respectively. FIG. 15A depicts an electron micrograph of a deposit formed form a 1.25 M $CuSO_4$(aq) using conventional deposition. This electron micrograph showed rough growth at the surface, which scattered the electron beam from the microscope. Porous edges grew outward, while voids were simultaneously filled in. The growth seen in FIG. 15A resulted from kinetic roughening and occurred when the nucleation rate was high relative to the actual growth rate. At longer deposition periods, these edges propagated faster than the voids were filled, leading to more dendritic morphology.

FIG. 15B depicts an electron micrograph of a deposit formed when a second current of −27 dbm at 1 MHz was applied to the workpiece under the same conditions as FIG. 15A. For ease of comparison, FIGS. 15A and 15B were set with the same size scale. All measurable porosity disappeared on the surface and the growth proceeded with limited nucleation (non-dendritic growth) followed by two-dimensional surface completion.

The type of growth seen in FIG. 15A is kinetic roughening and occurred when the nucleation rate is high relative to the actual growth rate. In FIG. 15, however, the current efficiency of deposition remained unaltered by the second current. The second current lowered the nucleation rate while the overall rate of growth remained consistent as two-dimensional expansion. The electric field of second current increased the surface diffusion rate of adsorbed metal instead of immediate nucleation with complete charge transfer. Therefore, the entropy of the surface was lower than normal. The degree of crystallinity can be controlled by modulating the second current to achieve the desired deposit properties.

Conventionally, irregularities are managed with slower deposition current densities, chemical additives (levelers/brighteners), large electroplating baths, or anodes at all sides. Applying a second current instead provided a simple means by which to reduce or avoid these conventional practices. The uniform distribution of charge afforded by the second current reduced the disproportionate growth normally observed at edges and points. Consequently, the uniformity of growth became less dependent upon the relative position of an anode.

By inducing high frequency movement of the electrons on the surface of the first electrode under the methods used in FIGS. 14B and 15B, the charge was more evenly distributed across the surface than using conventional electrodeposition in FIGS. 14A and 15A, resulting in uniform deposit across the entire surface of the workpiece. The surface-distributed charge arose from multiple mechanisms operating together. On average, the electrode was uniformly polarized, which led to a uniform concentration distribution of reactant species near the surface.

Adhesion of electrodeposited metal was challenging because native oxide layers form on metal surfaces in the presence of oxygen or moisture. These layers are conventionally removed using strong acids to etch the metal surface before new metal is deposited without allowing significant oxygen to enter the system at any point. Mechanically strong bond formation is a higher energy process. This is part of the reason deposited layers can grow on a substrate only to be easily peeled off later, and why the edges of two first electrodes may grow completely together with deposition but fall apart upon later handling.

By using electrolyte chemistry that supported reversible or semi-reversible corrosion, treatment with strong acids was avoided by first corroding the surface oxide layer into solution to expose bare metal at the surface of the first electrode. Corrosion-based surface exposure may be performed with the first current between the first electrode and a source for a countercharge, or independently of a source for a countercharge with just the second current running through the first electrode.

Figure 16:
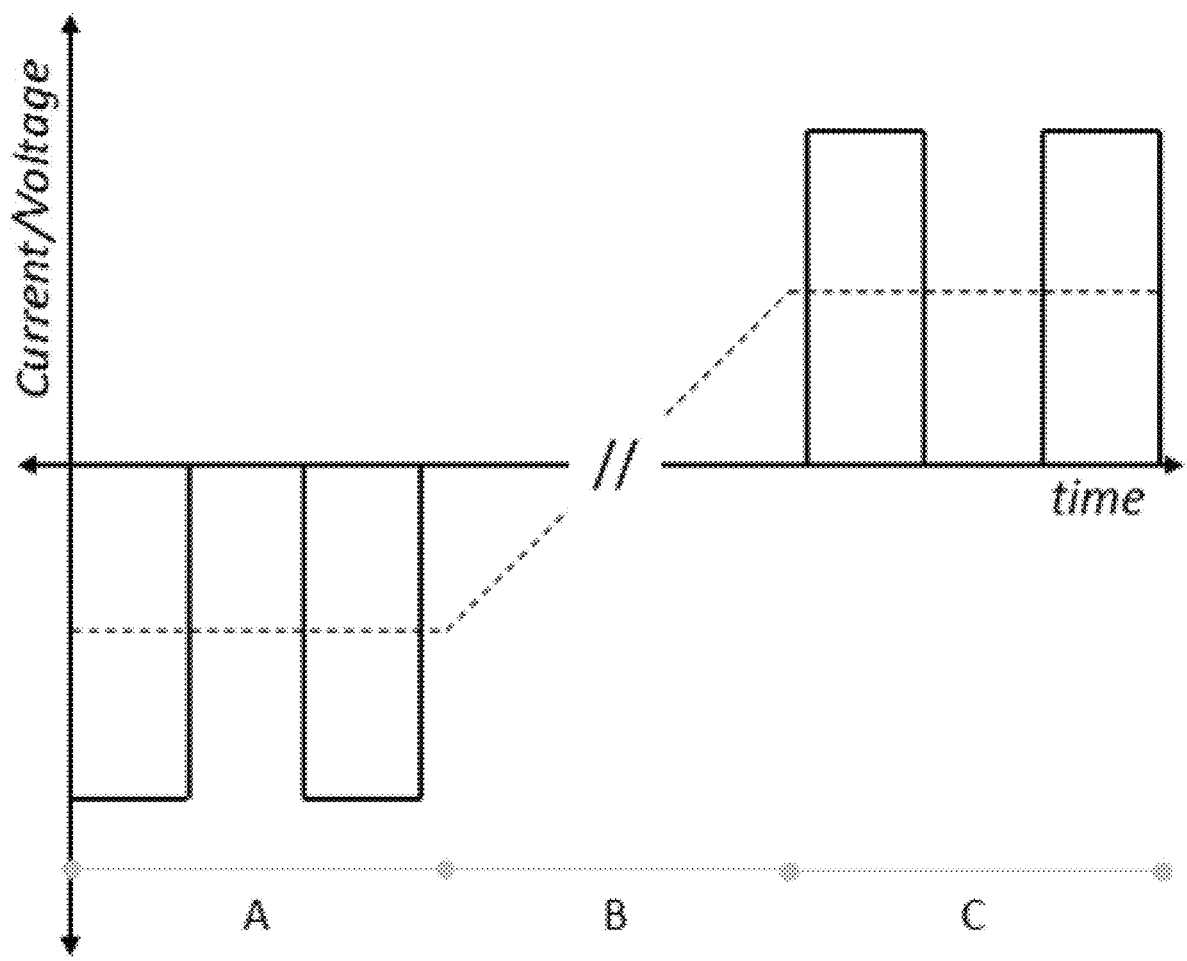
FIG. 16 depicts an electrochemical circuit pulsed adhesion scheme, which may be performed without a second current.

Superior adhesion of a metal onto a substrate was also obtained without conventional surface pre-treatments using DC, AC, or pulse corrosion currents, shown in FIG. 16. During Period A, the pulses alternated between neutral and corrosion-inducing potentials. Corrosion at ≥100 mA/cm$^2$ encouraged the release of bulk pieces of the substrate via corrosion along grain boundaries. The pulses had a defined pulse length of uniform or non-uniform duty cycle and a DC offset indicated by the dashed line.

Once the surface was roughened during Period A, the DC offset was transitioned to more a reducing potential over Period B, so the ratio of reducing to oxidizing current slowly increased. During Period C, the pulses were entirely neutral or reducing. The final magnitude of the reducing pulse equaled that at which deposition current was maintained thereafter.

The duration of Period C may be prolonged if significant roughening occurred during Period A. The frequency of pulses was usually between about 1 Hz and about 1 kHz (and lower for surfaces with significant polarization resistance). Faster frequencies become ineffective due to comparatively slow mass transport rates. DC current may instead be used for Periods A and C, only. Examples of systems suitable for DC current included the most non-reactive metals in aqueous solutions, or reactive metals in ionic liquids, in which the most highly oxidized metal species remains reducible to a metallic state.

Period B was effective at reducing thick passivation layers on the first electrode. Conventional pulse deposition or reverse-pulse deposition methods are not sufficient to remove the passivation layers on more reaction metals like Fe, Al and Ti. For example, on a passivated nickel surface, the passivation layer comprised a mixture of nickel oxide and nickel hydroxide atop the outer metallic boundary. Charges must transverse this layer through each oxidation state before reducing completely. In contrast, deposition onto non-passivating surfaces such as Au went by comparatively simple adsorption and charge transfer steps.

Example 2—Surface Repair

This example demonstrates the effectiveness of the second current in rejoining the surface of a first electrode. FIGS. 17A-L show a progression of surface smoothing on a copper electrode 1700 of 1 cm$^2$. FIG. 17A is the first image in the series, which was cut down the middle 1710 with shears before the rejoining process began. Several horizontal imprints 1720 are labeled in FIG. 17A (the same imprints are also evident in the other views through FIG. 17J) are apparent from pliers used to straighten the workpiece after shearing (FIG. 17A). The first electrode, in this case the sheared copper sample, is viewed from the perspective of the source for a countercharge through the electrolyte (one-half saturation CuSO$_4$(aq) at ambient temperature).

At the start of the process, the Cu surface received no chemical pre-treatment (FIG. 17A). To roughen the surface for demonstration of crack filling, the copper workpiece (first electrode) was exposed to a 100 mA first current for several minutes (FIG. 17B). At this high current density, the metal from the first electrode primarily corroded in small chunks, starting at the outer edges of the first electrode. After several minutes, the surface of the first electrode was substantially rough (FIG. 17C). This roughening was much more than needed to remove surface oxides and promote adhesion of deposited metal, but the extreme roughness provided a useful visual of the effects of the second current.

The first current was applied at 15 mA (−0.5 V) from the source of a countercharge through the electrolyte, while two second currents were applied across the copper workpiece (first electrode) (FIG. 17D). The first transverse current ($TC_1$) was sinusoidal at 1 MHz 3Vpp (50 ohm) between leads position on the workpiece equidistant from the shear 1710. The second transverse current ($TC_2$) had the same attributes as the first transverse current but phase offset by 90°. Two-dimensional growth dominated despite a perpendicular positing of the source of a countercharge to the surface of the workpiece (as shown in the sequence of images from FIG. 17D to 17I). Normal charge density at edges of roughness was avoided. Instead, the horizontal imprints 1520 were filled in, which is also shown in the sequence until they disappear after having been filled as shown in FIGS. 17K and 17L. As processing progressed, the original smooth surface was restored, resulting a relatively smooth workpiece with the shear filled as well as the imprints (FIGS. 17J-17K). As most of the surface of the first electrode 1700 was restored, remaining valleys had a planar bottom and growth proceeded vertically until the valley was filled in with new metal-metal bonds formed between metal from the electrolyte and the metal of the walls of the valleys.

An appropriate waveform and parameters should be selected to induce the filling effect. This example was performed with simple sinusoidal waves at a fixed voltage, frequency, and phase offset. Had parameter settings been dynamic and able to adapt to the changing surface over time, as with sensory feedback, the surface features of the first electrode may be filled and smoothened simultaneously. Other factors that may affect the deposition and bonding are the position of the leads inducing the current across the workpiece, as well as the position of the source of countercharge relative to the workpiece, among other factors.

Without any second current, the sample would have only demonstrated the outcome of conventional electrodeposition. From FIG. 17C onward, deposition would have propagated roughness instead of smoothing and filling.

Example 3—Second Current Controlled Adhesion

Figure 18A:
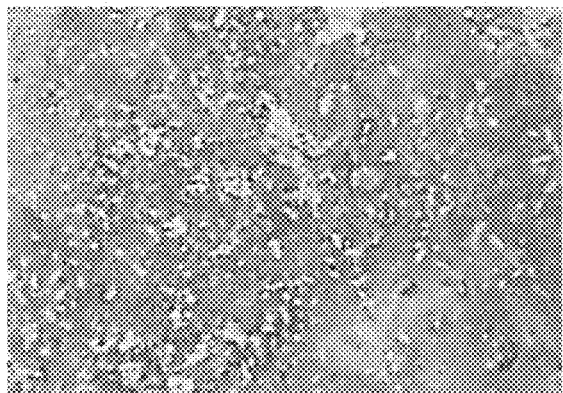
FIGS. 18A and 18B depict surface roughening of an originally smooth Cu/FR1 surface in 1.25 M CuSO$_4$(aq) at 25° C. using second current at 7 kV/30 mA (max limited) at 34 kHz (no counter electrode).
Figure 18B:
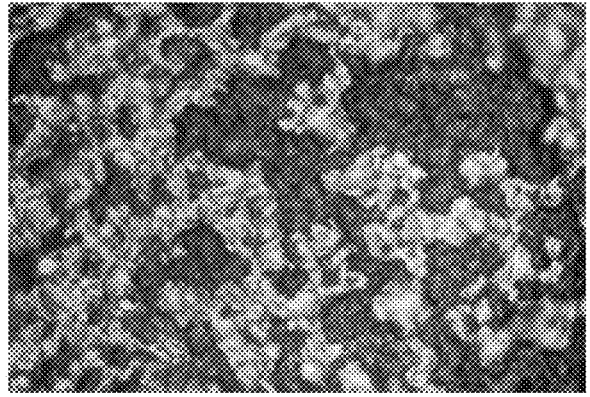

This example illustrates that the second (transvers) current can be used alone without absent deposition or corrosion under the first current. The second current alone was used at high potentials and modest frequencies to effect a high enough slew rate FIGS. 18A and 18B are electromicrographs of a workpiece showing corrosion-based surface roughening caused by the transverse current. In particular, a relatively high voltage of 7 kV at 34 kHz, limited to 30 mA, induced significant surface roughening in less than 5 seconds. The surface had the passivation layer removed along with some metal from the workpiece. The process may be influenced toward finer removal of material, or the process may increase corrosion using a first current between the workpiece and a source for a countercharge, or by modulating the second current to higher frequencies or higher powers. Conventional surface pretreatments were unnecessary when applying the second current, particularly when the most highly oxidized metal species remained reducible in the electrolyte.

The transverse current reduced the level of porosity that would otherwise appear during electrodeposition. This effect also made new material adhere better by improving the deposit quality at the substrate interface. Epitaxial growth caused the new layer of deposited metal to adopt the crystal orientation of the workpiece. Controlling this mechanism promoted good adhesion, and was useful when the layer and substrate were the same material, or were two materials with similar lattice spacing. With two crystallographically dissimilar materials, forced epitaxial growth can cause significant strain stored at the interface that will be prone to cracking. Here, the transverse current was modulated to roughen the surface or reduce porosity while allowing the relief of strain during deposition.

Example 4—Pressed Powder Corroding Electrode

Figure 19A:
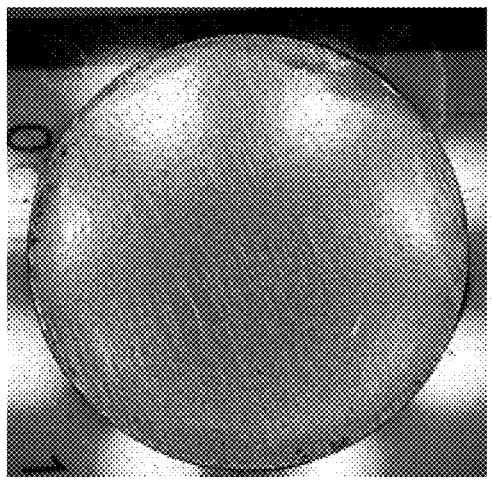
FIG. 19A depicts a corroding electrode formed from a pressed pellet containing Cu powder (about 10 μm average diameter) with 0.5% CuSO$_4$.
Figure 19B:
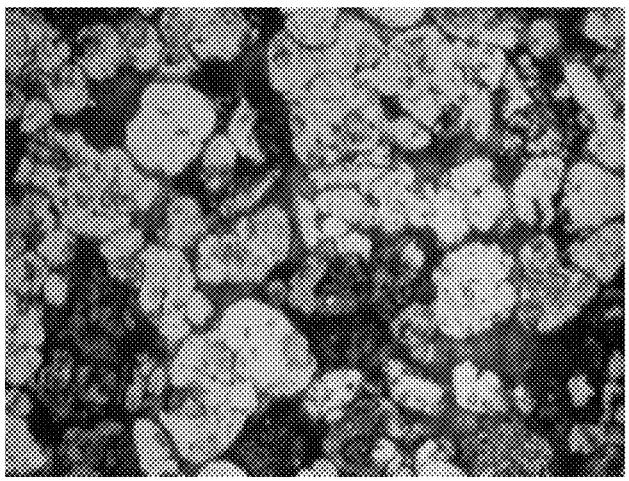
FIG. 19B presents the full view of the pellet.

Pressed power corroding electrodes were also investigated. FIG. 19A a photograph of a corroding electrode formed from pressed powder. The corroding electrode may be a source of countercharge, comprising mixed particles of various size, geometry, composition, and conductive or dielectric. The corroding electrodes included $CuSO_4$ with the metal particles, which were pressed together to replenishing the electrolyte as the electrode dissolved during operation. FIG. 19B is an electromicrograph of a deposit made using the corroding electrode of FIG. 19A.

Example 5—Bonding Using Computerized System

Figure 20:
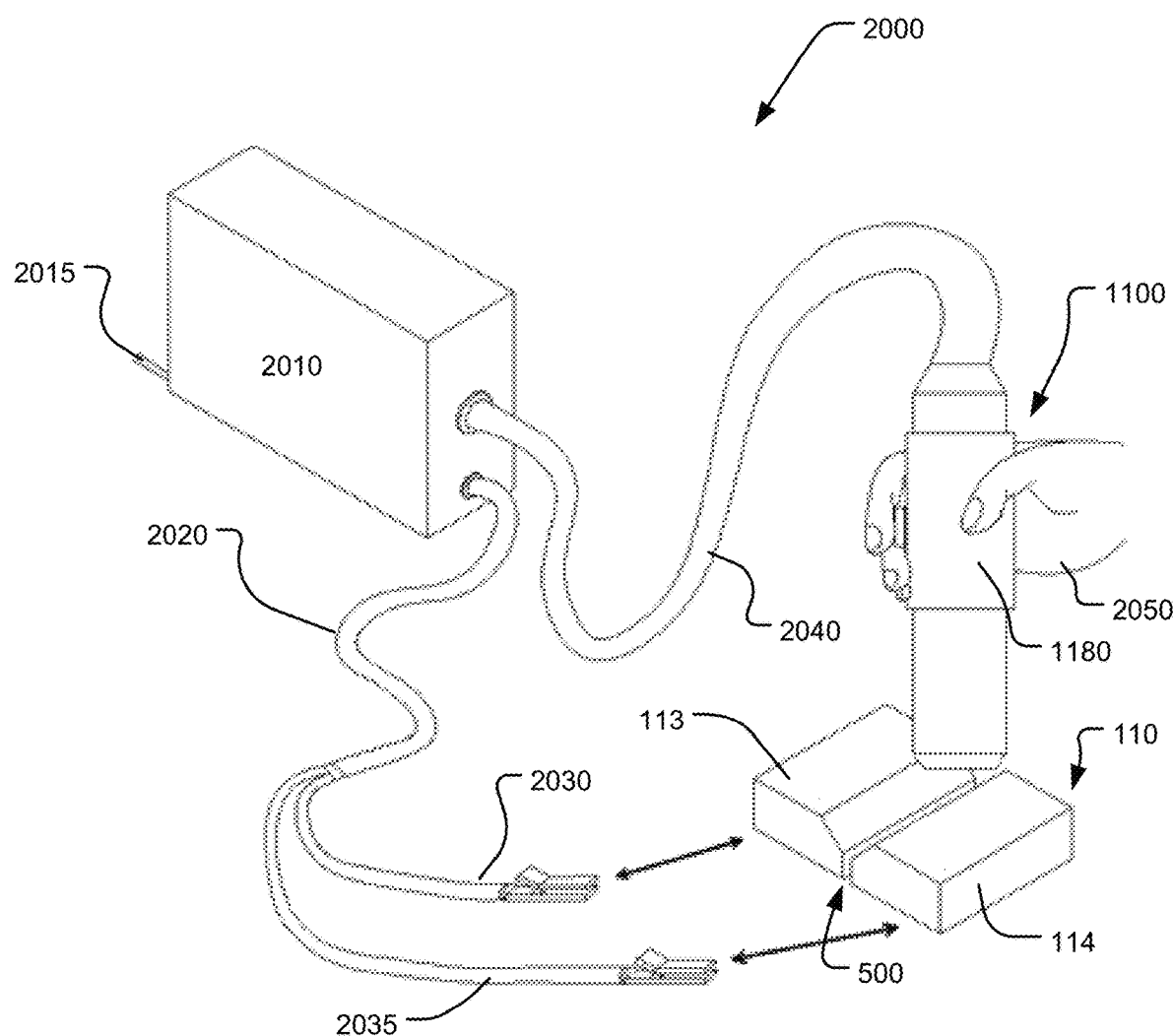
FIG. 20 provides an overview of unit 2000 in action as welding device with wand type applicator 1100 and auxiliary leads 2030, 2035.

To illustrate bonding using a computerized system described herein, reference is made to the device 2000 at FIG. 20. The electrolyte containing $AlCl_3$-EMIC is loaded into a reservoir of the main control unit (MCU) 2010 or the applicator 1100. The MCU 2010 is programmed to apply first current and second current power schemes selected for the Al—Fe electrolyte/corroding electrode combination. The device 2000 is powered from an external source such as a wall plug 2015.

Still referring to FIG. 20, The operator may attach two leads 2030, 2035 of the current collector cable 2040 to both portions 113, 114 of the first electrode 110 to polarize the first electrode 110 for the first circuit, and also to apply second current between the two leads 2030, 2035 through a surface of the first electrode 110. The portions 113, 114 are positioned relative to one another or in direct contact with one another to ensure a more even charge distribution across the first electrode 110. The user 2050 may forgo the leads 2030, 2035 for the sources of a countercharge built into the tip 1170, 1175 of the applicator 1100, as shown in FIG. 11. Alternatively, the user 2050 may use both, with the leads 2030, 2035 proving broad second current while the counterelectrodes of the applicator 1100 localize the second current across the area of the tip.

The electrolyte comprises polydisperse Fe particles having an average diameter between about 0.5 μm and about 1 μm, covered in 2 or 3 atomic layers of aluminum. The electrolyte also contains dissolved $AlCl_3$ at a molar ratio of about 1:1 with EMIC. See Example 12 for more details on deposition chemistry.

Within the applicator is a corroding electrode as a source of a countercharge comprising the same Al/Fe particles pressed into a 1-cm wide, 1-cm high pellet. As this electrode corrodes, the Al/Fe particle concentration of the electrolyte is replenished. The Al coating around each particle allows them to dissolve with an electroactive, reducible surface otherwise impossible for Fe in EMIC.

The material dimensions and composition are stable at temperatures below 80° C. Therefore, the operator may set the interior temperature of the applicator to 60° C. to promote deposition. The MCU's 2010 software may account for temperature and may modulate the applied power automatically.

The operator 2050 may manipulate the applicator 1100 to directly contact the junction 500 of the portions 113, 114 of the first electrode 110 with electrolyte from the tip. By manipulating the applicator 1100, the operator 2050 may activate one or more controls 1180 on the applicator 1100. These controls may execute the power sequences specified in the software controlling the MCU 2010. The sequence may include current to positively polarize the first electrode, removing the passivation layer on the surface. This step may be followed by a negative DC polarization of the first electrode with square wave second current at 1 kHz and 10 dbm and DC offset of 5 V. This waveform for the transverse current is designed to impart smoothness during deposition of the dissolved Al and Al—Fe particles. The transverse current also activates the gap defined by the two portions 113,114 of the first electrode 110 for deposition.

Capacitance- and impedance-based feedback measurements may inform the MCU of changes in the deposition environment. The feedback can detect solids suspended or dissolved in electric field between the workpiece and the source of a countercharge. The feedback can detect the decreasing surface area on the workpiece, which indicates that the surface has been smoothened. The feedback can also detect that a junction has been closed with newly deposited material. The feedback may allow the MCU to automatically modulate the applied potentials and current density.

Once the gap is filled, the DC offset is decreased to 0 V while the second current switched to 1 MHz and −60 dbm to continue imparting smoothness to later layers over the junction. The operator 2050 may start, stop or regulate the flow of electrolyte and power through all circuits in this way. The junction 500 is replaced by deposited material with chemical and physical properties similar to or the same as the two original portions 113,114 of the workpiece 110.

Example 6—Repairing Chemical Tank

Methods of the present disclosure may be used to repair a crack in the exterior of a tank storing several tons of chemicals. The disclosed method avoids the dangers of hot work (welding, brazing, cutting) normally used for these repairs, which could ignite or react the chemicals in the tank. Also, the tank need not be removed from service for repair, avoiding the loss of productive time and minimizing environmental exposure.

To perform the method, the surface of the crack is cleaned to remove paint, grease and dirt. With the surface clean, the worker applies an applicator patch over the crack. The patch contains a viscous Fe electrolyte containing Fe particles having a diameter between about 100 nm and about 300 nm, and a Fe corroding electrode as the source of a countercharge and additional Fe particles. Other metal species may be included in the electrolyte to match the alloy of the tank. Two contacts on the pad are oriented on either side of the crack so the second current propagates transverse to the crack's length. The patch, and several others like it, may cover other cracks on the tank. All patches are connected to a remotely controllable MCU.

The worker leaves the vicinity of the tank and safely controls the MCU remotely. The MCU is programmed to first apply a corrosion-roughening step through the electrochemical circuit. The roughened surface is primed for new metal deposition. Next, the MCU proceeds with slow deposition with second current of 10 dbm at 4 GHz and DC offset of 0.5 V. The second current frequency is chosen because it is sufficiently fast while not stimulating dangerous chemicals stored in the tank. Power is lost from dissipation across the crack. Power is set to 10 dbm compensate for this dissipation. Moreover, Fe particles in the electrolyte are sufficiently small to fill the width of the crack. The Fe particles are directed by the transverse current, the potential that it induces, the electrophoretic force of the 0.5-V DC offset in the waveform. In some instances, particularly at high frequencies that exceed the mobility of the charged species such as 4 GHz, the Fe particle may be too large to oscillate much at the high frequency. However, the transverse current can still induce a neutralizing effect ($V_{AVE}$ ca. 0) at sharp edges of the particles as well as the substrate. As a result, charged species are directed to deposit more uniformly regardless of surface features. The repair can be made with applying only the needed energy to the tank. When the repairs are complete, the worker removes the patches from the tank.

Repairs can be made more frequently because the disclosed methods are ease and safe compared to conventional dangerous hot work. The worker or his peers can assess the quality of the repair and maintain standards and process control following data review. And the quality and properties of the deposited metal are much higher than conventional welds, are better matched to the tank base material by selection of the metal species for deposit, and are more uniform than would otherwise be possible with conventional hot work repairs.

Having described several embodiments, it will be recognized by those skilled in the art that various modifications, alternative constructions, and equivalents may be used without departing from the spirit of the disclosure. Additionally, a number of well-known processes and elements have not been described in order to avoid unnecessarily obscuring the embodiments disclosed herein. Accordingly, the above description should not be taken as limiting the scope of the document.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

Exemplary Embodiments

The following is a listing of exemplary embodiments for methods and apparatuses disclosed herein:

1. A method comprising:
    inducing a first current between a source of a countercharge and a first electrode, the first current being through an electrolyte;
    inducing a second current across the first electrode, the second current being transverse to the first current, and the second current inducing a relativistic charge across the first electrode.

2. The method of claim 1, wherein the first electrode is a working electrode.

3. The method of claims 1-2, the electrolyte comprising a metal, the first electrode having a void with a metal edge, the relativistic charge causing a metal-metal bond to form between metal from the electrolyte and the metal edge to thereby fill the void.

4. The method of claim 3, wherein the void is a crack, crevice, or fracture in the first electrode.

5. The method of claim 3, the void forming a gap between a first portion of the first electrode, the first portion having a first edge of the metal edge, and a second portion of the first electrode, the second portion with a second edge of the metal edge proximate the first edge, the relativistic charge causing the metal-metal bond to form between metal from the first edge and metal from the electrolyte and between metal from the second edge and metal from the electrolyte, the bonded metals thereby bridging the gap to form a unified electrode of the first portion and the second portion.

6. The method of claims 1-5, wherein the source of a countercharge is an electrode counter to the first electrode.

7. The method of claims 1-6, wherein the electrolyte comprises a metal and one or more species selected from the group consisting of water, ammonium salts, metal chlorides, metal sulfates, ionic liquids, ionogels, and any combination thereof.

8. The method of claim 7, wherein the electrolyte comprises an ionic liquid, and the ionic liquid is a room temperature ionic liquid.

9. The method of claim 8, wherein the room-temperature ionic liquid is 1-ethyl-3-methylimidazolium chloride.

10. The method of claims 1-9, wherein the electrolyte comprises metal particles.

11. The method of claims 1-10, wherein the second current is chosen from an alternating current (AC) second current, or a combination of an AC second current and a direct current (DC) second current.

12. The method of claim 11, wherein the second current is the combination of the AC second current and the DC second current, the DC second current offsetting the AC second current by an amount less than an electrochemical breakdown of the electrolyte.

13. The method of claims 1-12, the second current having a waveform comprising a plurality of waveforms based on harmonics of one or more frequencies at which the electrolyte or the first electrode exhibits absorption of the one or more frequencies.

14. The method of claim 13, the second current having a phase offset of about 90° between an onset frequency voltage and an output amperage.

15. The method of claims 1-14, further comprising applying a signal cancellation to reduce a far-field radiation from the first electrode.

16. The method of claims 1-15, the second current having a period similar to a diffusion rate of a component in the electrolyte.

17. A method comprising:
    inducing an electric field between a source of a countercharge and a first electrode, the electric field having field lines through an electrolyte;
    inducing a potential across a surface of the first electrode, the induced potential bending the field lines proximate the surface such that metal from the electrolyte follows a path of the bent field lines to deposit the metal onto the surface.

18. The method of claim 17, wherein the first electrode is a working electrode.

19. The method of claims 17-19, the first electrode having a void with a metal edge, the induced potential causing a metal-metal bond to form between metal from the electrolyte and the metal edge to thereby fill the void.

20. The method of claim 19, wherein the void is a crack, crevice, or fracture in the first electrode.

21. The method of claim 19, the void forming a gap between a first portion of the first electrode, the first portion having a first edge of the metal edge, and a second portion of the first electrode, the second portion with a second edge of the metal edge proximate to the first edge, the relativistic charge causing the metal-metal bond between metal from the first edge and metal from the electrolyte and between metal from the second edge and metal from the electrolyte, the bonded metals to thereby bridging the gap to form a unified electrode of the first portion and the second portion.

22. The method of claims 17-21, wherein the source of a countercharge is an electrode counter to the first electrode.

23. The method of claims 17-22, wherein the electrolyte comprising one or more species selected from the group consisting of water, quaternary ammonium salts, metal chlorides, ionic liquids, ionogels, and any combination thereof.

24. The method of claim 23, wherein the electrolyte comprises an ionic liquid, and the ionic liquid is a room temperature ionic liquid.

25. The method of claim 24, wherein the room-temperature ionic liquid is 1-ethyl-3-methylimidazolium chloride.

26. The method of claims 17-25, wherein the electrolyte comprises metal particles.

27. The method of claims 17-26, wherein the second current is chosen from an alternating current (AC) second current, or a combination of an AC second current and a direct current (DC) second current.

28. The method of claims 17-27, the induced potential having a waveform comprising a plurality of waveforms based on harmonics of one or more frequencies at which the electrolyte or the first electrode exhibits absorption at the one or more frequencies.

29. The method of claim 28, the induced potential having a phase offset of about 90° between an onset frequency and an output amperage.

30. The method of claims 17-29, further comprising applying a signal cancellation to reduce a far-field radiation from the first electrode.

31. The method of claims 17-30, the induced potential having a period similar to a diffusion rate of a component in the electrolyte.

32. A method comprising: inducing a potential across a surface of an electrode in the presence of a chemical potential between an electrolyte and the surface of the electrode, the induced potential relativistically charging the surface of the electrode.

33. The method of claim 32, the relativistic charge causing a metal-metal bond to form between metal from the electrolyte and metal on the surface.

34. The method of claim 33, the electrode having a void with a metal edge, the relativistic charge causing the metal-metal bond between metal from the electrolyte and the metal edge to thereby fill the void.

35. The method of claim 34, the void forming a gap between a first portion of the electrode, the first portion having a first edge of the metal edge, and a second portion of the electrode, the second portion with a second edge of the metal edge proximate to the first edge, the relativistic charge causing the metal-metal bond to form between metal from the first edge and metal from the electrolyte and between metal from the second edge and metal from the electrolyte, the bonded metals to thereby bridging the gap to form a unified electrode of the first portion and the second portion.

36. The method of claims 32-35, wherein the electrolyte comprises metal and one or more species selected from the group consisting of water, quaternary ammonium salts, metal chlorides, ionic liquids, ionogels, and any combination thereof.

37. The method of claims 32-36, wherein the electrolyte comprises metal particles.

38. The method of claims 32-37, wherein the induced potential is chosen from an alternating current (AC) induced potential, or a combination of an AC induced potential and a direct current (DC) induced potential.

39. The method of claim 38, wherein the induced potential is the combination of the AC induced potential and the DC induced potential, the DC induced potential offsetting the AC induced potential by an amount less than an electrochemical breakdown of the electrolyte.

40. The method of claims 32-39, the induced potential having a waveform comprising a plurality of waveforms based on harmonics of one or more frequencies at which the electrolyte or the electrode exhibits absorption at the one or more frequencies.

41. The method of claim 40, wherein the induced potential comprises a phase offset of about 90° between an onset frequency and an output amperage.

42. The method of claims 32-41, further comprising applying a signal cancellation to reduce a far-field radiation from the electrode.

43. The method of claims 32-42, the induced potential having a period similar to a diffusion rate of a component in the electrolyte.

44. The method of claims 1-43, wherein the first electrode comprises at least two galvanically reactive metals meeting a junction, the second current reducing corrosion at the junction.

45. The method of claim 44, wherein the second current distributes charge away from grain boundaries on the surface of the first electrode and avoids corrosive pitting at the surface of the first electrode.

46. The method of claims 1-43, wherein the first current has a positive potential sufficient to corrode away a rough feature at the surface of the first electrode.

47. The method of claim 46, wherein the first current is applied with a low current density, a pulsed current density, or a combination of a low, pulsed current density.

48. The method of claims 1-31, wherein metal from the electrolyte bonds to a vacant site on the surface of the first electrode or the source for a countercharge and not to a previously bonded metal.

49. The method of claim 48, wherein a membrane is disposed between the source for a countercharge and the first electrode, the source for a counterchange comprising $LiM_xO_y$, the first electrode comprising carbon or $Li^0$, the metal from the electrolyte comprising Li+, and the previously-bonded metal comprising $Li^0$.

50. A corroding electrode comprising one or more metal species selected from the group consisting of metal particles, metal ions, and combinations thereof;

wherein the corroding electrode dissolves when a first current is applied between the corroding electrode and a first electrode through an electrolyte, thereby suspending the one or more metal species into the electrolyte.

51. The corroding electrode of claim 50, further comprising one or more ceramic particles or dielectric polymers.

52. The corroding electrode of claims 50-51, wherein the corroding source of a countercharge is formed by being pressed together into a solid body.

53. The corroding electrode of claims 50-52, wherein the metal particles have grain sizes selected to grain sizes of the first electrode.

54. The corroding electrode of claims 50-53, comprising metal particles having rough or non-symmetric dimensions.

55. The corroding electrode of claims 50-54, comprising metal particles having spherical dimensions and a uniform surface energy.

56. The corroding electrode of claims 50-55, comprising metal particles having an elongated dimension, which aligns with a second current induced across the first electrode, the second current being transverse to the first current, and the second current inducing a relativistic charge across the first electrode.

57. The method of claims 1-31, wherein the source of a countercharge is a corroding electrode of claims 50-56.

58. A device comprising:
   a source of a countercharge, and
   a first electrode in electrical communication through an electrolyte with the source of a countercharge;
   wherein a first current is induced through the electrolyte between the source of a countercharge and the first electrode; and
   wherein a second current is induced across the first electrode, the second current being transverse to the first current, and the second current inducing a relativistic charge across the first electrode.

59. The device of claim 58, wherein the first electrode is a working electrode.

60. The device of claims 58-59, the electrolyte comprising a metal, the first electrode having a void with a metal edge, the relativistic charge causing a metal-metal bond to form between metal from the electrolyte and the metal edge to thereby fill the void.

61. The device of claim 60, wherein the void is a crack, crevice, or fracture in the first electrode.

62. The device of claim 60, the void forming a gap between a first portion of the first electrode, the first portion having a first edge of the metal edge, and a second portion of the first electrode, the second portion with a second edge of the metal edge proximate the first edge, the relativistic charge causing the metal-metal bond to form between metal from the first edge and metal from the electrolyte and between metal from the second edge and metal from the electrolyte, the bonded metals thereby bridging the gap to form a unified electrode of the first portion and the second portion.

63. The device of claims 58-62, wherein the source of a countercharge is an electrode counter to the first electrode.

64. The device of claims 58-63, wherein the electrolyte comprises a metal and one or more species selected from the group consisting of water, quaternary ammonium salts, metal chlorides, ionic liquids, ionogels, and any combination thereof.

65. The device of claim 64, wherein the electrolyte comprises an ionic liquid, and the ionic liquid is a room temperature ionic liquid.

66. The device of claim 65, wherein the room-temperature ionic liquid is 1-ethyl-3-methylimidazolium chloride.

67. The device of claims 58-66, wherein the electrolyte comprises metal particles.

68. The device of claims 58-67, wherein the second current is chosen from an alternating current (AC) second current, or a combination of an AC second current and a direct current (DC) second current.

69. The device of claim 68, wherein the second current is the combination of the AC second current and the DC second current, the DC second current offsetting the AC second current by an amount less than an electrochemical breakdown of the electrolyte.

70. The device of claims 58-69, further comprising a waveform generator to provide the second current with a waveform comprising a plurality of waveforms based on harmonics of one or more frequencies at which the electrolyte or the first electrode exhibits absorption of the one or more frequencies.

71. The device of claims 58-70, further comprising a signal canceler to reduce a far-field radiation from the first electrode.

72. The device of claims 58-71, the second current having a period similar to a diffusion rate of a component in the electrolyte.

73. A device comprising:
   a source of a countercharge, and
   a first electrode in electrical communication through an electrolyte with the source of a countercharge;
   wherein an electric field is induced between the source of a countercharge and the first electrode, the electric field having field lines through the electrolyte; and
   wherein a potential is induced across a surface of the first electrode, the induced potential bending the field lines proximate the surface such that metal from the electrolyte follows a path of the bent field lines to deposit the metal onto the surface.

74. The device of claim 73, wherein the first electrode is a working electrode.

75. The device of claims 73-75, the first electrode having a void with a metal edge, the induced potential causing a metal-metal bond to form between metal from the electrolyte and the metal edge to thereby fill the void.

76. The device of claim 75, wherein the void is a crack, crevice, or fracture in the first electrode.

77. The device of claim 75, the void forming a gap between a first portion of the first electrode, the first portion having a first edge of the metal edge, and a second portion of the first electrode, the second portion with a second edge of the metal edge proximate to the first edge, the relativistic charge causing the metal-metal bond between metal from the first edge and metal from the electrolyte and between metal from the second edge and metal from the electrolyte, the bonded metals to thereby bridging the gap to form a unified electrode of the first portion and the second portion.

78. The device of claims 73-77, wherein the source of a countercharge is an electrode counter to the first electrode.

79. The device of claims 73-78, wherein the electrolyte comprises one or more species selected from the group consisting of water, quaternary ammonium salts, metal chlorides, ionic liquids, ionogels, and any combination thereof.

80. The device of claim 79, wherein the electrolyte comprises an ionic liquid, and the ionic liquid is a room temperature ionic liquid.

81. The device of claim 80, wherein the room-temperature ionic liquid is 1-ethyl-3-methylimidazolium chloride.

82. The device of claims 73-81, wherein the electrolyte comprises metal particles.

83. The device of claims 73-82, wherein the second current is chosen from an alternating current (AC) second current, or a combination of an AC second current and a direct current (DC) second current.

84. The device of claims 73-83, further comprising a waveform generator to provide the induced potential with a waveform comprising a plurality of waveforms based on harmonics of one or more frequencies at which the electrolyte or the first electrode exhibits absorption at the one or more frequencies.

85. The device of claims 73-84, further comprising a signal canceler to reduce a far-field radiation from the first electrode.

86. The device of claims 73-85, the induced potential having a period similar to a diffusion rate of a component in the electrolyte.

87. A first electrode, wherein a potential is induced across a surface of the first electrode in the presence of a chemical potential between an electrolyte and the surface of the first electrode, the induced potential relativistically charging the surface of the first electrode.

88. The first electrode of claim 87, the relativistic charge causing a metal-metal bond to form between metal from the electrolyte and metal on the surface.

89. The first electrode of claim 88, the first electrode having a void with a metal edge, the relativistic charge causing the metal-metal bond between metal from the first electrolyte and the metal edge to thereby fill the void.

90. The first electrode of claim 89, the void forming a gap between a first portion of the first electrode, the first portion having a first edge of the metal edge, and a second portion of the first electrode, the second portion with a second edge of the metal edge proximate to the first edge, the relativistic charge causing the metal-metal bond to form between metal from the first edge and metal from the electrolyte and between metal from the second edge and metal from the electrolyte, the bonded metals to thereby bridging the gap to form a unified electrode of the first portion and the second portion.

91. The first electrode of claims 87-90, wherein the electrolyte comprises metal and one or more species selected from the group consisting of water, quaternary ammonium salts, metal chlorides, ionic liquids, ionogels, and any combination thereof.

92. The first electrode of claims 87-91, wherein the electrolyte comprises metal particles.

93. The first electrode of claims 87-92, wherein the induced potential is chosen from an alternating current (AC) induced potential, or a combination of an AC induced potential and a direct current (DC) induced potential.

94. The first electrode of claim 93, wherein the induced potential is the combination of the AC induced potential and the DC induced potential, the DC induced potential offsetting the AC induced potential by an amount less than an electrochemical breakdown of the electrolyte.

95. The first electrode of claims 87-94, the induced potential having a waveform comprising a plurality of waveforms based on harmonics of one or more frequencies at which the electrolyte or the electrode exhibits absorption at the one or more frequencies.

96. The first electrode of claims 87-95, the induced potential having a period similar to a diffusion rate of a component in the electrolyte.

97. A device comprising:
a main control unit comprising a power supply and a power modulator;
an electrode applicator unit, comprising at least one source of a countercharge and a plurality of channels for flowing an electrolyte through the electrode applicator unit, the electrode applicator unit being connected to the main control unit;
a current collector cable connected to the main control unit; and
a power control unit connected to the main control unit, which power control unit applies a first current between a first electrode and the at least one source of a countercharge through the electrolyte, the power control unit inducing a second current across the first electrode, the second current being transverse to the first current, and the second current inducing a relativistic charge across the first electrode.

98. The device of claim 97, wherein the main control unit further comprises a computer for executing instructions stored on a computer readable medium.

99. The device of claim 98, wherein the power modulator and the power control unit are controlled by the computer.

100. The device of claims 97-99, wherein the main control unit further comprises an electrolyte storage tank, at least one pump, and tubing connected to the electrolyte storage tank, the at least one pump, and the electrode applicator unit; thereby flowing the electrolyte from the electrolyte storage tank through the tubing into the plurality of channels of the electrode applicator unit.

101. The device of claims 97-100, wherein the electrode applicator unit further comprises a heating unit or a cooling unit for modulating a temperature of the electrolyte within the channels of the electrode applicator unit.

102. The device of claims 97-101, wherein the current collector cable further comprises leads for attaching to the first electrode.

103. The device of claim 56-86 or 97-102, wherein the at least one source of a countercharge comprises a corroding electrode of claims 50-56.

104. The device of claim 56-86 or 97-102, wherein the device performs a method of claims 1-49.

What is claimed is:

1. A method comprising:
inducing a first current between a source of a countercharge and a first electrode, the first current being through an electrolyte;
inducing a second current conforming to a waveform, the second current across the first electrode, the second current being transverse to the first current, and the second current inducing a relativistic charge across the first electrode.

2. The method of claim 1, wherein the first electrode is a working electrode.

3. The method of claim 1, the electrolyte comprising a metal, the first electrode having a void with a metal edge, the relativistic charge causing a metal-metal bond to form between metal from the electrolyte and the metal edge to thereby fill the void.

4. The method of claim 3, wherein the void is a crack, crevice, or fracture in the first electrode.

5. The method of claim 3, the void forming a gap between a first portion of the first electrode, the first portion having a first edge of the metal edge, and a second portion of the first electrode, the second portion with a second edge of the metal edge proximate the first edge, the relativistic charge causing the metal-metal bond to form between metal from the first edge and metal from the electrolyte and between metal from the second edge and metal from the electrolyte, the bonded metals thereby bridging the gap to form a unified electrode of the first portion and the second portion.

6. The method of claim 1, wherein the source of a countercharge is an electrode counter to the first electrode.

7. The method of claim 1, wherein the electrolyte comprises a metal and one or more species selected from the group consisting of water, ammonium salts, metal chlorides, metal sulfates, ionic liquids, ionogels, and any combination thereof.

8. The method of claim 7, wherein the electrolyte comprises an ionic liquid, and the ionic liquid is a room temperature ionic liquid.

9. The method of claim 8, wherein the room-temperature ionic liquid is 1-ethyl-3-methylimidazolium chloride.

10. The method of claim 1, wherein the electrolyte comprises metal particles.

11. The method of claim 1, wherein the second current is chosen from an alternating current (AC) second current, or a combination of an AC second current and a direct current (DC) second current.

12. The method of claim 11, wherein the second current combines the AC second current and the DC second current, the DC second current offsetting the AC second current by an amount less than an electrochemical breakdown of the electrolyte.

13. The method of claim 1, the second current conforming to a waveform comprising a plurality of waveforms based on harmonics of one or more frequencies at which the electrolyte or the first electrode exhibits absorption of the one or more frequencies.

14. The method of claim 13, the second current having a phase offset of about 90° between an onset frequency voltage and an output amperage.

15. The method of claim 1, further comprising applying a signal cancellation to reduce a far-field radiation from the first electrode.

16. The method of claim 1, the second current having a period similar to a diffusion rate of a component in the electrolyte.

17. The method of claim 1, wherein the relativistic charge induced by the second current causes metal from the electrolyte to bond to the surface of the first electrode, and/or causes metal to corrode at the surface of the first electrode.

18. A method comprising:
inducing an electric field between a source of a countercharge and a first electrode, the electric field having field lines through an electrolyte;
inducing a potential waveform across a surface of the first electrode, the induced waveform potential bending the field lines proximate the surface so metal from the electrolyte follows a path of the bent field lines to deposit the metal onto the surface.

19. The method of claim 18, the first electrode having a void with a metal edge, the induced potential causing a metal-metal bond to form between metal from the electrolyte and the metal edge to thereby fill the void.

20. The method of claim 18, the void forming a gap between a first portion of the first electrode, the first portion having a first edge of the metal edge, and a second portion of the first electrode, the second portion with a second edge of the metal edge proximate to the first edge, the relativistic charge causing the metal-metal bond between metal from the first edge and metal from the electrolyte and between metal from the second edge and metal from the electrolyte, the bonded metals to thereby bridging the gap to form a unified electrode of the first portion and the second portion.

21. The method of claim 18, wherein the source of a countercharge is an electrode counter to the first electrode.

22. The method of claim 18, wherein the electrolyte comprises an ionic liquid, and the ionic liquid is a room temperature ionic liquid.

23. The method of claim 22, wherein the room-temperature ionic liquid is 1-ethyl-3-methylimidazolium chloride.

24. The method of claim 18, wherein the electrolyte comprises metal particles.

25. The method of claim 18, wherein the second current is chosen from an alternating current (AC) second current, or a combination of an AC second current and a direct current (DC) second current.

26. The method of claim 18 the induced potential having a waveform comprising a plurality of waveforms based on harmonics of one or more frequencies at which the electrolyte or the first electrode exhibits absorption at the one or more frequencies.

27. The method of claim 26, the induced potential having a phase offset of about 90° between an onset frequency and an output amperage.

28. The method of claim 18, further comprising applying a signal cancellation to reduce a far-field radiation from the first electrode.

29. The method of claim 18, the induced potential having a period similar to a diffusion rate of a component in the electrolyte.

30. The method of claim 18, wherein the induced potential waveform generates a relativistic charge on the first electrode, the induced potential waveform causes metal from the electrolyte to bond to the surface of the first electrode, and/or causes metal to corrode at the surface of the first electrode.

* * * * *